(12) United States Patent
Milo et al.

(10) Patent No.: US 10,077,437 B2
(45) Date of Patent: Sep. 18, 2018

(54) ENZYMATIC SYSTEMS FOR CARBON FIXATION AND METHODS OF GENERATING SAME

(71) Applicant: Yeda Research and Development Co. Ltd., Rehovot (IL)

(72) Inventors: Ron Milo, Kfar-Saba (IL); Arren Bar-Even, Tel-Aviv (IL); Elad Noor, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 10 days.

(21) Appl. No.: 15/189,021

(22) Filed: Jun. 22, 2016

(65) Prior Publication Data

US 2016/0298103 A1    Oct. 13, 2016

Related U.S. Application Data

(62) Division of application No. 13/576,720, filed as application No. PCT/IL2011/000145 on Feb. 10, 2011, now Pat. No. 9,410,131.

(60) Provisional application No. 61/303,338, filed on Feb. 11, 2010.

(51) Int. Cl.
| | |
|---|---|
| C12N 9/00 | (2006.01) |
| C12N 15/82 | (2006.01) |
| C12N 9/04 | (2006.01) |
| C12N 9/02 | (2006.01) |
| C12N 9/12 | (2006.01) |
| C12N 9/10 | (2006.01) |
| C12N 9/18 | (2006.01) |
| C12N 9/88 | (2006.01) |
| C12N 9/90 | (2006.01) |
| C12P 7/40 | (2006.01) |
| C12N 15/70 | (2006.01) |
| C12P 7/42 | (2006.01) |
| C12P 7/46 | (2006.01) |
| C12P 11/00 | (2006.01) |
| G06F 19/12 | (2011.01) |

(52) U.S. Cl.
CPC .............. *C12N 9/93* (2013.01); *C12N 9/0006* (2013.01); *C12N 9/0008* (2013.01); *C12N 9/1018* (2013.01); *C12N 9/1205* (2013.01); *C12N 9/13* (2013.01); *C12N 9/18* (2013.01); *C12N 9/88* (2013.01); *C12N 9/90* (2013.01); *C12N 15/70* (2013.01); *C12N 15/8245* (2013.01); *C12N 15/8247* (2013.01); *C12N 15/8269* (2013.01); *C12P 7/40* (2013.01); *C12P 7/42* (2013.01); *C12P 7/46* (2013.01); *C12P 11/00* (2013.01); *C12Y 101/01059* (2013.01); *C12Y 102/01018* (2013.01); *C12Y 201/03001* (2013.01); *C12Y 208/03001* (2013.01); *C12Y 401/01031* (2013.01); *C12Y 402/01017* (2013.01); *C12Y 402/01054* (2013.01); *C12Y 604/01001* (2013.01); *C12Y 604/01002* (2013.01); *G06F 19/12* (2013.01); *Y02P 20/52* (2015.11)

(58) Field of Classification Search
CPC ....................................................... C12N 9/93
See application file for complete search history.

(56) References Cited

U.S. PATENT DOCUMENTS

| | | | |
|---|---|---|---|
| 9,410,131 B2 * | 8/2016 | Milo | C12N 9/0006 |
| 2009/0191599 A1 | 7/2009 | Devroe et al. | |
| 2009/0203070 A1 | 8/2009 | Devroe et al. | |
| 2012/0301947 A1 | 11/2012 | Milo et al. | |

FOREIGN PATENT DOCUMENTS

| | | |
|---|---|---|
| WO | WO 03/081207 | 10/2003 |
| WO | WO 2009/036095 | 3/2009 |
| WO | WO 2011/099006 | 8/2011 |

OTHER PUBLICATIONS

Communication Relating to the Result of the Partial International Search dated Jun. 6, 2011 From the International Searching Authority Re. Application No. PCT/IL2011/000145.
International Preliminary Report on Patentability dated Aug. 23, 2012 From the International Bureau of WIPO Re. Application No. PCT/IL2011/000145.
International Search Report and the Written Opinion dated Sep. 28, 2011 From the International Searching Authority Re. Application No. PCT/IL2011/000145.
Notice of Allowance dated Mar. 7, 2016 From the US Patent and Trademark Office Re. U.S. Appl. No. 13/576,720.
Official Action dated Oct. 22, 2015 From the US Patent and Trademark Office Re. U.S. Appl. No. 13/576,720.
Official Action dated Apr. 30, 2015 From the US Patent and Trademark Office Re. U.S. Appl. No. 13/576,720.

(Continued)

*Primary Examiner* — Russell Kallis

(57) ABSTRACT

A system for carbon fixation is provided. The system comprises enzymes which catalyze reactions of a carbon fixation pathway, wherein at least one of the reactions of the carbon fixation pathway is a carboxylation reaction, wherein products of the reactions of the carbon fixation pathway comprise oxaloacetate and malonyl-CoA, wherein an enzyme which performs the carboxylation reaction is selected from the group consisting of phophoenolpyruvate (PEP) carboxlase, pyruvate carboxylase and acetyl-CoA carboxylase and wherein an export product of the carbon fixation pathway is glyoxylate. Additional carbon fixation pathways are also provided and methods of generating same.

11 Claims, 33 Drawing Sheets
(31 of 33 Drawing Sheet(s) Filed in Color)

(56) References Cited

OTHER PUBLICATIONS

Restriction Official Action dated Nov. 19, 2014 From the US Patent and Trademark Office Re. U.S. Appl. No. 13/576,720.
Bar-Even et al. "Design and Analysis of Synthetic Carbon Fixation Pathways", Proc. Natl. Acad. Sci. USA, PNAS, XP002638327, 107(19): 8889-8894, May 11, 2010.
Hall et al. "Transcarboxylase 5S Structures: Assembly and Catalytic Mechanism of a Multienzyme Complex Subunit", The European Molecular Biology Organization Journal, EMBO, 23(18): 3621-3631, Published Online Aug. 26, 2004.
Hatch et al. "Fat Metabolism in Higher Plants" The Journal of Biological Chemistry, 236(11): 2879-2885, Nov. 11, 1961.
Kebeish "Chloroplastic Photorespiratory Bypass Increases Photosynthesis and Biomass Production in *Arabisopsis thaliana*", Nature Biotechnology, 25(5): 593-599, May 2007.
Levebvre et al. "Increased Sedoheptulose-1,7-Bisphosphatase Activity in Transgenic Tobacco Plants Stimulates Photosynthesis and Growth From an Early Stage in Development", Plant Physiology, 138: 451-460, May 2005.
Lietzan et al. "Functionally Diverse Biotin-Dependent Enzymes With Oxaloacetate Decarboxylase Activity", Archives of Biochemistry and Biophysics, 544: 75-86, Available Online Oct. 30, 2013.
Raines "Increasing Photosynthetic Carbon Assimilation in C3 Plants to Improve Crop Yield: Current and Future Strategies", Plant Physiology, XP002638328, 155(1): 36-42, Jan. 2011.
Raines "Transgenic Approaches to Manipulate the Environmental Responses of the C3 Carbon Fixation Cycle", Plant, Cell and Environment, 29: 331-339, 2006.
Wood et al. "Transcarboxylase, II. Purification and Properties of Methylmalonyl-Oxaloacetic Transcarboxylase", Proc.Natl.Acad. Sci (PNAS), USA, 47(3): 289-303, Mar. 1961.

\* cited by examiner

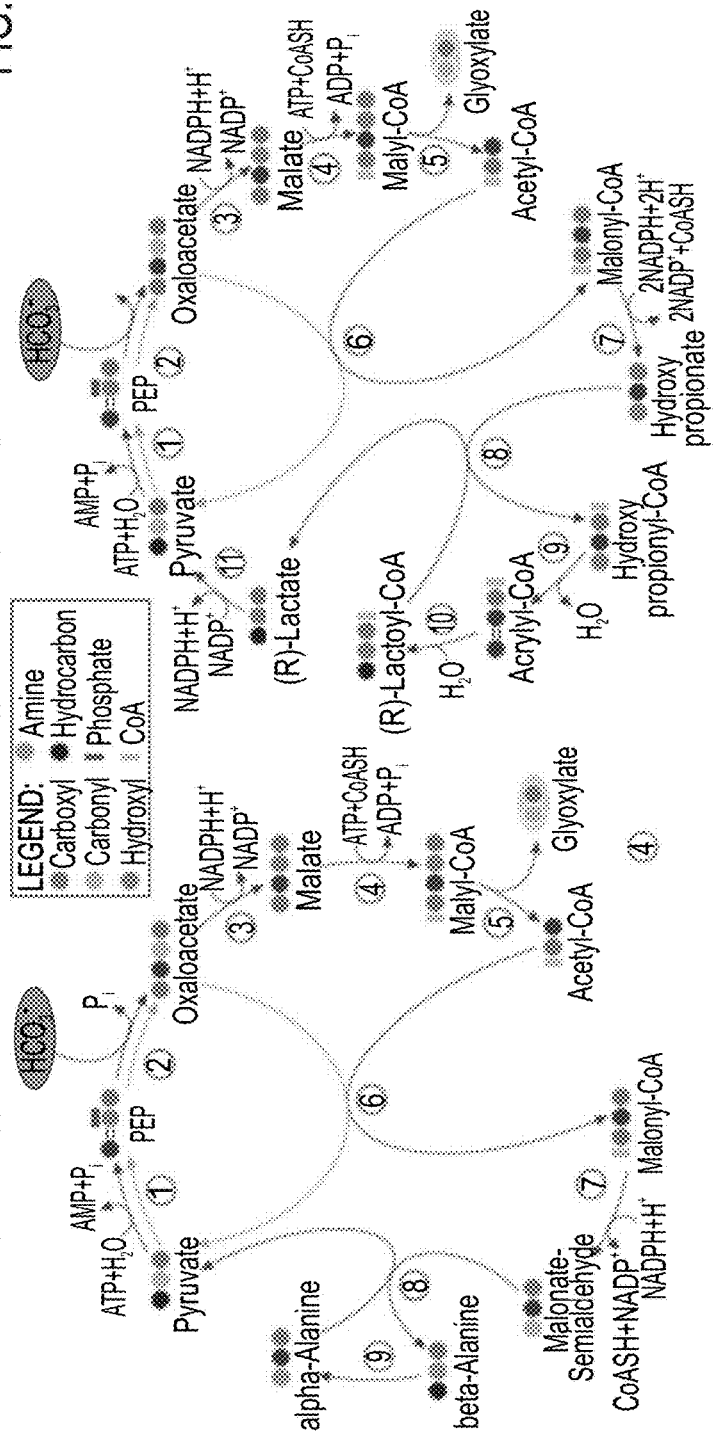

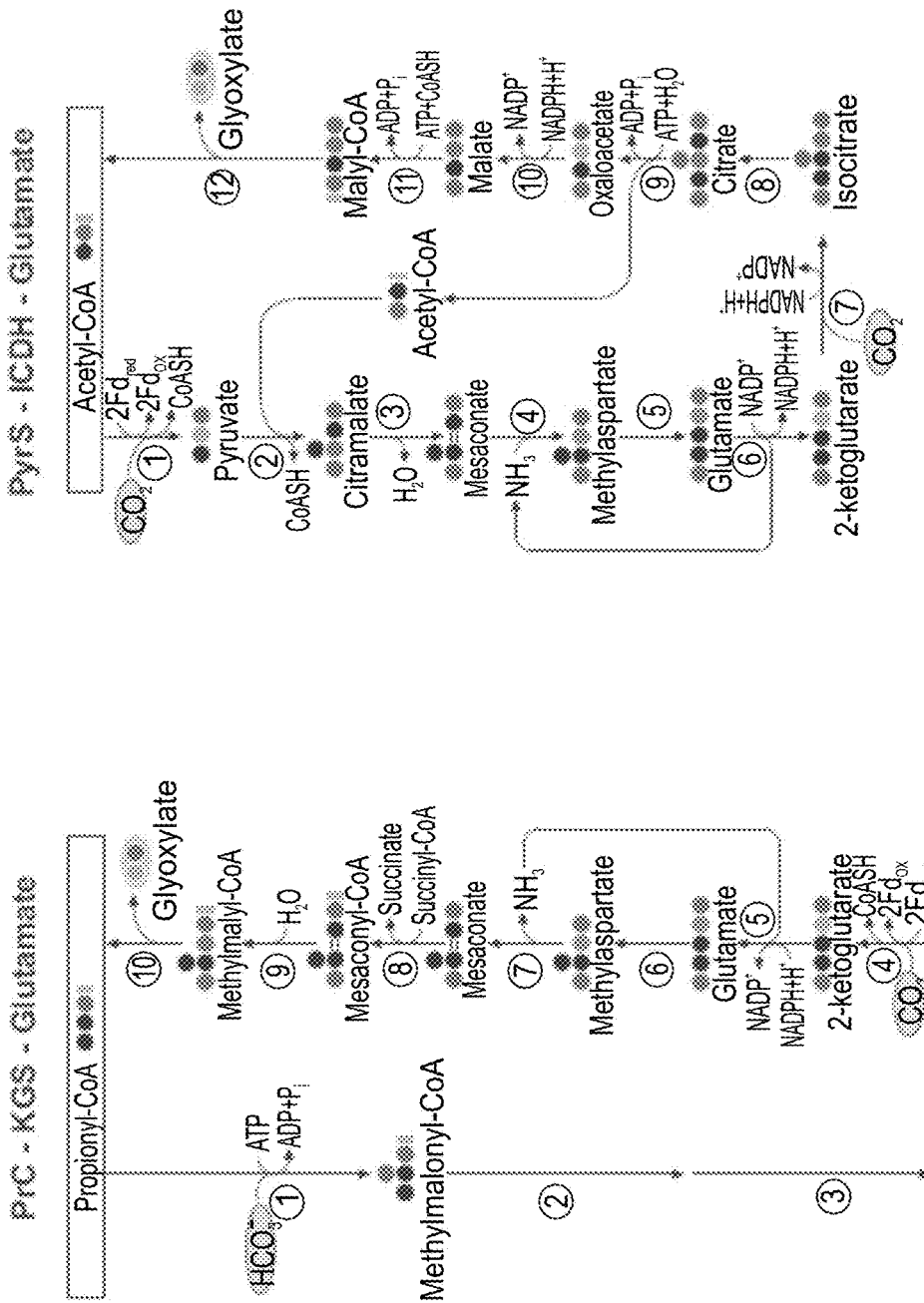

FIG. 12

| Enzyme Name (EC number)* Ordered by EC number | Carbon Species | Km (mM)* for carbon species | Specific Activity* μmol/min/mg (saturating CO₂/HCO₃⁻) | Specific Activity* μmol/min/mg (ambient CO₂/HCO₃⁻) | Co-factors Consumption | Thermodynamically Preferable Direction | Oxygen Sensitivity |
|---|---|---|---|---|---|---|---|
| RUBISCO (4.1.1.39) | CO₂ | 0.01-0.02 | 3.5 (2.7-5) | 1.13 (0.9-1.5) | - | Carboxylation (irreversible) | |
| Malic enzyme (1.1.1.39-40) | CO₂ | 3-13 (HCO₃⁻)* | 17 (4.5-33) | 0.4 (<1) | NADPH + H → NADP | Decarboxylation | |
| Isocitrate dehydrogenase (1.1.1.41-42) | CO₂ | 1.7-3.7 (HCO₃⁻)* | 53 (35-70) | 3.9 (3-4.5) | NADPH + H → NADP | Decarboxylation | |
| Phosphogluconate Dehydrogenase (1.1.1.44) | CO₂ | 15-50 | 0.6 (0.15-1) | <<1 | NADPH + H → NADP | Decarboxylation | |
| Pyruvate NADP+ Oxidoreductase (1.2.1.51) | CO₂ | Not known | NA | NA | NADPH + H → NADP | Decarboxylation | +/- |
| Pyruvate synthase (1.2.7.1) | CO₂ | 3.5 (HCO₃⁻)* / 2-5 (CO₂) | NA | NA | 2Fd_red → 2Fd_ox | Decarboxylation | + |
| 2-Oxobutyrate synthase (1.2.7.2) | CO₂ | Not known | NA | NA | 2Fd_red → 2Fd_ox | Decarboxylation | + |
| 2-Ketoglutarate synthase (1.2.7.3) | CO₂ | Not known | NA | NA | 2Fd_red → 2Fd_ox | Decarboxylation | + |
| 2-ketoisovalerate ferredoxin oxidoreductase (1.2.7.7) | CO₂ | 48 | NA | NA | 2Fd_red → 2Fd_ox | Decarboxylation | + |
| PEP carboxylase (4.1.1.31) | HCO₃⁻ | 0.06-0.2 | 35 (23-52) | 21 (11-30) | - | Carboxylation (irreversible) | |
| PEP carboxykinase (4.1.1.32/38/49) | CO₂ | 3.7-11 (HCO₃⁻)* | 39 (17-72) | 0.8 (0.5-1.4) | ADP → ATP | D/C | |
| Pyruvate carboxylase (6.4.1.1) | HCO₃⁻ | 0.25-2.5 | 32 (26-43) | 54 (3.4-8.4) | ATP → ADP | Carboxylation | |
| Acetyl-CoA carboxylase (6.4.1.2) | HCO₃⁻ | 0.7-1.7 | 18 (7-52) | 4.6 (0.5-20) | ATP → ADP | Carboxylation | |
| Propionyl-CoA carboxylase (6.4.1.3) | HCO₃⁻ | 0.7-1.7 | 30 (14-62) | 3.1 (1.3-8) | ATP → ADP | Carboxylation | |
| Methylcrotonyl-CoA Carboxylase (6.4.1.4) | HCO₃⁻ | 0.8-0.9 | 6 (4-9.5) / 2.1 | 0.8 (<1) / 0.28 | ATP → ADP | Carboxylation | |
| Acetone carboxylase (6.4.1.6) | ? | 2.4-10 (CO₂) | 0.4 (0.2-0.5) | 0.25 (<1) | ATP → AMP | Carboxylation | |
| 2-oxoglutarate carboxylase (6.4.1.7) | HCO₃⁻ | Not known | 15 | ? | ATP → ADP | Carboxylation | |
| Crotonyl-CoA Carboxylase/Reductase | CO₂ | 14 (HCO₃⁻) | 130 | 1.8 | NADPH → NADP | Carboxylation | |
| Methylmalonyl-CoA Carboxytransferase (2.1.3.1) | | | 30-40 (15 for acetyl-CoA carboxylation) | | - | D/C | |

FIG. 13

Enzyme Details

| # | Reaction | Enzyme | EC number | Specific Activity μmol/min/mg | ATP (equivalent) Consumption | NAD(P)H (equivalent) Consumption |
|---|---|---|---|---|---|---|
| 1 | Acetyl-CoA->Malonyl-CoA | Acetyl-CoA Carboxylase | 6.4.1.2 | 18 | 1 | 0 |
| 2 | Malonyl-CoA->Hydroxypropionate | Malonyl-CoA Reductase | 1.1.1.-+1.2.1.- | 10 | 0 | 2 |
| 3 | Hydroxypropionate->Propionyl-CoA | Propionyl/2CoA synthase | 6.2.1.-+4.2.1.-+1.3.1.1- | 4 | 2 | 1 |
| 4 | Propionyl-CoA-> Methylmalonyl-CoA | Propionyl-CoA Carboxylase | 6.4.1.3 | 29.6 | 1 | 0 |
| 5 | Methylmalonyl-CoA epimerase | Methylmalonyl-CoA Epimerase | 5.1.99.1 | 177 | 0 | 0 |
| 6 | Methylmalonyl-CoA-> Succinyl-CoA | Methylmalonyl-CoA Mutase | 5.4.99.2 | 23.5 | 0 | 0 |
| 7 | Acetyl-CoA->Pyruvate | Pyruvate Synthase | 1.2.7.1 |  | 0 | 2 |
| 8 | Pyruvate->PEP | Pyruvate Water (&Phosphate) Dikinases | 2.7.9.2 (&2.7.9.1) | 11.1 | 2 | 0 |
| 9 | Pyruvate->Oxaloacetate | Pyruvate Carboxylase | 6.4.1.1 | 32.4 | 1 | 0 |
| 10 | PEP->Oxaloacetate | PEP Carboxylase | 4.1.1.31 | 35.2 | 0 | 0 |
| 11 | Oxaloacetate-> Malate | Malate Dehydrogenase (NAD/NADP) | 1.1.1.37/82 | 1250 | 0 | 1 |
| 12 | Malate->Oxaloacetate |  |  | 650 | 0 | -1 |
| 13 | Malate->Pyruvate | Malic enzyme | 1.1.1.38,39,40 | 54 | 0 | -1 |
| 14 | Malate->Fumarate | Fumarate Hydratase | 4.2.1.2 | 800 | 0 | 0 |
| 15 | Fumarate-> Malate |  |  | 1975 | 0 | 0 |
| 16 | Fumarate->Succinate | Succinate Dehydrogenase/ Fumarate Reductase | 1.3.5.1/1.3.99.1/1.3.1.6 | 177 | 0 | 1 |
| 17 | Succinate->Fumarate |  |  | 50.8 | 0 | -1 |
| 18 | Succinate->Succinyl-CoA | Succinyl-CoA Synthetase | 6.2.1.45 | 29.5 | 1 | 0 |
| 19 | Succinyl-CoA->Succinate |  |  | 33.5 | -1 | 0 |
| 20 | Malate->Malyl-CoA | Malyl-CoA Synthetase | 6.2.1.9 | 5.4 | 1 | 0 |
| 21 | Succinyl-CoA+Malate->Succinate+Malyl-CoA | Succinate citramalate CoA-transferase | 2.8.3.7 | 7.5 | 0 | 0 |
| 22 | Malyl-CoA->Acetyl-CoA+Glyoxylate | Malyl-CoA Lyase | 4.1.3.24 | 23 | 0 | 0 |
| 23 | Glyoxylate+Acetyl-CoA->Malate | Malate Synthase | 2.3.3.9 | 36.4 | 0 | 0 |
| 24 | Succinyl-CoA->2-Ketoglutarate | 2-Ketoglutarate Synthase | 1.2.7.3 |  | 0 | 2 |
| 25 | 2-Ketoglutarate->Isocitrate | Isocitrate Dehydrogenase | 1.1.1.41/42 | 553.1 | 0 | -1 |
| 26 | Isocitrate->Succinate+Glyoxylate | Isocitrate Lyase | 4.1.3.1 | 24.3 | 0 | 0 |
| 27 | Succinate+Glyoxylate->Isocitrate |  |  | 70 | 0 | 0 |
| 28 | Isocitrate->Citrate | Aconitate Hydratase | 4.2.1.3 | 14.9 | 0 | 0 |
| 29 | Citrate->Isocitrate |  |  | 16.1 | 0 | 0 |
| 30 | Citrate->Acetyl-CoA+Oxaloacetate | ATP Citrate Lyase | 2.3.3.8 | 11.7 | 1 | 0 |
| 31 | Acetyl-CoA+Oxaloacetate->Citrate | Citrate Synthase | 2.3.3.1 | 165 | 0 | 0 |
| 32 | Succinyl-CoA->Succinate-semialdehyde | Succinyl-CoA Reductase | ? | 3.4 | 0 | 2 |
| 33 | Succinate-semialdehyde->4-hydroxybutyrate | 4-Hydroxybutyrate Dehydrogenase | 1.1.1.61 | 2800 | 0 | 1 |
| 34 | 4-Hydroxybutyrate->4-Hydroxybutyryl-CoA | 4-Hydroxybutyryl-CoA Synthetase | ? | ? | 2 | 0 |
| 35 | 4-Hydroxybutyryl-CoA->Crotonyl-CoA | 4-Hydroxybutyryl-CoA Dehydratase | ? | 5 | 0 | 0 |
| 36 | Crotonyl-CoA->3-Hydroxybutyryl-CoA | Enoyl-CoA Hydratase (Crotonase) | 4.2.1.17/4.21.55 | 1900 | 0 | 0 |
| 37 | 3-Hydroxybutyryl-CoA->Crotonyl-CoA |  |  | 608 | 0 | 0 |
| 38 | 3-Hydroxybutyryl-CoA->Acetoacetate | 3-Hydroxybutyryl-CoA Dehydrogenase | 1.1.1.157 | 30 | 0 | -1 |
| 39 | Acetoacetate->3-Hydroxybutyryl-CoA |  |  | 260 | 0 | 1 |
| 40 | Acetoacetate->2 X Acetyl-CoA | Acetyl-CoA C-Acyltransferase | 2.3.1.9/16 | 385 | 0 | 0 |
| 41 | 2 X Acetyl-CoA->Acetoacetate |  |  | 20 | 0 | 0 |
| 42 | Propionyl-CoA+Glyoxylate->Methylmalyl-CoA | Methylmalyl-CoA Lyase | 4.1.3.24 | 15 | 0 | 0 |
| 43 | Methylmalonyl-CoA->Mesaconyl-CoA | Mesaconyl-CoA Hydratase | ? | 1350 | 0 | 0 |
| 44 | Mesaconyl-CoA->Citramalate | UN-KNOWN | UN-KNOWN | UN-KNOWN | 0 | 0 |
| 45 | Citramalate+Suc-CoA->Citramalyl-CoA+Suc | Succinate Citramalate CoA-Transferase | 2.8.3.7 | 17.5 | 0 | 0 |
| 46 | Citramalyl-CoA->Pyruvate+Acetyl-CoA | Citramalyl-CoA Lyase | 4.1.3.25 | 15 | 0 | 0 |
| 47 | Citramalate->Pyruvate+Acetate | Citramalate Lyase | 4.1.3.22 | 335 | 0 | 0 |
| 48 | Acetate+Suc-CoA->Acetyl-CoA+Suc | Acetate Succinate CoA-Transferase | 2.8.3.8 | 120 | 0 | 0 |

FIG. 14

| # | Reaction | Enzyme | EC Number | | | |
|---|---|---|---|---|---|---|
| 49 | Acetyl-CoA+Hydroxypropionate->Hydroxypropionyl-CoA+Acetate | Propionate CoA-transferase | 2.8.3.1 | 10 | 1 | 0 |
| 50 | Hydroxypropionyl-CoA->Acrylyl-CoA | Enoyl-CoA Hydratase (Crotonase) | 4.2.1.17 | 50 | 0 | 0 |
| 51 | Acrylyl-CoA->(R)-Lactoyl-CoA | Lactoyl-CoA Dehydratase | 4.2.1.54 | 170 | 0 | 0 |
| 52 | (R)-Lactoyl-CoA+Acetate->(R)-Lactate+Acetyl-CoA | Propionate CoA-Transferase | 2.8.3.1 | 30 | -1 | 0 |
| 53 | (R)-Lactate->Pyruvate | Lactate Dehydrogenase | 1.1.1.28 | 150 | 0 | -1 |
| 54 | Propionyl-CoA+Glyoxylate->Hydroxyglutarate | 2-Hydroxyglutarate Synthase | 2.3.3.11 | ? | 0 | 0 |
| 55 | Crotonyl-CoA->Glutaconyl-CoA | Methylcrotonyl-CoA Carboxylase | 6.4.1.4 | 2.1 | 1 | 0 |
| 56 | Glutaconyl-CoA->(R)-2-Hydroxyglutaryl-CoA | (R)-2-Hydroxyglutaryl-CoA Dehydratase | 4.2.1.- | 31.4 | 0 | 0 |
| 57 | Acetate+(R)-Hydroxyglutaryl-CoA->Acetyl-CoA+Hydroxyglutarate | Glutaconate CoA-Transferase | 2.8.3.12 | 50 | -1 | 0 |
| 58 | (R)-Hydroxyglutarate->α-Ketoglutarate | 2-Hydroxyglutarate Dehydrogenase | 1.1.99.2 | 100 | 0 | -1 |
| 59 | Crotonyl-CoA->Ethylmalonyl-CoA | Crotonyl-CoA Carboxylase/Reductase | ? | 130 | 0 | 1 |
| 60 | Ethylmalonyl-CoA isomeration | Ethylmalonyl-CoA Epimerase | ? | 110 | 0 | 0 |
| 61 | Ethylmalonyl-CoA->Methylsuccinyl-CoA | Ethylmalonyl-CoA Mutase | ? | ? | 0 | 0 |
| 62 | Methylsuccinyl-CoA->Mesaconyl-CoA | Methylsuccinyl-CoA Dehydrogenase | ? | ? | 0 | -1 |
| 63 | 2 X Glyoxylate->Tartronate-Semialdehyde | Glyoxylate Carboligase | 4.1.1.47 | 16.5 | 0 | 0 |
| 64 | Tartronate-Semialdehyde->Glycerate | Tartronate-Semialdehyde Reductase | 1.1.1.60 | 107 | 0 | 1 |
| 65 | Glycerate->Glycerate-3-Phosphate | Glycerate Kinase | 2.7.1.31 | 240 | 1 | 0 |
| 66 | Glycerate-3-Phosphate->Glycerate-biphosphate | Phosphoglycerate Kinase | 2.7.2.3 | 760 | 1 | 0 |
| 67 | Glycerate-biphosphate->Glyceraldehyde-3-P | Glyceraldehyde-3P Dehydrogenase (Phosphorylating) | 1.2.1.12-13 | 145 | 0 | 1 |
| 68 | PEP->Glycerate-2-Phosphate | Enolase | 4.2.1.11 | 43 | 0 | 0 |
| 69 | Glycerate-2-Phosphate->Glycerate-3-Phosphate | Phosphoglycerate Mutase | 5.4.2.1 | 415 | 0 | 0 |
| 70 | Glyceraldehyde-3-P->Dihydroxyacetone-P | Triose-Phosphate Isomerase | 5.3.1.1 | 9030 | 0 | 0 |
| 71 | Glyceraldehyde-3-P+Dihydroxyacetone-P->Fructose-1,6-Biphosphate | Fructose-Bisphosphate Aldolase | 4.1.2.13 | 29.5 | 0 | 0 |
| 72 | Fructose-1,6-BP->Fructose-6-Phosphate | Fructose-Bisphosphatase | 3.1.3.11 | 68 | 0 | 0 |
| 73 | Fructose-6-Phosphate+Glyceraldehyde-3P->Erythrose-4-P+Xylulose-5-P | Transketolase | 2.2.1.1 | 58.9 | 0 | 0 |
| 74 | Erythrose-4-P+Dihydroxyacetone-P->Sedoheptulose-1,7-diphosphate | Fructose-Bisphosphate Aldolase | 4.1.2.13 | 11.8 | 0 | 0 |
| 75 | Sedoheptulose-1,7-BP->Sedoheptulose-7-P | Sedoheptulose-Bisphosphatase | 3.1.3.37 | 25.2 | 0 | 0 |
| 76 | Sedoheptulose-7-P+Glyceraldehyde-3-P->Xylulose-5-P+Ribose-5-P | Transketolase | 2.2.1.1 | 22.4 | 0 | 0 |
| 77 | Ribose-5-P->Ribulose-5-P | Ribose-5-Phosphate Isomerase | 5.3.1.6 | 1850 | 0 | 0 |
| 78 | Xylulose-5-P->Ribulose-5-P | Ribulose-Phosphate 3-Epimerase | 5.1.3.1 | 1200 | 0 | 0 |
| 79 | Ribulose-5-P->Ribulose-1,5-BiPhosphate | Phosphoribulokinase | 2.7.1.19 | 335 | 1 | 0 |
| 80 | Ribulose-1,5-BP->2 X Glycerate-3 Phosphate | Ribulose-Bisphosphate Carboxylase | 4.1.1.39 | 3.5 | 0 | 0 |
| 81 | Ribulose-1,5-BP->1.5 X Glycerate-3 Phosphate | | | 0.92 | 1 | 0.5 |
| 82 | Malonyl-CoA->Malonate-Semialdehyde | Malonyl-CoA Reductase | 1.2.1.- | 10 | 0 | 1 |
| 83 | Malonate-Semialdehyde+Alanine->beta-Alanine+Pyruvate | beta-Alanine-Pyruvate Transaminase | 2.6.1.18 | 10 | 0 | 0 |
| 84 | beta-Alanine->Alanine | Alanine-Aminomutase | ? | ? | 0 | 0 |
| 85 | 2-Ketoglutarate+Aspartate->Glutamate+Oxaloacetate | Aspartate Transaminase | 2.6.1.1 | 290 | 0 | 0 |
| 86 | Glutamate->Methylaspartate | Glutamate Mutase | 5.4.99.1 | 10 | 0 | 0 |
| 87 | Methylaspartate->Mesaconate+NH3 | Methylaspartate Ammonia-Lyase | 4.3.1.2 | 300 | 0 | 0 |
| 88 | Mesaconate->Citramalate | 2-Methylmalate Dehydratase | 4.2.1.34 | 10 | 0 | 0 |
| 89 | Fumarate+NH3->Aspartate | Aspartate Ammonia-Lyase | 4.3.1.1 | 250 | 0 | 0 |

FIG. 14 continued

| 90 | Methmalyl-CoA->Propiony-CoA+Glyoxylate | Methylmalyl-CoA Lyase | 4.1.3.24 | 6.1 | 0 | 0 |
|---|---|---|---|---|---|---|
| 91 | Mesaconyl-CoA->Methylmalyl-CoA | Mesaconyl-CoA Hydratase | ? | 1350 | 0 | 0 |
| 92 | Mesaconate->Mesaconyl-CoA | UN-KNOWN | UN-KNOWN | UN-KNOWN | 0 | 0 |
| 93 | 2-Ketoglutarate+NH3->Glutamate | Glutamate Dehydrogenase (NADPH) | 1.4.1.4 | 300 | 0 | 1 |
| 94 | Oxaloacetate->Oxalate+Acetate | Oxaloacetase | 3.7.1.1 | 34 | 0 | 0 |
| 95 | Oxalate->Oxalyl-CoA | Oxalate CoA Ligase | 6.2.1.8 | ? | 2 | 0 |
| 96 | Oxalyl-CoA->Glyoxylate | Glyoxylate Dehydrogenase | 1.2.1.17 | 10 | 0 | 1 |
| 97 | Pyruvate->Malate | Malic Enzyme | 1.1.1.38,39,40 | 17.2 | 0 | 1 |
| 98 | Acetyl-CoA+Oxaloacetate->Malonyl-CoA+Pyruvate | Methylmalonyl-CoA Carboxytransferase | 2.1.3.1 | 15 | 0 | 0 |
| 99 | 2-Ketoglutarate->Oxalosuccinate | 2-Ketoglutarate Carboxylase | 6.4.1.7 | UN-KNOWN | 1 | 0 |
| 100 | Oxalosuccinate->Isocitrate | Isocitrate Dehydrogenase | 1.1.1.41/42 | UN-KNOWN | 0 | 1 |
| 101 | Glyoxylate->Glycine | Glycine Dehydrogenase | 1.4.1.10 | 5.6 | 0 | 1 |
| 102 | Glyoxylate+Glycine->3-Hydroxyaspartate | 3-Hydroxyaspartate Aldolase | 4.1.3.14 | UN-KNOWN | 0 | 0 |
| 103 | 3-Hydroxyaspartate->Oxaloacetate | 3-Hydroxyaspartate Dehydratase | 4.3.1.16 | 50 | 0 | 0 |
| 104 | Glycine->Acetyl-Phosphate | Glycine Reductase | 1.21.4.2 | 200 | 0 | 0 |
| 105 | Acetyl-Phosphate->Acetyl-CoA | Phosphate Acetyltransferase | 2.3.1.8 | 3000 | 0 | 1 |
| 106 | Propiony-CoA+Oxaloacetate->Methylcitrate | 2-Methylcitrate Synthase | 2.3.3.5 | 14 | 0 | 0 |
| 107 | Methylcitrate->Methylaconitate | 2-Methylcitrate Dehydratase | 4.2.1.79 | 8 | 0 | 0 |
| 108 | Methylaconitate->Methylisocitrate | 2-Methylisocitrate Dehydratase | 4.2.1.99 | 1.7 | 0 | 0 |
| 109 | Methylisocitrate->Succinate+Pyruvate | Methylisocitrate Lyase | 4.1.3.30 | 40 | 0 | 0 |

FIG. 14 continued

ENZYMATIC SYSTEMS FOR CARBON FIXATION AND METHODS OF GENERATING SAME

RELATED APPLICATIONS

This application is a division of U.S. patent application Ser. No. 13/576,720 filed on Aug. 2, 2012, which is a National Phase of PCT Patent Application No. PCT/IL2011/000145 having International Filing Date of Feb. 10, 2011, which claims the benefit of priority of U.S. Provisional Patent Application No. 61/303,338 filed on Feb. 11, 2010. The contents of the above applications are all incorporated by reference as if fully set forth herein in their entirety.

FIELD AND BACKGROUND OF THE INVENTION

The present invention relates to enzymatic systems for carbon fixation and methods of generating same.

Photosynthesis is a process executed by photosynthetic organisms by which, inorganic carbon (Ci), such as $CO_2$ and $HCO_3$, is incorporated into organic compounds using the energy of photon radiation. Photosynthetic organisms, such as, soil-grown and aquatic plants and cyanobacteria (blue-green algae), depend on the organic compounds produced via photosynthesis for sustenance and growth.

In the process of transforming sunlight into biological matter, plants absorb ten times more carbon dioxide from the atmosphere than is emitted by the global human population. Moreover, agriculture, which is dependent on carbon fixation, consumes over 70% of the fresh water utilized by humanity and the majority of cultivatable land resources on earth. These figures point to the central place that carbon fixation by plants plays in our global ecological footprint. In nature the growth limiting factors of photosynthetic organisms vary between habitats and often include the availability of water, light, fixed nitrogen, iron and phosphorous. However, under human cultivation the usage of fertilizers and irrigation can make the carbon fixation rate limiting; for example, various C3 plants have shown a significant increase in growth rate when exposed to twice the atmospheric $CO_2$ concentration.

Previous growth enhancements have been demonstrated by addressing several biochemical limiting factors, related both to the light-dependent and light-independent reactions. For example, transgenic *Arabidopsis* plants that expressed an efficient bacterial photorespiration pathway, instead of their natural photorespiration pathway, grew faster, produced more shoot and root biomass, and contained more soluble sugars [Kebeish R, et al. (2007) Chloroplastic photorespiratory bypass increases photosynthesis and biomass production in *Arabidopsis thaliana*. *Nat Biotechnol* 25(5): 593-599]. In another effort, tobacco plants overexpressing sedoheptulose-1,7-bisphosphatase, an enzyme operating in the reductive pentose phosphate cycle (rPP, also known as the Calvin-Benson Cycle), were characterized by an increased photosynthetic rate and a 30% enhancement in biomass yield [Lefebvre S, et al. (2005) Increased sedoheptulose-1,7-bisphosphatase activity in transgenic tobacco plants stimulates photosynthesis and growth from an early stage in development. *Plant Physiol* 138(1):451-460].

The rPP cycle (FIG. 5A), used by the vast majority of autotrophic organisms for $CO_2$ assimilation, is limited by the slow rate of Rubisco (Ribulose-1,5-bisphosphate carboxylase/oxygenase). The inverse correlation between the enzyme turnover number ($\sim$2-4 s$^{-1}$) and its $CO_2$ specificity indicates that the enzyme might already be naturally optimized. Therefore, further optimization of Rubisco may prove difficult and lead to only marginal results [Raines C A (2006) Transgenic approaches to manipulate the environmental responses of the C3 carbon fixation cycle. *Plant Cell Environ* 29(3):331-339] thereby limiting the potential for increasing the rate of the rPP cycle. Designing and developing alternative (Rubisco independent) pathways that can support carbon fixation with a higher rate can therefore be highly beneficial.

To date, five natural metabolic pathways have been identified that are capable of performing carbon fixation in place of the classic rPP cycle. These are the reductive tri-carboxylic-acid (rTCA) cycle, postulated in the 60's; the oxygen sensitive reductive acetyl-CoA (rAcCoA) pathway; the extensively researched 3-hydroxypropionate (3-HP) cycle; the 3-hydroxypropionate/4-hydroxybutyrate (3-HP/4-HB) cycle and the recently discovered dicarboxylate/4-hydroxybutyrate (DC/4-HB) cycle.

SUMMARY OF THE INVENTION

According to an aspect of some embodiments of the present invention there is provided a system for carbon fixation, comprising enzymes which catalyze reactions of a carbon fixation pathway, wherein at least one of the reactions of the carbon fixation pathway is a carboxylation reaction, wherein products of the reactions of the carbon fixation pathway comprise oxaloacetate and malonyl-CoA, wherein an enzyme which performs the carboxylation reaction is selected from the group consisting of phophoenolpyruvate (PEP) carboxylase, pyruvate carboxylase and acetyl-CoA carboxylase and wherein an additional product of the carbon fixation pathway is glyoxylate.

According to some embodiments of the invention, the glyoxylate is the export product.

According to some embodiments of the invention, pyruvate is the export product.

According to some embodiments of the invention, the enzymes of the carbon fixation pathway generate more than 0.3 μmol glyceraldehyde-3-phosphate/min/mg.

According to some embodiments of the invention, the enzyme which performs the carboxylation enzyme is PEP carboxylase.

According to some embodiments of the invention, at least two of the reactions of the carbon fixation pathway are carboxylation reactions.

According to some embodiments of the invention, one of the reactions of the carbon fixation pathway is a transcarboxylation reaction.

According to some embodiments of the invention, the enzyme which performs the transcarboxylation reaction is methylmalonyl-CoA carboxytransferase.

According to some embodiments of the invention, the products of the reactions of the carbon fixation pathway further comprise pyruvate, phophoenolpyruvate (PEP), malate, malyl CoA and acetyl CoA.

According to some embodiments of the invention, the system is expressed in cells.

According to some embodiments of the invention, the system is expressed in eukaryotic cells.

According to some embodiments of the invention, the system is expressed in prokaryotic cells.

According to some embodiments of the invention, the system is present in a reactor.

According to some embodiments of the invention, the cells are selected from the group consisting of bacteria cells, algae cells and higher plant cells.

According to some embodiments of the invention, the bacteria cells are *E. coli* cells.

According to some embodiments of the invention, the bacteria cells express Pyruvate Dikinase, PEP Carboxylase, Malate Dehyderogenase, Lactate Dehydrogenase, Glyoxylate Carboligase, Tartronate-Semialdehyde Reductase, Glycerate Kinase, Malyl-CoA Synthetase, Malyl-CoA Lyase, Methlmalonyl-CoA Carboxytransferase, Malonate Semialdehyde Dehydrogenase, Alanine Aminomutase and Beta-Alanine Pyruvate Transaminase.

According to some embodiments of the invention, the bacteria cells express Pyruvate Dikinase, PEP Carboxylase, Malate Dehyderogenase, Lactate Dehydrogenase, Glyoxylate Carboligase, Tartronate-Semialdehyde Reductase, Glycerate Kinase, Malyl-CoA Synthetase, Malyl-CoA Lyase, Methlmalonyl-CoA Carboxytransferase, Malonyl-CoA Reductase, Propionate CoA Transferase, Enoyl-CoA Hydratase and Lactoyl-CoA dehydratase.

According to some embodiments of the invention, the bacteria cells further express NAD$^+$-dependent formate dehydrogenase or NAD:phosphite oxidoreductase.

According to some embodiments of the invention, the Malate Dehydrogenase is a higher plant Malate dehydrogenase.

According to some embodiments of the invention, the lactate Dehydrogenase is a trichomona lactate dehydrogenase.

According to some embodiments of the invention, the bacteria cells are cyanobacteria cells.

According to some embodiments of the invention, the cyanobacterial cells express Pyruvate Dikinase, PEP Carboxylase, Malate Dehyderogenase, lactate dehydrogenase, Glyoxylate Carboligase, Tartronate-Semialdehyde Reductase and Glycerate Kinase, Malyl-CoA Synthetase, Malyl-CoA Lyase, Methlmalonyl-CoA Carboxytransferase, Malonate Semialdehyde Dehydrogenase, Alanine Aminomutase and Beta-Alanine Pyruvate Transaminase.

According to some embodiments of the invention, the cyanobacterial cells express Pyruvate Dikinase, PEP Carboxylase, Malate Dehyderogenase, lactate dehydrogenase, Glyoxylate Carboligase, Tartronate-Semialdehyde Reductase and Glycerate Kinase, Malyl-CoA Synthetase, Malyl-CoA Lyase, Methlmalonyl-CoA Carboxytransferase, Malonyl-CoA Reductase, Propionate CoA Transferase, Enoyl-CoA Hydratase and Lactoyl-CoA dehydratase.

According to some embodiments of the invention, the Malate Dehydrogenase is a higher plant Malate dehydrogenase.

According to some embodiments of the invention, the lactate Dehydrogenase is a trichomona lactate dehydrogenase.

According to some embodiments of the invention, the algae cells are *Chlamydomonas reinhardtii* cells.

According to some embodiments of the invention, the *Chlamydomonas reinhardtii* cells express PEP Carboxylase, Malate Dehyderogenase, Glycerate Kinase, Pyruvate Dikinase, Malyl-CoA Synthetase, Malyl-CoA Lyase, Methlmalonyl-CoA Carboxytransferase, Malonate Semialdehyde Dehydrogenase, Alanine Aminomutase, Beta-Alanine Pyruvate Transaminase, Glyoxylate Carboligase and Tartronate-Semialdehyde Reductase.

According to some embodiments of the invention, the *Chlamydomonas reinhardtii* cells express PEP Carboxylase, Malate Dehyderogenase, Glycerate Kinase, Pyruvate Dikinase, Malyl-CoA Synthetase, Malyl-CoA Lyase, Methlmalonyl-CoA Carboxytransferase, Malonyl-CoA Reductase, Propionate CoA Transferase, Enoyl-CoA Hydratase, Lactoyl-CoA dehydratase, Lactate Dehydrogenase, Glyoxylate Carboligase and Tartronate-Semialdehyde Reductase.

According to some embodiments of the invention, the higher plant cell is a tobacco cell.

According to some embodiments of the invention, the tobacco cells express Pyruvate Dikinase, PEP Carboxylase, Malate Dehyderogenase, Glycerate Kinase, Malyl-CoA Synthetase, Malyl-CoA Lyase, Methlmalonyl-CoA Carboxytransferase, Malonate Semialdehyde Dehydrogenase, Alanine Aminomutase, Beta-Alanine Pyruvate Transaminase, Glyoxylate Carboligase and Tartronate-Semialdehyde Reductase.

According to some embodiments of the invention, the tobacco cells express Pyruvate Dikinase, PEP Carboxylase, Malate Dehyderogenase, Glycerate Kinase, Malyl-CoA Synthetase, Malyl-CoA Lyase, Methlmalonyl-CoA Carboxytransferase, Malonyl-CoA Reductase, Propionate CoA Transferase, Enoyl-CoA Hydratase, Lactoyl-CoA dehydratase, Lactate Dehydrogenase, Glyoxylate Carboligase and Tartronate-Semialdehyde Reductase.

According to some embodiments of the invention, the system further comprises an electron donor.

According to some embodiments of the invention, the electron donor is selected from the group consisting of ATP, NADH and NADPH.

According to some embodiments of the invention, the system is in a particle selected from the group consisting of polymeric particles, microcapsules liposomes, microspheres, microemulsions, nano-plates, nanoparticles, nanocapsules and nano spheres.

According to some embodiments of the invention, the enzymes are encapsulated within the particle.

According to some embodiments of the invention, the enzymes are embedded within the particle.

According to some embodiments of the invention, the enzymes are adsorbed on a surface of the particle.

According to an aspect of some embodiments of the present invention there is provided a method of generating a system of one embodiment of the present invention, the method comprising expressing in the bacteria Malyl-CoA Synthetase, Malyl-CoA Lyase, Methlmalonyl-CoA Carboxytransferase, Malonate Semialdehyde Dehydrogenase, Alanine Aminomutase and Beta-Alanine Pyruvate Transaminase, thereby generating the system of one embodiment of the present invention.

According to some embodiments of the invention, the Malyl-CoA Synthetase, Malyl-CoA Lyase, Methlmalonyl-CoA Carboxytransferase, Malonate Semialdehyde Dehydrogenase, Alanine Aminomutase and Beta-Alanine Pyruvate Transaminase are prokaryotic.

According to an aspect of some embodiments of the present invention there is provided a method of generating a system of one embodiment of the present invention, the method comprising expressing in the bacteria Malyl-CoA Synthetase, Malyl-CoA Lyase, Methlmalonyl-CoA Carboxytransferase, Malonyl-CoA Reductase, Propionate CoA Transferase, Enoyl-CoA Hydratase and Lactoyl-CoA dehydratase, thereby generating the system of one embodiment of the present invention.

According to some embodiments of the invention, the method further comprises expressing in the bacteria a higher plant malate dehydrogenase and a Trichomona lactate dehydrogenase.

According to some embodiments of the invention, the method further comprises expressing in the bacteria NAD+-dependent formate dehydrogenase or NAD:phosphite oxidoreductase.

According to an aspect of some embodiments of the present invention there is provided a method of generating a system of one embodiment of the present invention, the method comprising expressing in the bacteria Malyl-CoA Synthetase, Malyl-CoA Lyase, Methlmalonyl-CoA Carboxytransferase, Malonate Semialdehyde Dehydrogenase, Alanine Aminomutase and Beta-Alanine Pyruvate Transaminase, thereby generating the system of one embodiment of the present invention.

According to an aspect of some embodiments of the present invention there is provided a method of generating the system of one embodiment of the present invention, the method comprising expressing in the bacteria Malyl-CoA Synthetase, Malyl-CoA Lyase, Methlmalonyl-CoA Carboxytransferase, Malonyl-CoA Reductase, Propionate CoA Transferase, Enoyl-CoA Hydratase and Lactoyl-CoA dehydratase, thereby generating the system of thereby generating the system of one embodiment of the present invention.

According to some embodiments of the invention, the method further comprises expressing in the bacteria Lactate Dehydrogenase.

According to some embodiments of the invention, the lactate dehydrogenase is a Trichomona lactate dehydrogenase.

According to some embodiments of the invention, the method further comprises expressing in the bacteria a higher plant Malate Dehydrogenase.

According to an aspect of some embodiments of the present invention there is provided a method of generating the system of one embodiment of the present invention comprising expressing enzymes in the cell, the enzymes being PEP Carboxylase, Malate Dehydrogenase, Glycerate Kinase, Pyruvate Dikinase, Malyl-CoA Synthetase, Malyl-CoA Lyase, Methlmalonyl-CoA Carboxytransferase, Malonate Semialdehyde Dehydrogenase, Alanine Aminomutase, Beta-Alanine Pyruvate Transaminase, Glyoxylate Carboligase and Tartronate-Semialdehyde Reductase, wherein the enzymes are targeted to the chloroplast, thereby generating the system of thereby generating the system of one embodiment of the present invention.

According to an aspect of some embodiments of the present invention there is provided a method of generating the system of one embodiment of the present invention comprising expressing enzymes in the cell, the enzymes being PEP Carboxylase, Malate Dehydrogenase, Glycerate Kinase, Pyruvate Dikinase, Malyl-CoA Synthetase, Malyl-CoA Lyase, Methlmalonyl-CoA Carboxytransferase, Malonyl-CoA Reductase, Propionate CoA Transferase, Enoyl-CoA Hydratase, Lactoyl-CoA dehydratase, Lactate Dehydrogenase, Glyoxylate Carboligase and Tartronate-Semialdehyde Reductase, wherein the enzymes are targeted to the chloroplast, thereby generating the system of thereby generating the system of one embodiment of the present invention.

According to an aspect of some embodiments of the present invention there is provided a method of generating the system of one embodiment of the present invention, the method comprising expressing in the cells enzymes, the enzymes being Pyruvate Dikinase, PEP Carboxylase, Malate Dehyderogenase, Glycerate Kinase, Malyl-CoA Synthetase, Malyl-CoA Lyase, Methlmalonyl-CoA Carboxytransferase, Malonate Semialdehyde Dehydrogenase, Alanine Aminomutase, Beta-Alanine Pyruvate Transaminase, Glyoxylate Carboligase and Tartronate-Semialdehyde Reductase, wherein the enzymes are targeted to the chloroplast, thereby generating the system of one embodiment of the present invention.

According to an aspect of some embodiments of the present invention there is provided a method of generating the system of one embodiment of the present invention, the method comprising expressing in the cells enzymes, the enzymes being Pyruvate Dikinase, PEP Carboxylase, Malate Dehyderogenase and Glycerate Kinase, Malyl-CoA Synthetase, Malyl-CoA Lyase, Methlmalonyl-CoA Carboxytransferase, Malonyl-CoA Reductase, Propionate CoA Transferase, Enoyl-CoA Hydratase, Lactoyl-CoA dehydratase, Lactate Dehydrogenase, Glyoxylate Carboligase and Tartronate-Semialdehyde Reductase wherein the enzymes are targeted to the chloroplast, thereby generating the system of one embodiment of the present invention.

According to an aspect of some embodiments of the present invention there is provided a system for carbon fixation, as exemplified in FIGS. 7A-G and 9A-N.

According to an aspect of some embodiments of the present invention there is provided an autotrophic *E. coli* expressing enzymes of the Calvin-Benson cycle.

According to some embodiments of the invention, the autotrophic *E. coli* express phosphoribulokinase and Ribulose-Bisphosphate Carboxylase.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
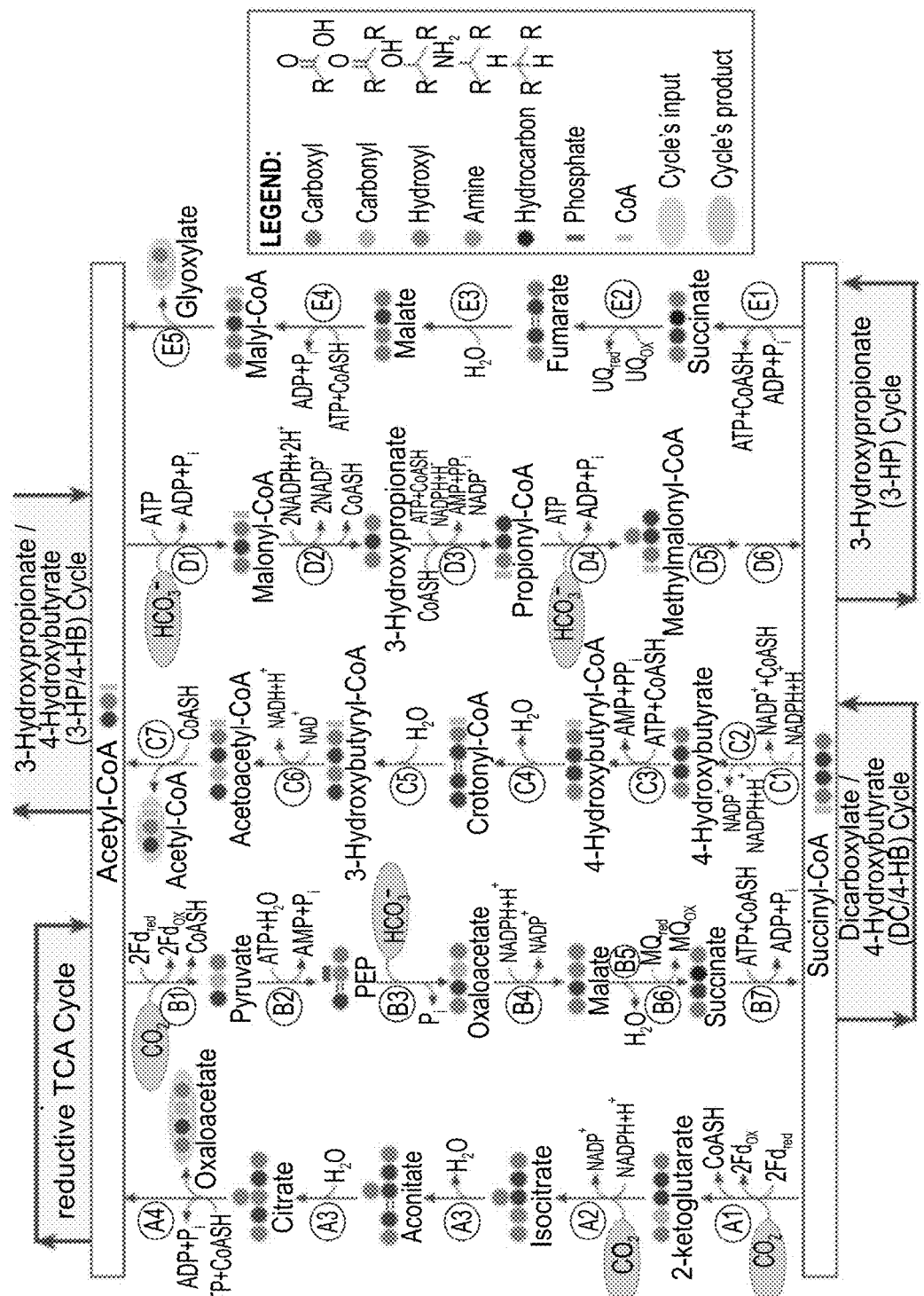

FIG. 1 is a diagram illustrating natural carbon fixation pathways. Shown is the variety and interrelationships of four of the five alternatives to the Calvin Benson cycle. A fifth option, the reductive acetyl-CoA pathway is not shown. A color notation has been used to display the different functional groups composing the metabolites, which also corresponds to the oxidation states of the carbons: red circles indicate carboxyl, purple corresponds to carbonyl, green to hydroxyl, azure to amine and black to hydrocarbon. The '=' mark symbolizes a double bond. UQ and MQ correspond to ubiquinone and menaquinone, respectively.

Enzymes: (A1) 2-Ketoglutarate Synthase; (A2) Isocitrate Dehydrogenase; (A3) Aconitate Hydratase; (A4) ATP Citrate Lyase; (B1) Pyruvate Synthase; (B2) Pyruvate Water (Phosphate) Dikinase; (B3) PEP Carboxylase; (B4) Malate Dehydrogenase; (B5) Fumarate Hydratase; (B6) Fumarate Reductase; (B7) Succinyl-CoA Synthetase; (C1) Succinyl-CoA Reductase; (C2) 4-Hydroxybutyrate Dehydrogenase; (C3) 4-Hydroxybutyryl-CoA Synthetase; (C4) 4-Hydroxybutyryl-CoA Dehydratase; (C5) Enoyl-CoA Hydratase (Crotonase); (C6) 3-Hydroxybutyryl-CoA Dehydrogenase; (C7) Acetyl-CoA C-Acyltransferase; (D1) Acetyl-CoA Carboxylase (D2) Malonyl-CoA Reductase; (D3) Propionyl-CoA synthase; (D4) propionyl-CoA Carboxylase; (D5) Methylmalonyl-CoA Epimerase; (D6) Methylmalonyl-CoA Mutase; (E1) Succinyl-CoA Synthetase; (E2) Succinate Dehydrogenase; (E3) Fumarate Hydratase; (E4) Malyl-CoA Synthetase and (E5) Malyl-CoA Lyase. E.C. numbers are given in Example 2.

FIGS. 2A-2C are diagrams illustrating thermodynamic constraints on carbon fixation. The minimal number of ATP molecules that should be hydrolyzed to ensure that carbon fixation would be thermodynamically feasible. The cycle's product was assumed to be GA3P. Different electron donors alternatives are analyzed at varying conditions of pH, ionic strength and under ambient $CO_2^{gas}$ concentration (390 ppm). (A) all 6 of the electron donors are NAD(P)H, as in the case of the reductive pentose phosphate pathway. (B) two of the electron donors are ferredoxins, one is menaquinone (MQ) and the other three are NAD(P)H, as in the case of the rTCA cycle, where MQ is the electron donor for fumarate reductase (other electron donors are shown in FIG. 1B). (C) Two of the electron donors are ferredoxins (Fd) and the other four are NAD(P)H, as in the case of the rAcCoA pathway. Bold lines (right and middle schemes) correspond to the feasibility ranges of the pathways, as dictated by their actual ATP consumption (5 ATP molecules by the rTCA cycle and 4 by the rAcCoA pathway). The pathways are not feasible at pH and ionic strength values corresponding to the areas to the right of those lines; the ATP requirement in those areas is higher than that consumed by the pathways. The rPP cycle consumes 9 ATP molecules, well above the minimal thermodynamic requirement. See Example 2 for further details and calculations.

Figure 3:
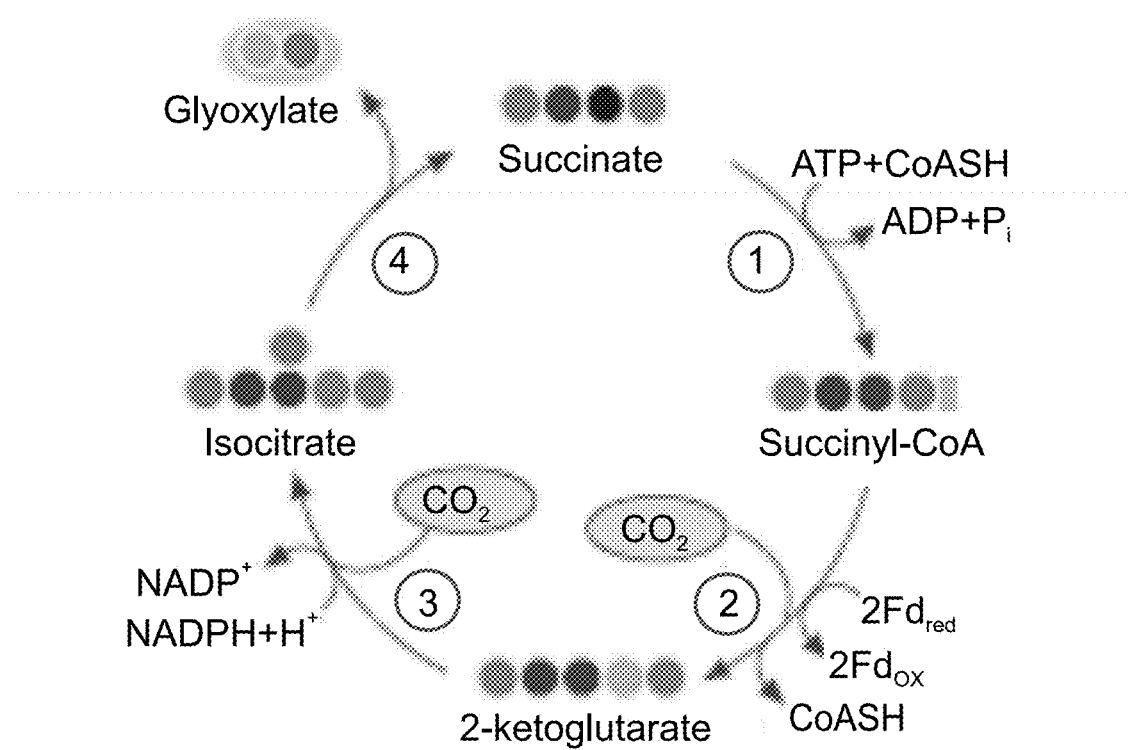

FIG. 3 is a diagram of the shortest possible carbon fixation cycle—a 'metabolic shortcut' of the rTCA cycle. Two $CO_2$ molecules are fixed to give a two carbon oxalate product as the cycle product. Every circle denotes carbon atom. A color notation has been used to display the different functional groups composing the metabolites, which also corresponds to the oxidation states of the carbons: red circles indicate carboxyl, purple corresponds to carbonyl, green to hydroxyl, azure to amine and black to hydrocarbon. The '=' mark symbolizes a double bond. UQ and MQ correspond to ubiquinone and menaquinone, respectively. As explained in the text, this cycle is not thermodynamically feasible and does not represent a viable alternative for carbon fixation.

Enzymes: (1) Succinyl-CoA Synthetase; (2) 2-Ketoglutarate Synthase; (3) Isocitrate Dehydrogenase and (4) Isocitrate Lyase. E.C. numbers are given in Example 2

FIGS. 4A-4C are diagrams of carbon fixation pathways according to embodiments of the present invention. (A,B) The C4-Glyoxylate cycles. Promising carbon fixation pathways utilizing the most favorable carboxylating enzyme, PEP carboxylase in a nested manner to achieve a cycle resulting in a glyoxylate product easily transformed into GASP. Coloring and symbols are as in FIG. 3. E.C. numbers given in Example 2. (C) The metabolic overlap between the natural C4 module (marked in black) and the synthetic C4-glyoxylate cycles (additional reactions marked in red).

(A) Enzymes: (1) Pyruvate Water (Phosphate) Dikinase; (2) PEP Carboxylase; (3) Malate Dehydrogenase; (4) Malyl-CoA Synthetase; (5) Malyl-CoA Lyase; (6) Methylmalonyl-CoA Carboxytransferase; (7) Malonyl-CoA Reductase (malonate-semialdehyde forming); (8) beta-Alanine-Pyruvate Transaminase and (9) Alanine 2,3-Aminomutase.

(B) Enzymes: (1-6) as in (A); (7) Malonyl-CoA Reductase (3-hydroxypropionate forming); (8) Propionate CoA Transferase; (9) Enoyl-CoA Hydratase; (10) Lactoyl-CoA Dehydratase and (11) Lactate Dehydrogenase.

Figure 5A:
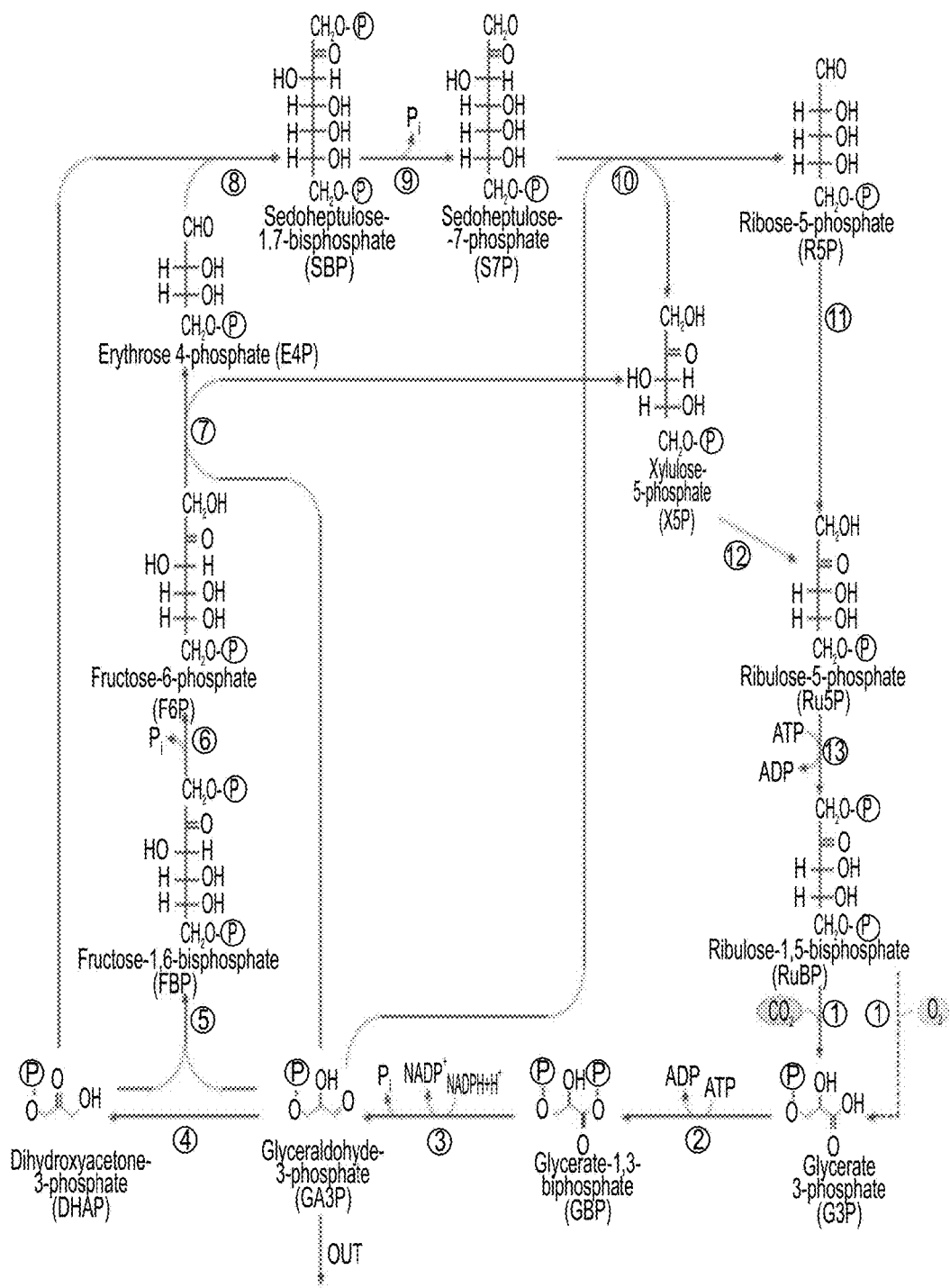

FIG. 5A is a scheme of the reductive pentose phosphate cycle, as inspired from Poolman M G et al 2000, *J Exp Bot* 51 Spec No: 319-328.

Dashed line corresponds to RUBISCO's oxygenase reaction and to the photorespiration pathway. See Examples section. Glyceraldehyde-3-Phosphate is considered as the pathway product.

Enzymes: (1) RUBISCO; (2) Phosphoglycerate Kinase; (3) Glyceraldehyde-3P Dehydrogenase (Phosphorylating); (4) Triose-Phosphate Isomerase; (5) Fructose-Bisphosphate Aldolase; (6) Fructose-Bisphosphatase; (7) Transketolase; (8) Aldolase (Fructose-Bisphosphate Aldolase); (9) Sedoheptulose-Bisphosphatase; (10) Transketolase; (11) Ribose-5-Phosphate Isomerase; (12) Ribulose-Phosphate 3-Epimerase; (13) Phosphoribulokinase. E.C. numbers are given in Example 2.

Figure 5B:
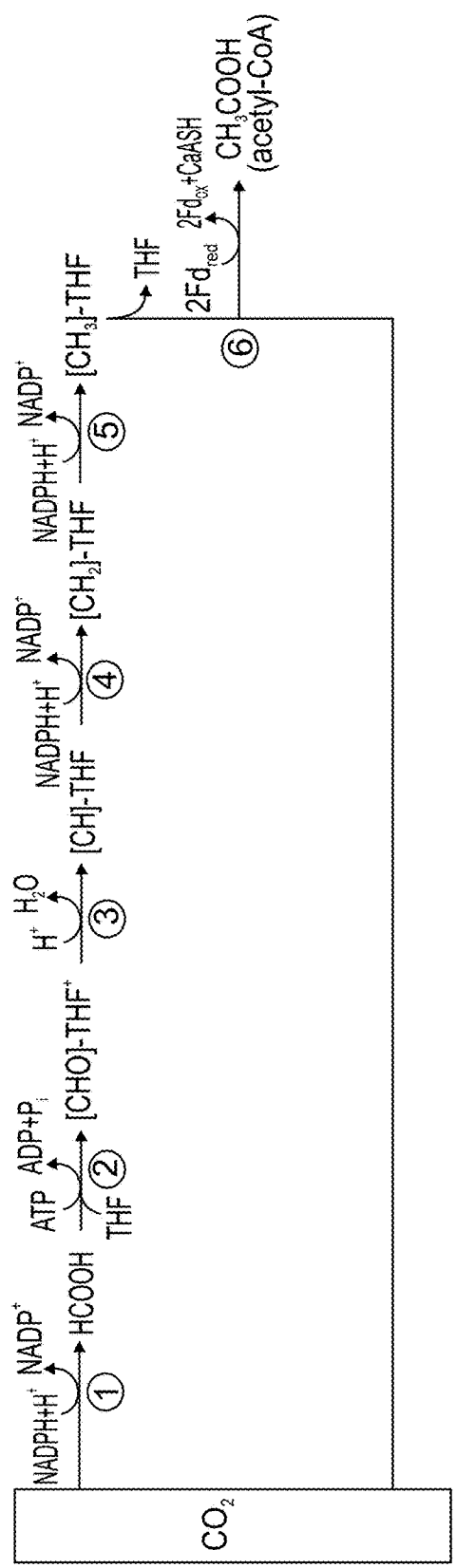

FIG. 5B is a scheme of the reductive acetyl-CoA pathway, as inspired from (Drake H L, Kirsten K, & Matthies C (2006) Acetogenic Prokaryotes *The Prokaryotes*, (Springer New York), pp 354-420). THF corresponds to tetrahydrofolate.

Enzymes: (1) Formate Dehydrogenase; (2) Formyltetrahydrofolate Synthetase; (3) Methenyltetrahydrofolate Cyclohydrolase; (4) Methenyltetrahydrofolate Dehydrogenase; (5) Methenyltetrahydrofolate Reductase; (6) CO dehydrogenase/acetyl-CoA synthase.

Figure 6:
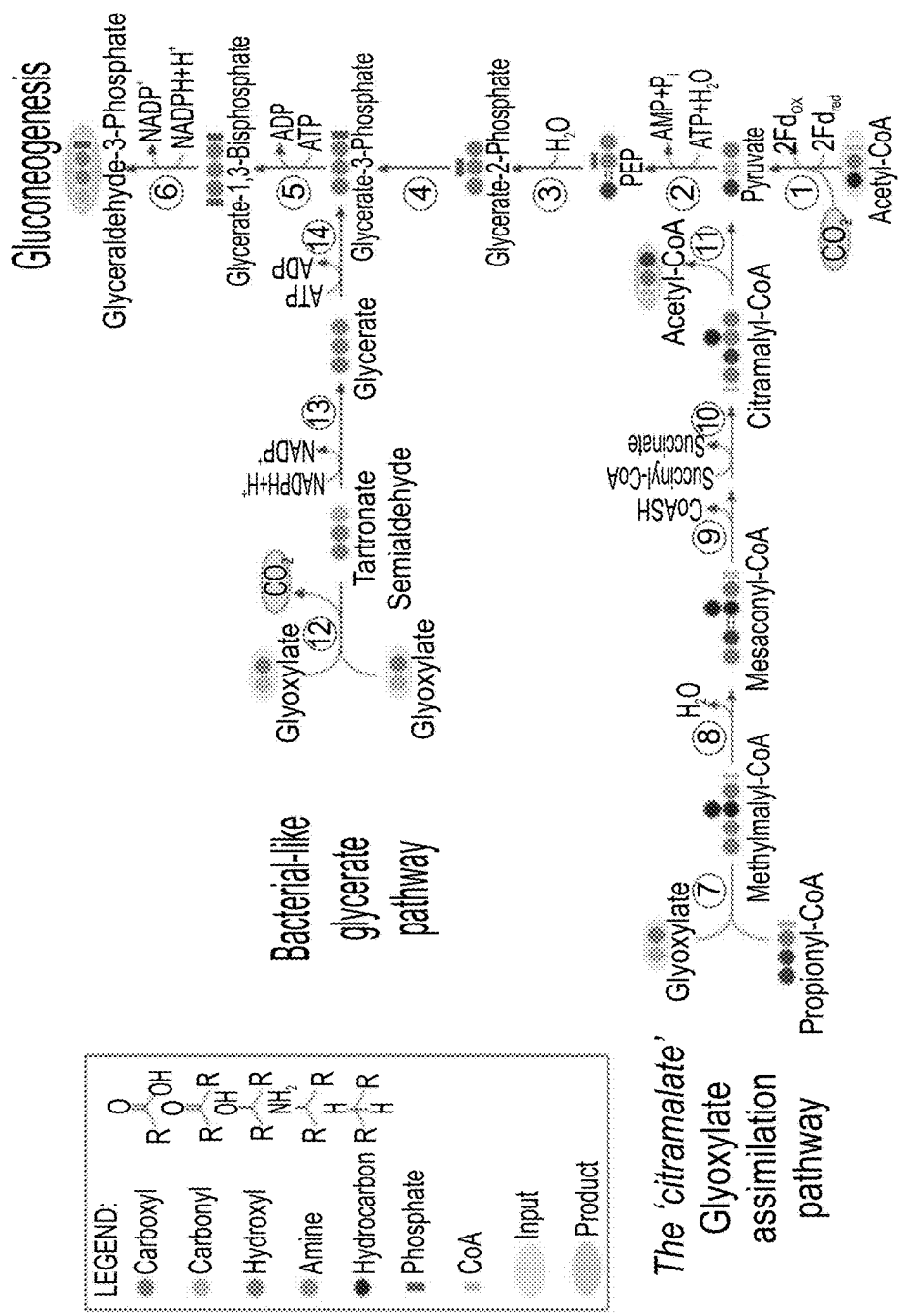
Figures 7A, 7B:
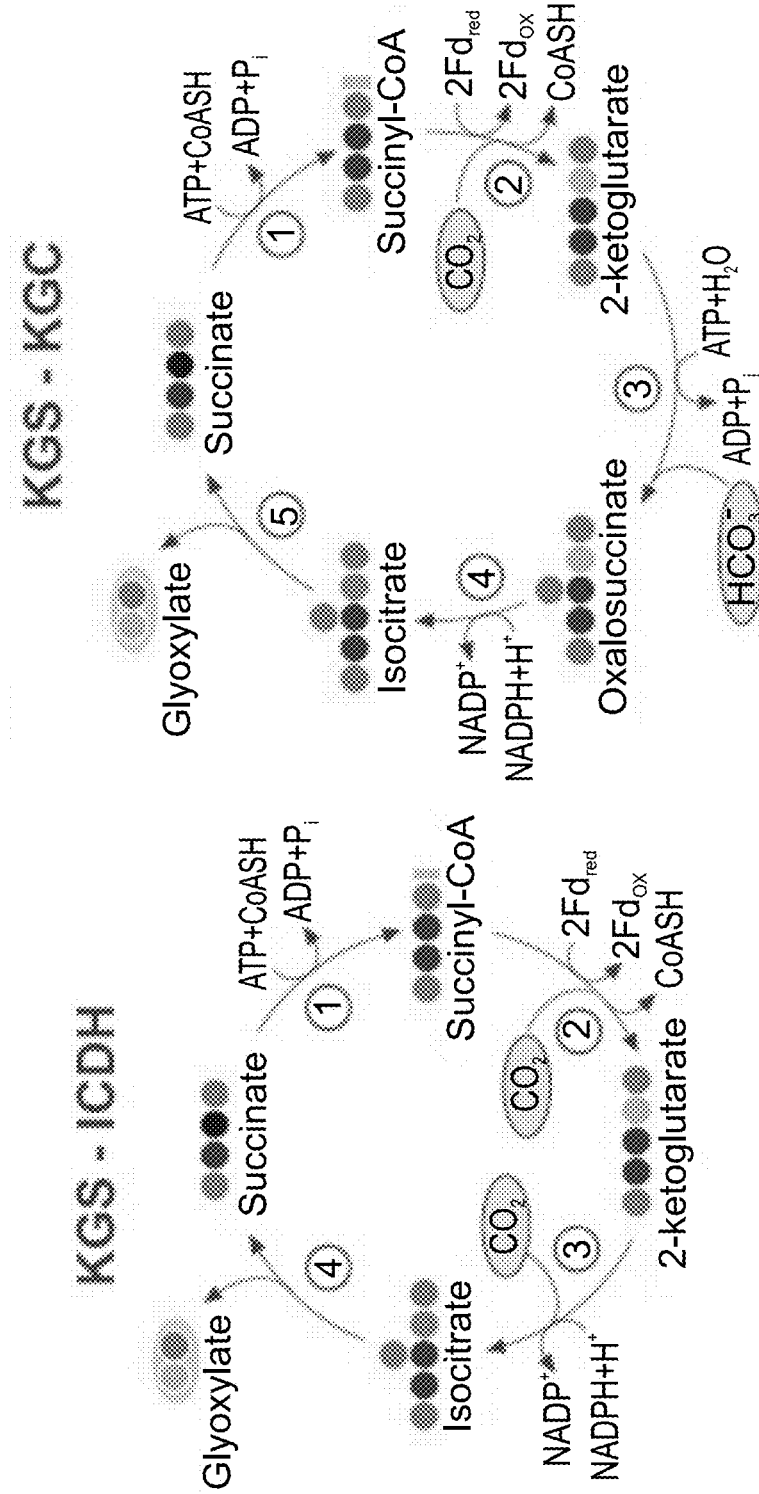
Figures 7C, 7D, 7E:
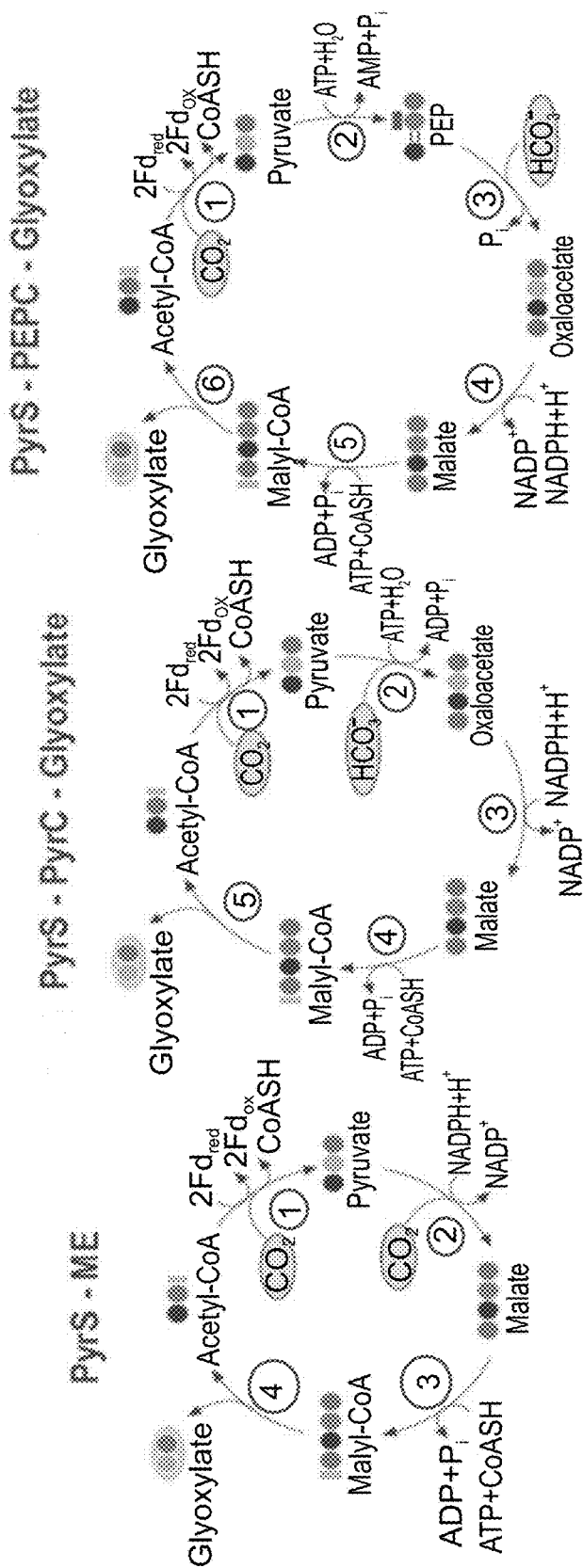
Figures 7F, 7G:
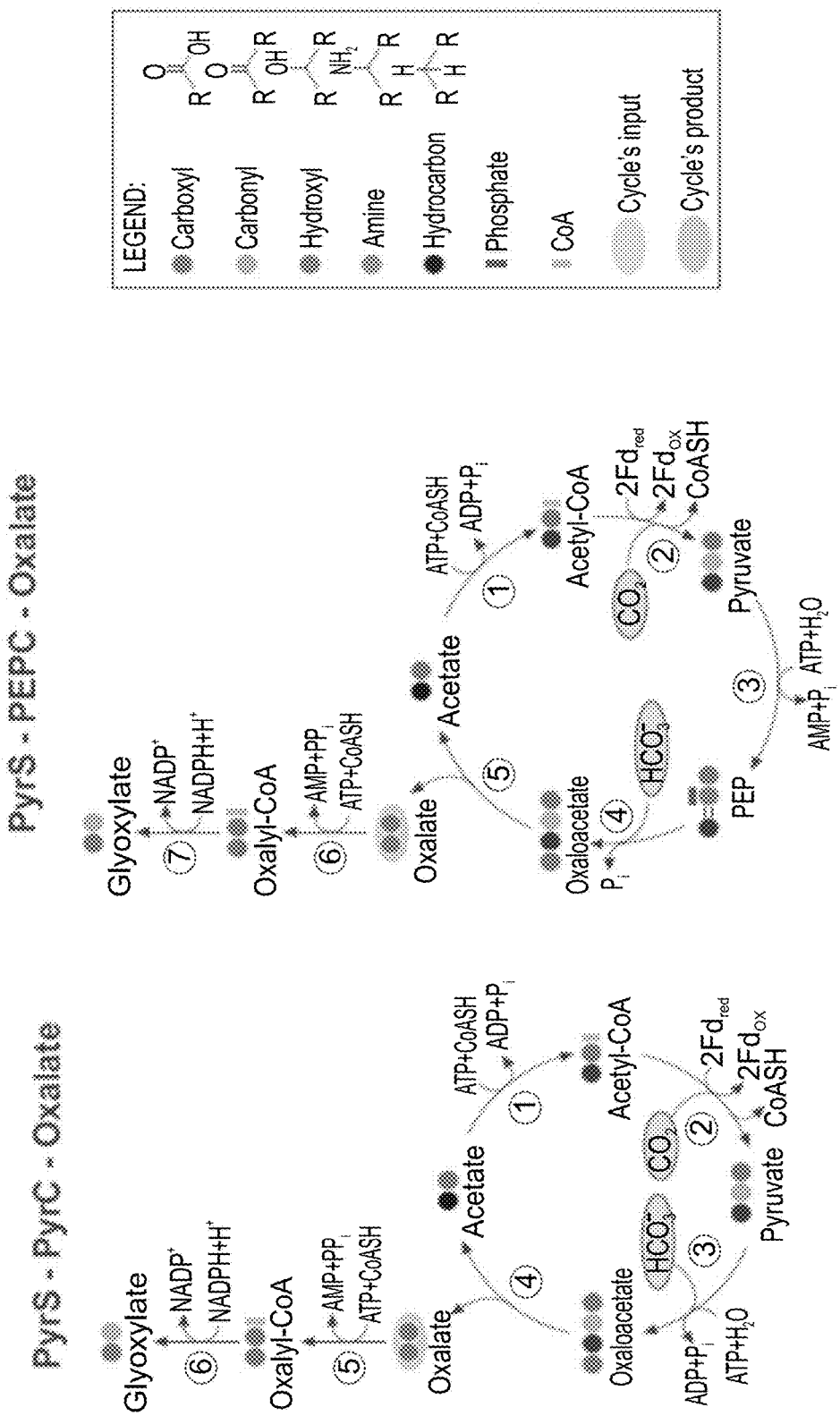

FIG. 6 is a scheme of assimilation pathways. Those pathways convert the products of the different cycles (highlighted in pink) to the common product glyceraldehyde-3-phosphate.

Enzymes: (1) Pyruvate Synthase; (2) Pyruvate Water (Phosphate) Dikinases; (3) Enolase; (4) Phosphoglycerate Mutase; (5) Phosphoglycerate Kinase; (6) Glyceraldehyde-3P Dehydrogenase (Phosphorylating); (7) Methylmalyl-CoA Lyase; (8) Mesaconyl-CoA Hydratase; (9) Un-known; (10) Succinate:Citramalate CoA-Transferase; (11) Citramalyl-CoA Lyase; (12) Glyoxylate Carboligase; (13) Tartronate-Semialdehyde Reductase and (14) Glycerate Kinase.

The coloring scheme is identical to that of FIG. 1. E.C. numbers are given in Example 2.

FIGS. 7A-7G are diagrams of the simplest carbon fixation cycles.

The KGS-ICDH and PyrS-ME pathways are not thermodynamically feasible because they contain a thermodynamic distributed bottleneck (see text). The KGS-KGC and PyrS-PyrC-Glyoxylate pathways are thermodynamically questionable; the free energy change associated with their cycles may be positive under a broad range of estimated physiological concentrations of their product (see text).

(7A) The KGS-ICDH cycle.

Enzymes: (1) Succinyl-CoA Synthetase; (2) 2-Ketoglutarate Synthase; (3) Isocitrate Dehydrogenase and (4) Isocitrate Lyase.

(7B) The KGS-KGC cycle.

Enzymes: (1) Succinyl-CoA Synthetase; (2) 2-Ketoglutarate Synthase; (3) 2-ketoglutarate carboxylase; (4) isocitrate:NADP oxidoreductase and (5) Isocitrate Lyase.

(7C) The PyrS-ME cycle.

Enzymes: (1) Pyruvate Synthase; (2) 'Malic' enzyme; (3) Malyl-CoA Synthetase and (4) Malyl-CoA Lyase.

(7D) The PyrS-PyrC-Glyoxylate cycle.

Enzymes: (1) Pyruvate Synthase; (2) Pyruvate Carboxylase; (3) Malate Dehydrogenase; (4) Malyl-CoA Synthetase and (5) Malyl-CoA Lyase.

(7E) The PyrS-PEPC-Glyoxylate cycle.

Enzymes: (1) Pyruvate Synthase; (2) Pyruvate Water (Phosphate) Dikinase; (3) PEP Carboxylate; (4) Malate Dehydrogenase; (5) Malyl-CoA Synthetase and (6) Malyl-CoA Lyase.

(7F) The PyrS-PyrC-Oxalate cycle.

Enzymes: (1) Acetyl-CoA Synthetase; (2) Pyruvate Synthase; (3) Pyruvate Carboxylase; (4) Oxaloacetase; (5) Oxalyl-CoA Synthetase and (6) Glyoxylate Dehydrogenase (acylating).

(7G) The PyrS-PEPC-Oxalate cycle.

Enzymes: (1) Acetyl-CoA Synthetase; (2) Pyruvate Synthase; (3) Pyruvate Water (Phosphate) Dikinases; (4) PEP Carboxylase; (5) Oxaloacetase; (6) Oxalyl-CoA Synthetase and (7) Glyoxylate Dehydrogenase (acylating).

The coloring scheme is identical to that of FIG. 1. E.C. numbers are given in Example 2.

Figure 8:
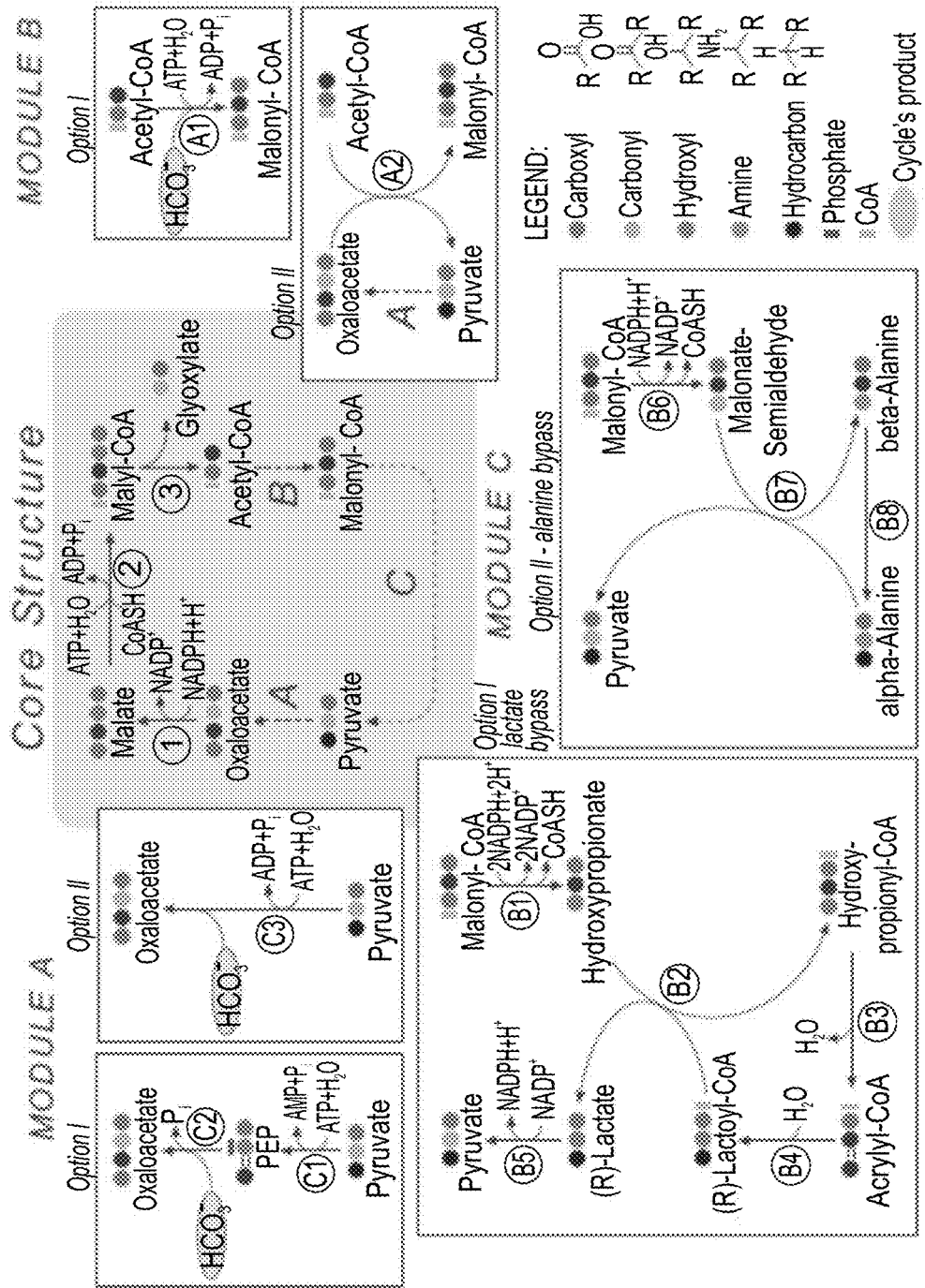

FIG. 8 is a diagram of the core of the most promising carbon fixation pathways family and its modules. The metabolic blueprint of the MOG pathways alongside different metabolic alternatives they can employ. The enzymes lactoyl-CoA dehydratase and alanine 2,3-aminomutase (see below) present several difficulties as explained in detailed in Example 2.

Enzymes of the core structure: (1) Malate Dehydrogenase; (2) Malyl-CoA Synthetase and (3) Malyl-CoA Lyase.

Module A: (C1) Pyruvate Water (Phosphate) Dikinase; (C2) PEP Carboxylase and (C3) Pyruvate Carboxylase.

Module B: (A1) Acetyl-CoA Carboxylase and (A2) Methylmalonyl-CoA Carboxytransferase.

Module C: (B1) Malonyl-CoA Reductase (3-hydroxypropionate forming); (B2) Propionate CoA Transferase; (B3) Enoyl-CoA Hydratase; (B4) Lactoyl-CoA Dehydratase; (B5) Lactate Dehydrogenase; (B6) Malonyl-CoA Reductase (malonate-semialdehyde forming); (B7) beta-Alanine-Pyruvate Transaminase and (B8) Alanine 2,3-Aminomutase.

Coloring and symbols are as in FIG. 1.

Figures 9A, 9B:
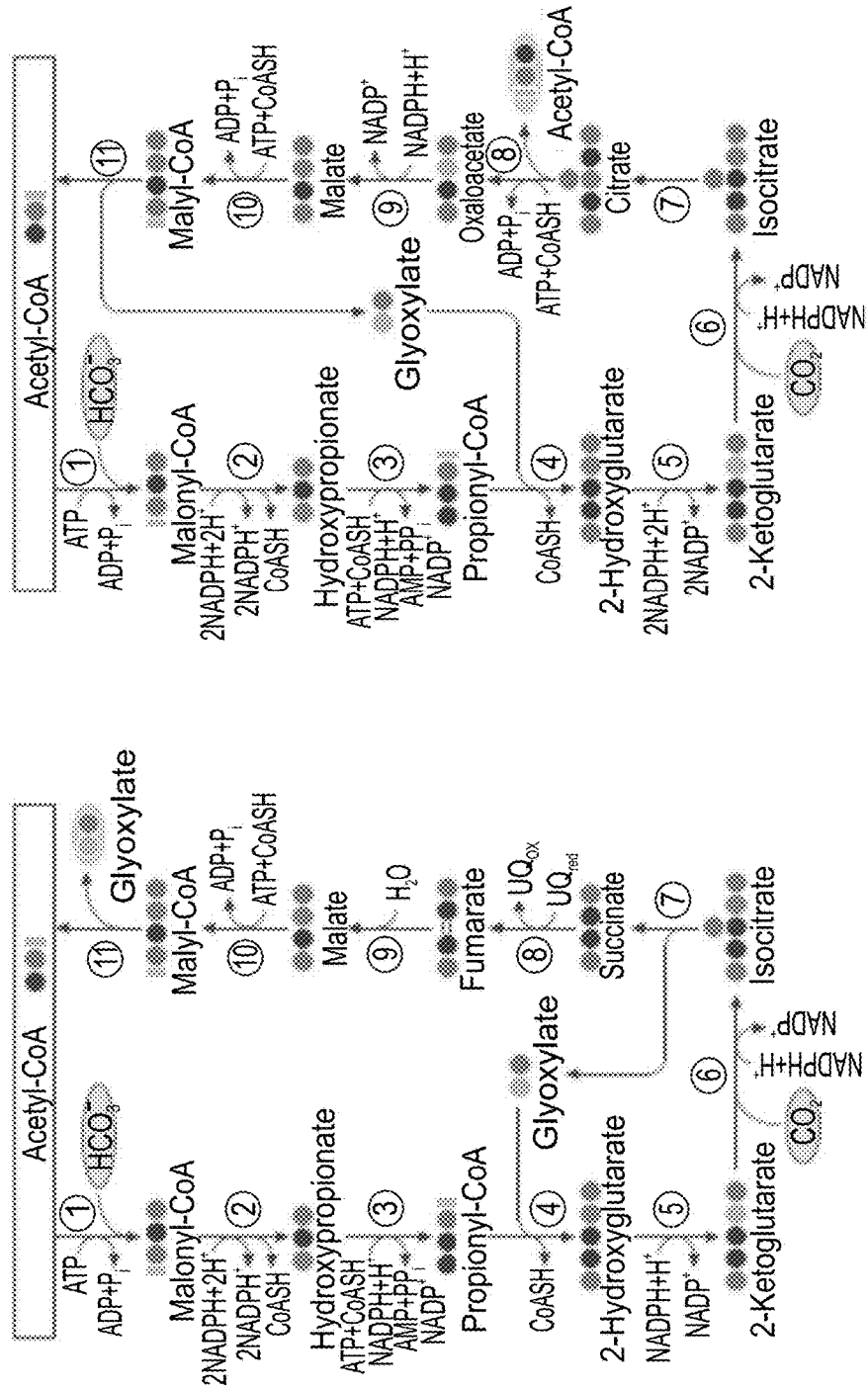
Figure 9C:
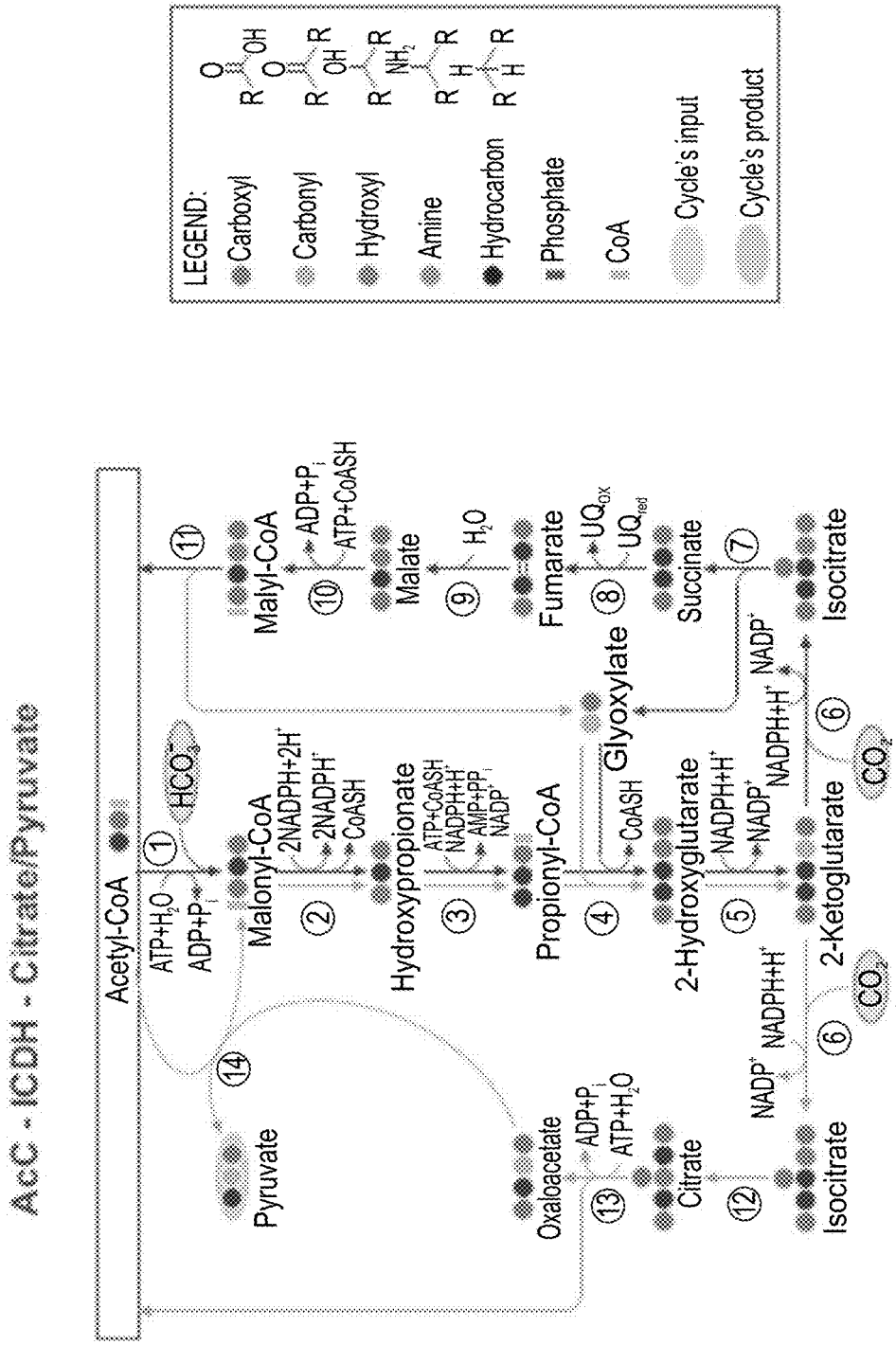
Figures 9D, 9E:
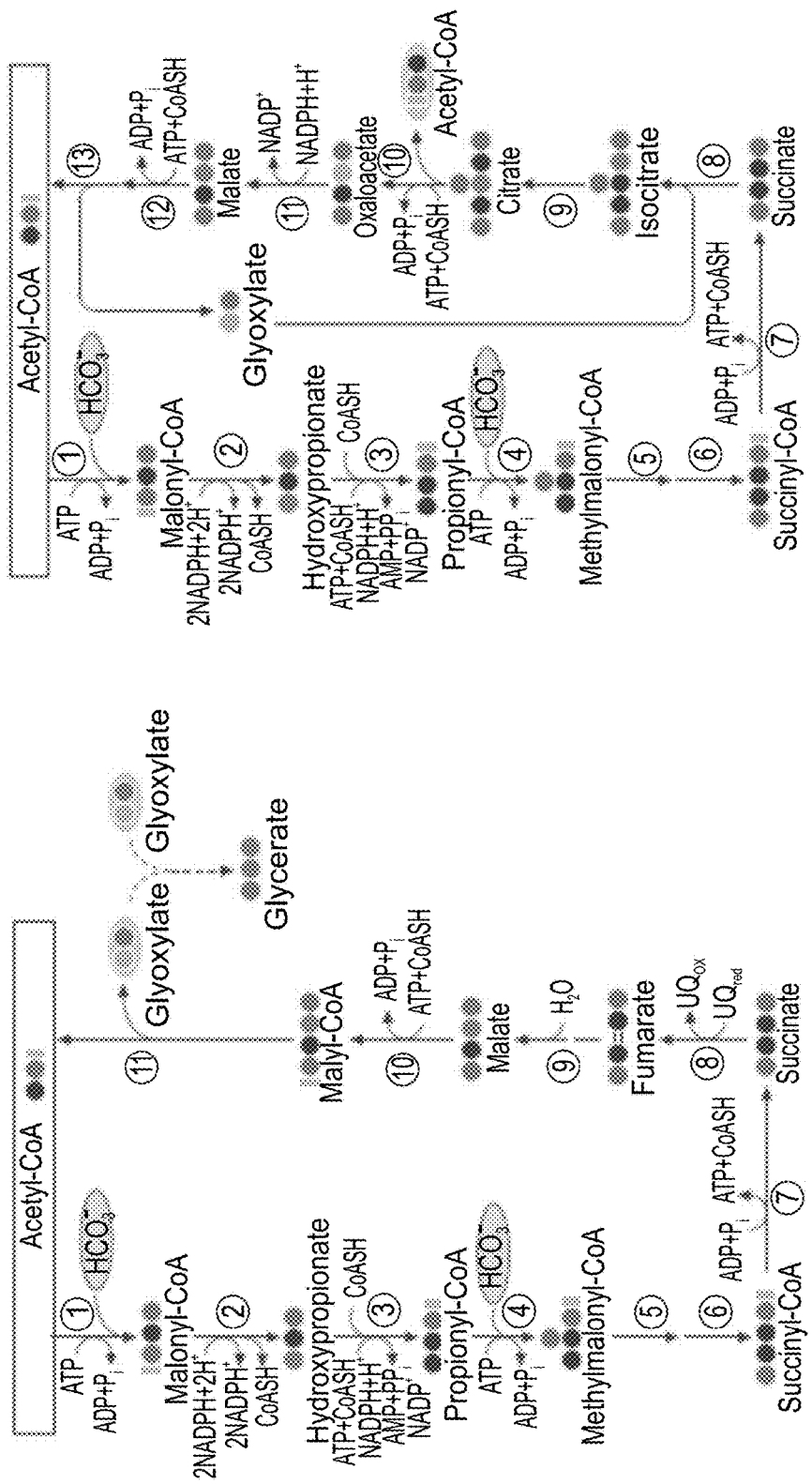
Figures 9F, 9G:
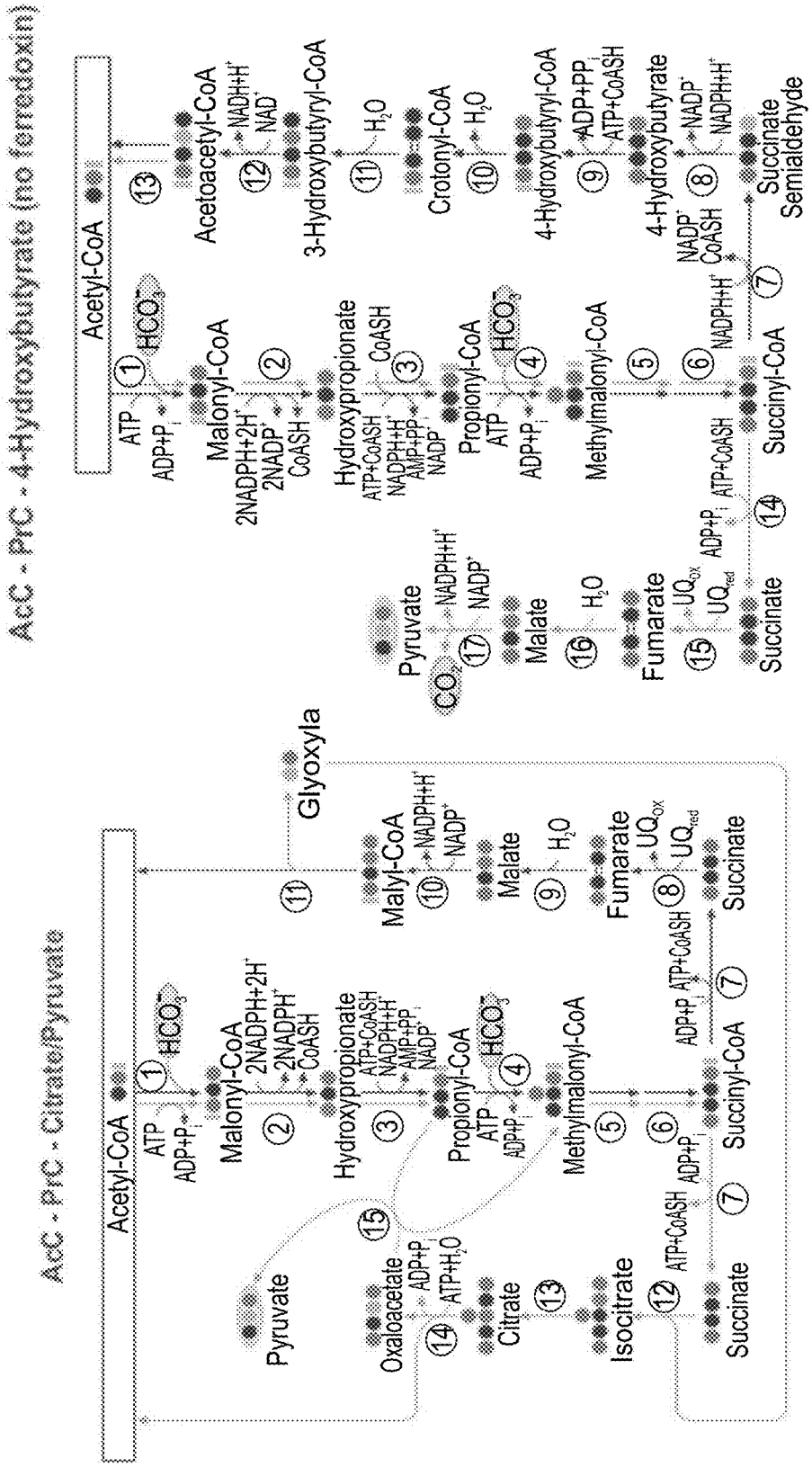
Figure 9H:
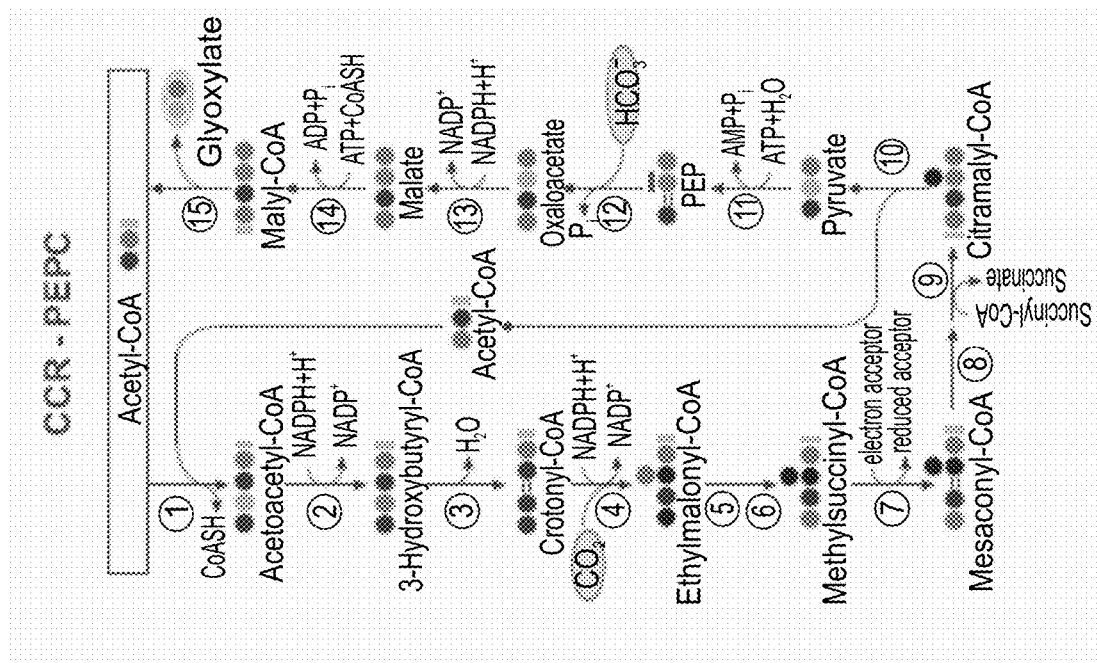
Figures 9I, 9J:
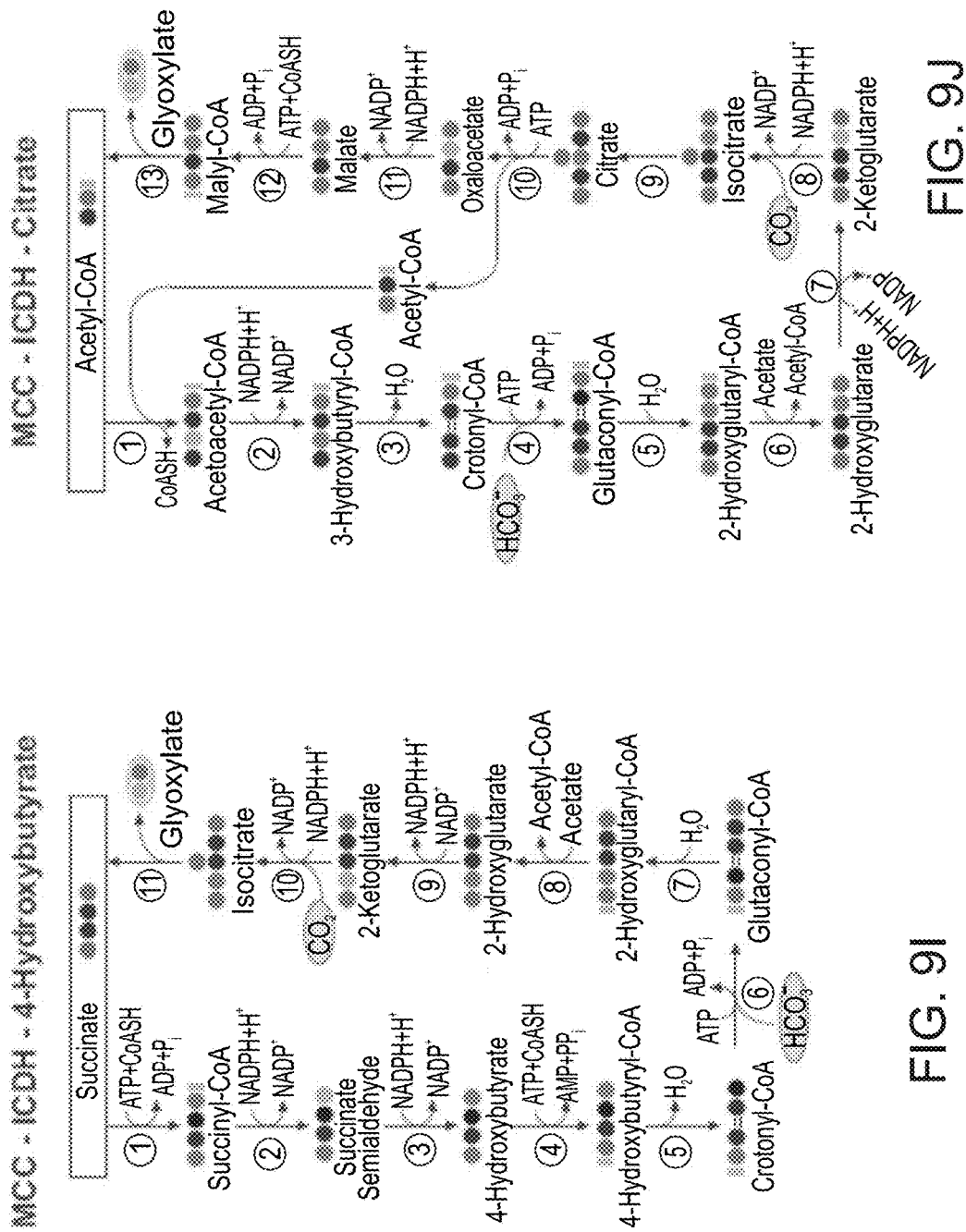
Figure 9K:
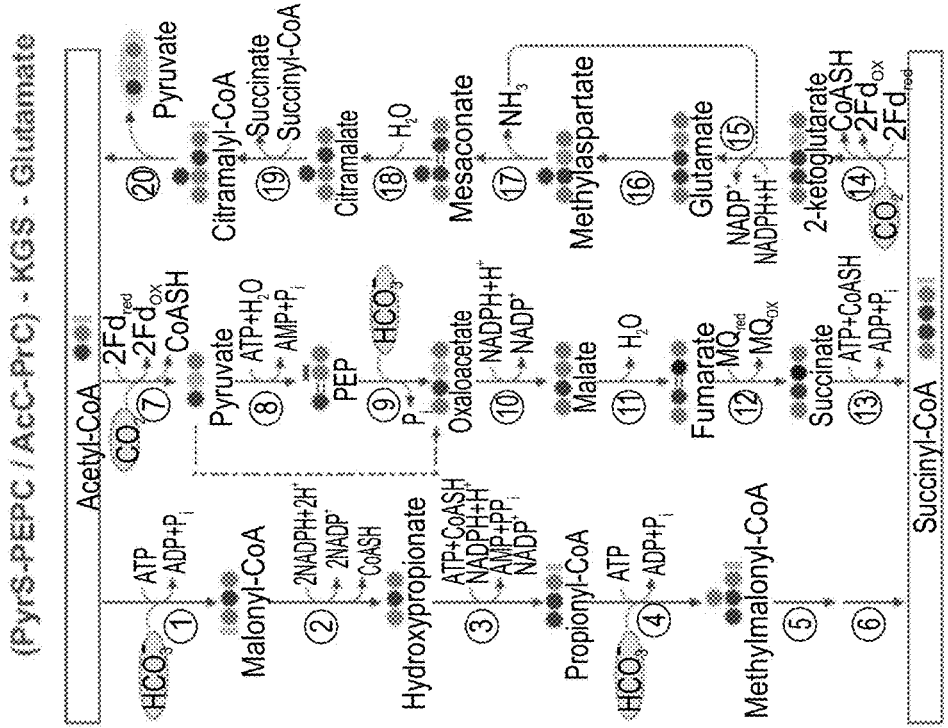
Figure 9N:
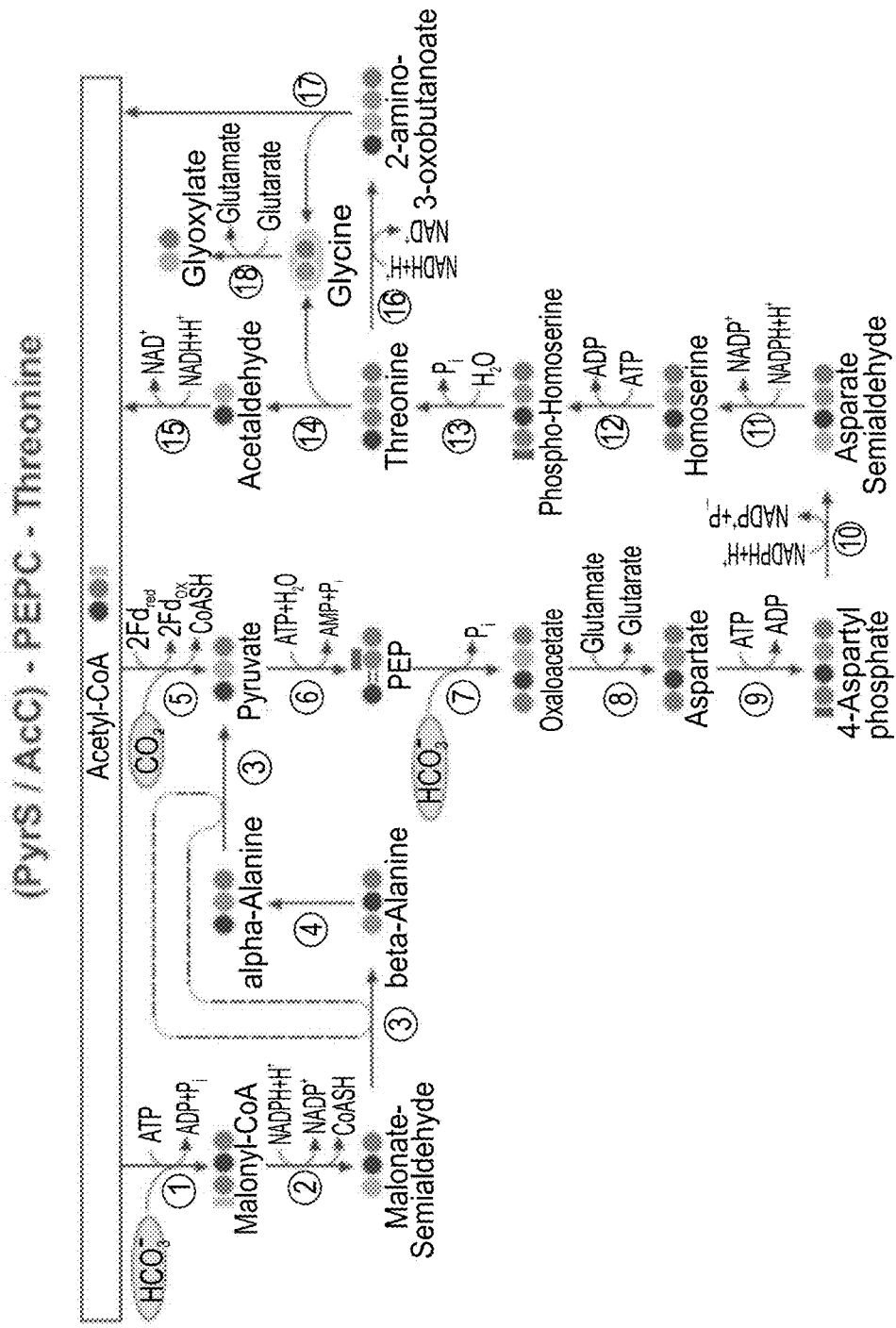

FIGS. 9A-9N are diagrams of other carbon fixation pathways.

(9A) The AcC-ICDH-Glycerate pathway.

Enzymes: (1) Acetyl-CoA Carboxylase; (2) Malonyl-CoA Reductase; (3) Propionyl-CoA synthase; (4) 2-Hydroxyglutarate Synthase; (5) 2-Hydroxyglutarate Dehydrogenase; (6) Isocitrate Dehydrogenase; (7) Isocitrate Lyase; (8) Succinate Dehydrogenase; (9) Fumarate Hydratase; (10) Malyl-CoA Synthetase and (11) Malyl-CoA Lyase.

(9B) The AcC-ICDH-Citrate pathway.

Enzymes: (1) Acetyl-CoA Carboxylase; (2) Malonyl-CoA Reductase; (3) Propionyl-CoA synthase; (4) 2-Hydroxyglutarate Synthase; (5) 2-Hydroxyglutarate Dehydrogenase; (6) Isocitrate Dehydrogenase; (7) Aconitate Hydratase; (8) ATP Citrate Lyase; (9) Malate Dehydrogenase; (10) Malyl-CoA Synthetase and (11) Malyl-CoA Lyase.

(9C) The AcC-ICDH-Citrate/Pyruvate pathway.

Enzymes: (1) Acetyl-CoA Carboxylase; (2) Malonyl-CoA Reductase; (3) Propionyl-CoA synthase; (4) 2-Hydroxyglutarate Synthase; (5) 2-Hydroxyglutarate Dehydrogenase; (6) Isocitrate Dehydrogenase; (7) Aconitate Hydratase; (8) ATP Citrate Lyase; (9) Malate Dehydrogenase; (10) Malyl-CoA Synthetase; (11) Malyl-CoA Lyase; (12) Aconitate Hydratase; (13) ATP Citrate Lyase and (14) Methylmalonyl-CoA Carboxytransferase.

(9D) The AcC-PrC-Glycerate pathway.

Enzymes: (1) Acetyl-CoA Carboxylase; (2) Malonyl-CoA Reductase; (3) Propionyl-CoA synthase; (4) Propionyl-CoA Carboxylase; (5) Methylmalonyl-CoA Epimerase; (6) Methylmalonyl-CoA Mutase; (7) Succinyl-CoA Synthetase; (8) Succinate Dehydrogenase; (9) Fumarase; (10) Malyl-CoA Synthetase and (11) Malyl-CoA Lyase.

(9E) The AcC-PrC-Citrate pathway.

Enzymes: (1) Acetyl-CoA Carboxylase; (2) Malonyl-CoA Reductase; (3) Propionyl-CoA synthase; (4) Propionyl-CoA Carboxylase; (5) Methylmalonyl-CoA Epimerase; (6) Methylmalonyl-CoA Mutase; (7) Succinyl-CoA Synthetase; (8) Isocitrate Lyase; (9) Aconitate Hydratase; (10) ATP Citrate Lyase; (11) Malate Dehydrogenase; (12) Malyl-CoA Synthetase and (13) Malyl-CoA Lyase.

(9F) The AcC-PrC-Citrate/Pyruvate pathway.

Enzymes: (1) Acetyl-CoA Carboxylase; (2) Malonyl-CoA Reductase; (3) Propionyl-CoA synthase; (4) Propionyl-CoA Carboxylase; (5) Methylmalonyl-CoA Epimerase; (6) Methylmalonyl-CoA Mutase; (7) Succinyl-CoA Synthetase; (8) Succinate Dehydrogenase; (9) Fumarate Hydratase; (10) Malyl-CoA Synthetase; (11) Malyl-CoA Lyase; (12) Isocitrate Lyase; (13) Aconitate Hydratase; (14) ATP Citrate Lyase and (15) Methylmalonyl-CoA Carboxytransferase.

(9G) The AcC-PrC-4-Hydroxybutyrate (no ferredoxin) pathway.

Enzymes: (1) Acetyl-CoA Carboxylase; (2) Malonyl-CoA Reductase; (3) Propionyl-CoA synthase; (4) Propionyl-CoA Carboxylase; (5) Methylmalonyl-CoA Epimerase; (6) Methylmalonyl-CoA Mutase; (7) Succinyl-CoA Reductase; (8) 4-Hydroxybutyrate Dehydrogenase; (9) 4-Hydroxybutyryl-CoA Synthetase; (10) 4-Hydroxybutyryl-CoA Dehydratase; (11) Enoyl-CoA Hydratase (Crotonase); (12) 3-Hydroxybutyryl-CoA Dehydrogenase; (13) Acetyl-CoA C-Acyltransferase; (14) Succinyl-CoA Synthetase; (15) Succinate Dehydrogenase; (16) Fumarate Hydratase and (17) Malic enzyme.

(9H) The CCR-PEPC pathway.

Enzymes: (1) Acetyl-CoA C-Acyltransferase; (2) 3-Hydroxybutyryl-CoA Dehydrogenase; (3) Enoyl-CoA Hydratase (Crotonase); (4) Crotonyl-CoA Carboxylase/Reductase; (5) Ethylmalonyl-CoA Epimerase; (6) Ethylmalonyl-CoA Mutase; (7) Methylsuccinyl-CoA Dehydrogenase; (8) Un-known; (9) Succinate:Citramalate CoA-Transferase; (10) Citramalyl-CoA Lyase; (11) Pyruvate Water (Phosphate) Dikinases; (12) PEP Carboxylase; (13) Malate Dehydrogenase; (14) Malyl-CoA Synthetase and (15) Malyl-CoA Lyase.

(9I) The MCC-ICDH-4-Hydroxybutyrate pathway.

Enzymes: (1) Succinyl-CoA Synthetase; (2) Succinyl-CoA Reductase; (3) 4-Hydroxybutyrate Dehydrogenase; (4) 4-Hydroxybutyryl-CoA Synthetase; (5) 4-Hydroxybutyryl-CoA Dehydratase; (6) Methylcrotonyl-CoA Carboxylase; (7) (R)-2-Hydroxyglutaryl-CoA Dehydratase; (8) Glutaconate CoA-Transferase; (9) 2-Hydroxyglutarate Dehydrogenase; (10) Isocitrate Dehydrogenase and (11) Isocitrate Lyase.

(9J) The MCC-ICDH-Citrate pathway.

Enzymes: (1) Acetyl-CoA C-Acyltransferase; (2) 3-Hydroxybutyryl-CoA Dehydrogenase; (3) Enoyl-CoA Hydratase (Crotonase); (4) Methylcrotonyl-CoA Carboxylase; (5) (R)-2-Hydroxyglutaryl-CoA Dehydratase; (6) Glutaconate CoA-Transferase; (7) 2-Hydroxyglutarate Dehydrogenase; (8) Isocitrate Dehydrogenase; (9) Aconitate Hydratase; (10) ATP Citrate Lyase; (11) Malate Dehydrogenase; (12) Malyl-CoA Synthetase and (13) Malyl-CoA Lyase.

(9K) The PyrS-PEPC-KGS-Glutamate pathway and the AcC-PrC-KGS-Glutamate pathway.

Enzymes: (1) Acetyl-CoA Carboxylase; (2) Malonyl-CoA Reductase; (3) Propionyl-CoA synthase; (4) Propionyl-CoA Carboxylase; (5) Methylmalonyl-CoA Epimerase; (6) Methylmalonyl-CoA Mutase; (7) Pyruvate Synthase; (8) Pyruvate Water (Phosphate) Dikinase; (9) PEP Carboxylase; (10) Malate Dehydrogenase; (11) Fumarate Hydratase; (12) Succinate Dehydrogenase; (13) Succinyl-CoA Synthetase; (14) 2-Ketoglutarate Synthase (15) Glutamate Dehydrogenase; (16) Glutamate Mutase; (17) Methylaspartate Ammonia-Lyase; (18) 2-Methylmalate Dehydratase; (19) Succinate: Citramalate CoA-Transferase and (20) Citramalyl-CoA Lyase.

(9L) The PrC-KGS-Glutamate pathway.

Enzymes: (1) Propionyl-CoA Carboxylase; (2) Methylmalonyl-CoA Epimerase; (3) Methylmalonyl-CoA Mutase; (4) 2-Ketoglutarate Synthase (5) Glutamate Dehydrogenase; (6) Glutamate Mutase; (7) Methylaspartate Ammonia-Lyase; (8) Un-Known; (9) Mesaconyl-CoA Hydratase and (10) Methylmalyl-CoA Lyase.

(9M) The PyrS-KGS-Glutamate pathway.

Enzymes: (1) Pyruvate synthase; (2) Citramalate Synthase; (3) Mesaconate Hydratase; (4) Methylaspartate Ammonia-Lyase; (5) Glutamate Mutase; (6) Glutamate Dehydrogenase; (7) Isocitrate Dehydrogenase; (8) Aconitate Hydratase; (9) ATP Citrate Lyase; (10) Malate Dehydrogenase; (11) Malyl-CoA Synthetase and (12) Malyl-CoA Lyase.

(9N) The PyrS-PEPC-Threonine pathway and the AcC-PEPC-Threonine pathway.

Enzymes: (1) Acetyl-CoA Carboxylase; (2) Malonyl-CoA Reductase (malonate-semialdehyde forming); (3) beta-Alanine-alpha-Alanine Transaminase; (4) Alanine Aminomutase; (5) Pyruvate Synthase; (6) Pyruvate Water (Phosphate) Dikinase; (7) PEP Carboxylase; (8) Aspartate Transaminase; (9) Aspartate Kinase; (10) Aspartate-Semialdehyde Dehydrogenase; (11) Homoserine Dehydrogenase; (12) Homoserine Kinase; (13) Threonine Synthase; (14) Threonine Aldolase; (15) Acetaldehyde Dehydrogenase (acetylating); (16) L-Threonine 3-Dehydrogenase; (17) Glycine C-Acetyltransferase and (18) Glycine Transaminase.

The coloring scheme is identical to that of FIG. 1. E.C. numbers are given in Example 2.

Figure 10A:
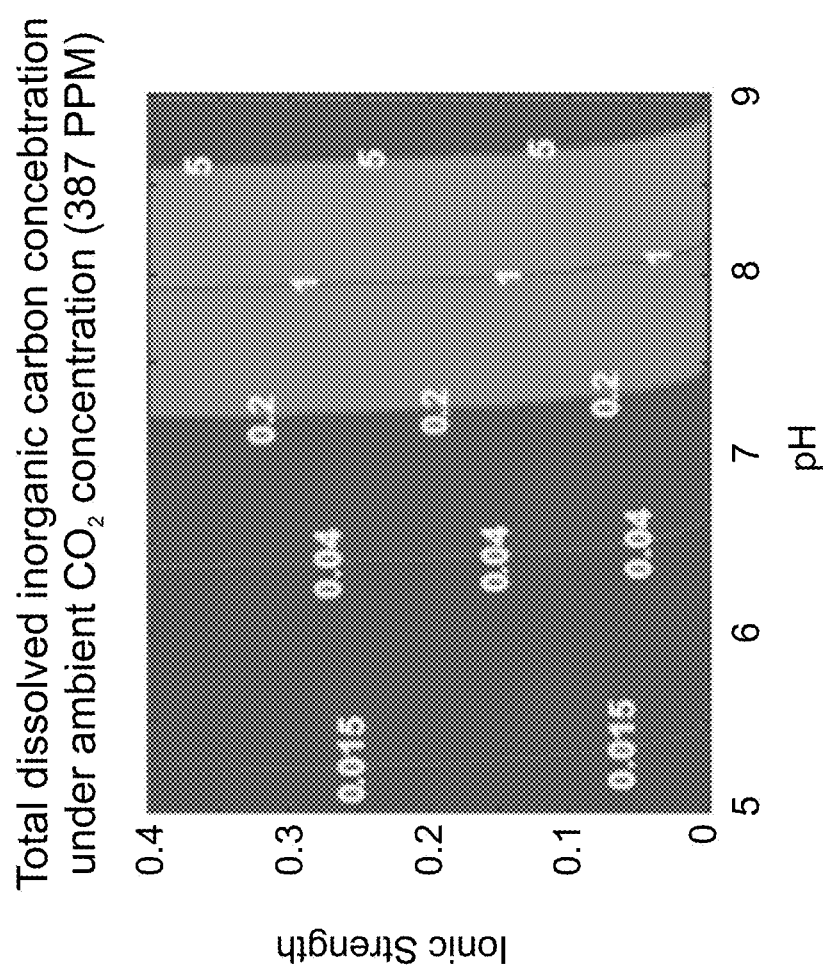
Figure 10B:
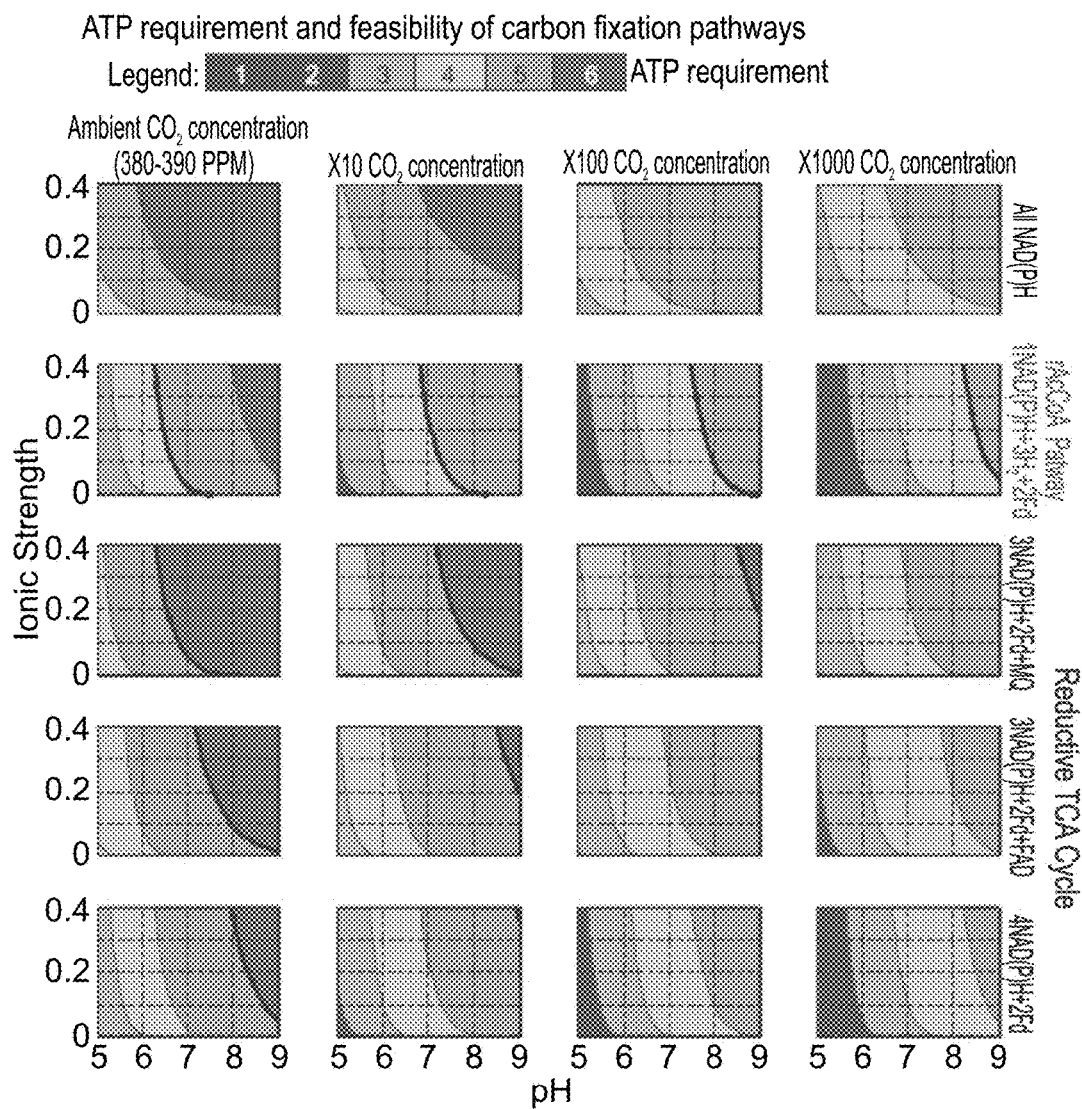
Figure 10C:
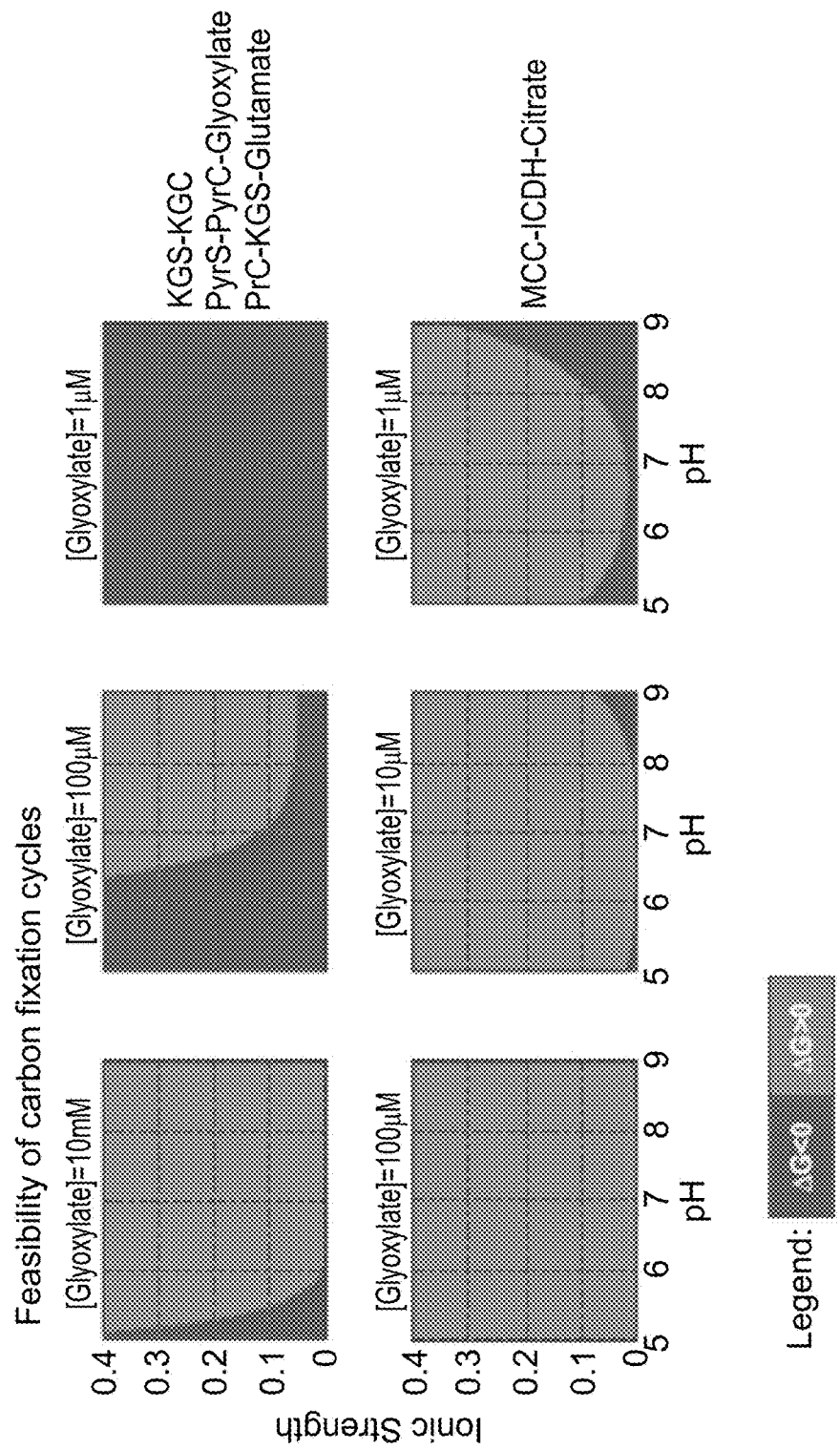

FIGS. 10A-10C are diagrams illustrating the thermodynamics of carbon fixation pathways.
(A) Total dissolved inorganic carbon ($CO_2^{aq}+HCO_3^-+CO_3^{2-}+H_2CO_3^{aq}$) as a function of pH and ionic strength, under ambient $CO_2^{gas}$ concentration, 387 ppm.
(B) Minimal ATP requirement and feasibility of carbon fixation pathways. The common product was assumed to be GA3P. Different electron donors schemes are contrasted as varying conditions of pH, ionic strength and $CO_2^{gas}$ concentrations. First row: all 6 of the electron donors are NAD(P)H, as in the case of the reductive pentose phosphate pathway. Second row: 3 of the electron donors are ferredoxins (Fd) and the other 3 are NAD(P)H, as in the case of the rAcCoA pathway. Third row: 2 of the electron donors are ferredoxins, 1 is menaquinone (MQ) and the other 3 are NAD(P)H, as in the case of the rTCA cycle, where menaquinone is the electron donor for fumarate reductase. Forth row: 2 of the electron donors are ferredoxins, 1 is FAD and the other 3 are NAD(P)H, as in the case of the rTCA cycle, where FAD is the electron donor for fumarate reductase. Fifth row: 2 of the electron donors are ferredoxins and the other 4 are NAD(P)H, as in the case of the rTCA cycle, where NADH is the direct electron donor for fumarate reductase. Columns correspond to different $CO_2^{gas}$ concentrations. Bold lines correspond to the feasibility ranges of the pathways: the pathways are not feasible at pH and ionic strength values corresponding to the area to the right of those lines.
(C) Feasibility of carbon fixation cycles, as separate metabolic units within the pathways, as function of pH, ionic strength and different concentrations of the cycles' product, glyoxylate. Blue represents the feasibility range ($\Delta G<0$), while red corresponds to infeasibility of carbon fixation ($\Delta G>0$). The upper boxes correspond to the ferredoxin-oxidoreductase pathways KGS-KGC, PyrS-PyrC-Glyoxylate and PrC-KGS-Glutamate. The bottom boxes correspond to the non-ferredoxin-oxidoreductase-containing pathway MCC-ICDH-Citrate.

Figure 11:
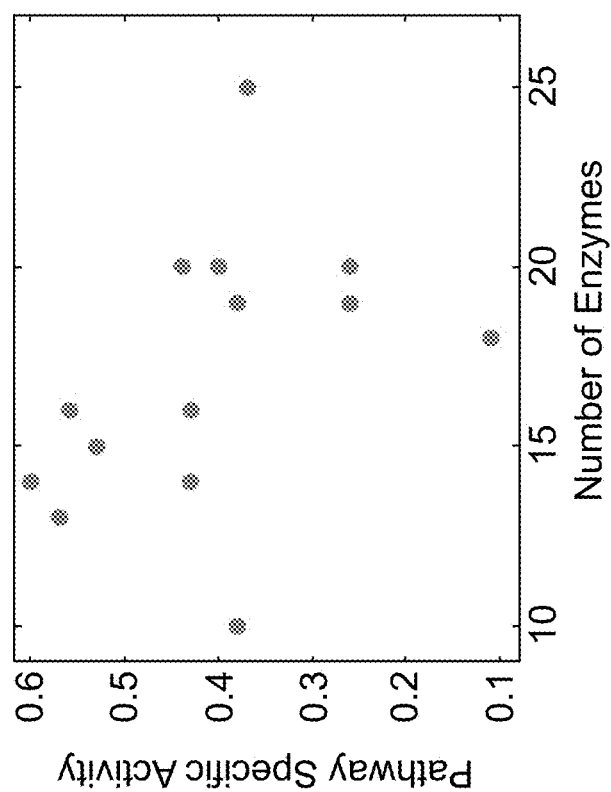

FIG. 11 is a graph illustrating pathway specific activity as a function of the number of enzymes.

Figure 12:
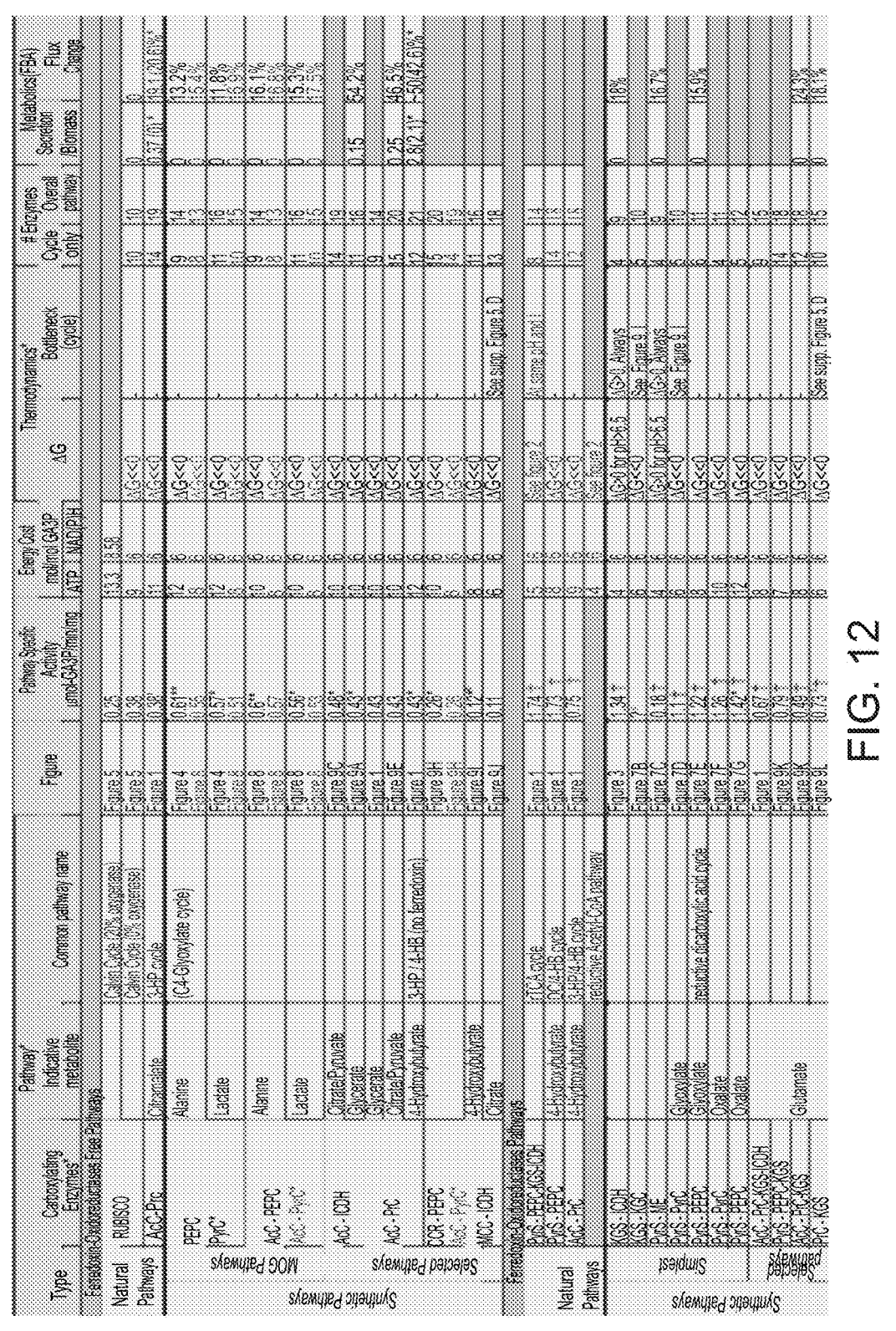

FIG. 12 is a table (Table 1) comparing carbon fixation pathways.

† The pathway specific activities of the ferredoxine-oxidoreductase pathways are artificially high because their calculations do not include the specific activities of the ferredoin-oxidoreductase enzymes; see main text.

(a) Pathway notation and a comprehensive discussion is given in Example 2.

(b) AcC: acetyl-CoA carboxylase; PEPC: PEP carboxylase; PrC: propionyl-CoA carboxylase; ICDH: isocitrate dehydrogenase; CCR: crotonyl-CoA carboxylase/reductase and MMC: methylcrotonyl-CoA carboxylase.

(c) See Example 2 and FIGS. 10A-10C for further details on the energetics of the carbon fixation pathways.

(d) The specific activity of the enzyme alanine 2,3-aminomutase is not known, and therefore not included in the calculation of the pathway specific activity, which might be somewhat lower.

(e) Refers to a pathway using the enzymes PEP caboxylase and pyruvate dikinase. The values given in green, at the raw below, refer to a pathway utilizing the enzyme pyruvate carboxylase.

(f) The enzyme which converts mesaconyl-CoA into citramalate is not known. Therefore, its specific activity was not included in the calculation of the specific activity of the pathway, which might be somewhat lower.

(g) The specific activity of the enzyme 2-hydroxyglutarate synthase is not known, and therefore not included in the calculation of the pathway specific activity, which might be somewhat lower.

(h) The specific activity of the enzyme 4-hydroxybutyryl-CoA synthetase is not known, and therefore not included in the calculation of the pathway specific activity, which might be somewhat lower.

(i) The enzyme which converts methylsuccinyl-CoA into mesaconyl-CoA is not known. Therefore, its specific activity was not included in the calculation of the specific activity of the pathway, which might be somewhat lower.

(j) The specific activity of the carboxylating enzyme 2-ketoglutarate carboxylase is not known (see FIGS. 5A-5B) and therefore the pathway specific activity was not calculated.

(k) The specific activity of the enzyme oxalate CoA ligase is not known, and therefore not included in the calculation of the pathway specific activity, which might be somewhat lower.

(l) The enzyme which converts mesaconate into mesaconyl-CoA is not known. Therefore, its specific activity was not included in the calculation of the specific activity of the pathway, which might be somewhat lower.

(m) The value out of the parentheses refers to a cycle in which the succinate dehydrogenase utilizes ubiquinone. The value inside of the parentheses refers to a cycle in which the succinate dehydrogenase utilizes NADPH (a non-natural co-factor for this enzyme). See Example 2.

(n) The value out of the parentheses refers to a cycle in which the glyoxylate shunt utilizes ubiquinone or FAD. The value inside of the parentheses refers to a cycle in which the glyoxylate shunt utilizes NADPH. See Example 2.

FIG. 13 is a table (Table 2) comparing carboxylating enzymes.

(a) Several carboxylating enzymes were not evaluated: (1) "dead-end" carboxylating enzymes (carbamate kinase, urea carboxylase and carbamoyl-phosphate synthase); (2) enzymes that are specific to high molecular-weight-metabolites (indolepyruvate ferredoxin oxidoreductase, 2-oxopropyl-CoM reductase, phosphoribosylaminoimidazole carboxylase and geranoyl-CoA carboxylase) and (3) the reductive acetyl-CoA pathway's enzymes which does not fixate $CO_2$ and bicarbonate directly (carbon monoxide dehydrogenase, formate dehydrogenase and acetyl-CoA synthase).

(b) Km and specific activity (saturating $CO_2/HCO_3^-$) values were collected from the literature. Specific activities in ambient $CO_2/HCO_3^-$ were calculated by assuming Michaelis-Menten kinetics with no cooperativity (See Example 2). For each enzyme and for all the three criteria the worse half of values (the less optimized enzymes) was discarded as well as the top 10% (which might present outliers and errors in measurements) (see Methods). The table shows the average of the remaining values, and their range in parentheses.

(c) $CO_2$ concentration was estimated as 10 μM, while $HCO_3^-$ concentration was conservatively estimated as 200 μM (Berg et al. *Science* 14 Dec. 2007).

(d) Under common physiological conditions.

(e) Although the carbon species utilized in $CO_2$, affinity was measured using varied concentrations of bicarbonate.

(f) Values taken from one paper only.

(g) Scarcity of literature information about the carboxylation reaction, as well as extreme oxygen sensitivity disabled reliable specific activity estimation.

(h) Values in Italic correspond to carboxylation rates of crotonyl-CoA (~35% of methylcrotonyl-CoA).

(i) Rate of carboxylation, under saturating $CO_2/HCO_3^-$, is higher than that of decarboxylation. However, under ambient $CO_2/HCO_3^-$ the decarboxylation rate is higher.

(j) The enzyme is inactivated by the direct action of $O_2$. However, the enzyme is operating (and remain active) in the mitochondria of Euglena grown aerobically where it is stabilized by its co-factor: thiamine diphosphate.

(k) Although this enzyme is not a carboxylating one per se, it can be used instead of a true carboxylating enzyme (see FIG. 4).

FIG. 14 is a table providing enzyme kinetic details. Yellow shading corresponds to specific activity under substrate saturating conditions. Red shading represents the specific activity of enzymes under ambient inorganic carbon concentration, where $SA_{ambient}=SA_{saturating}*[C]/([C]+K_m^C)$. [C] is the ambient concentration of the carbon species and $K_m^C$ is the affinity of the enzyme towards that carbon species. Purple shading stand for the specific activities of the ferredoxin-oxidoreductase enzymes, for which kinetic data is scares in the carboxylation direction. Pink and blue shading correspond to ATP and NADPH costs, respectively.

Figure 15:
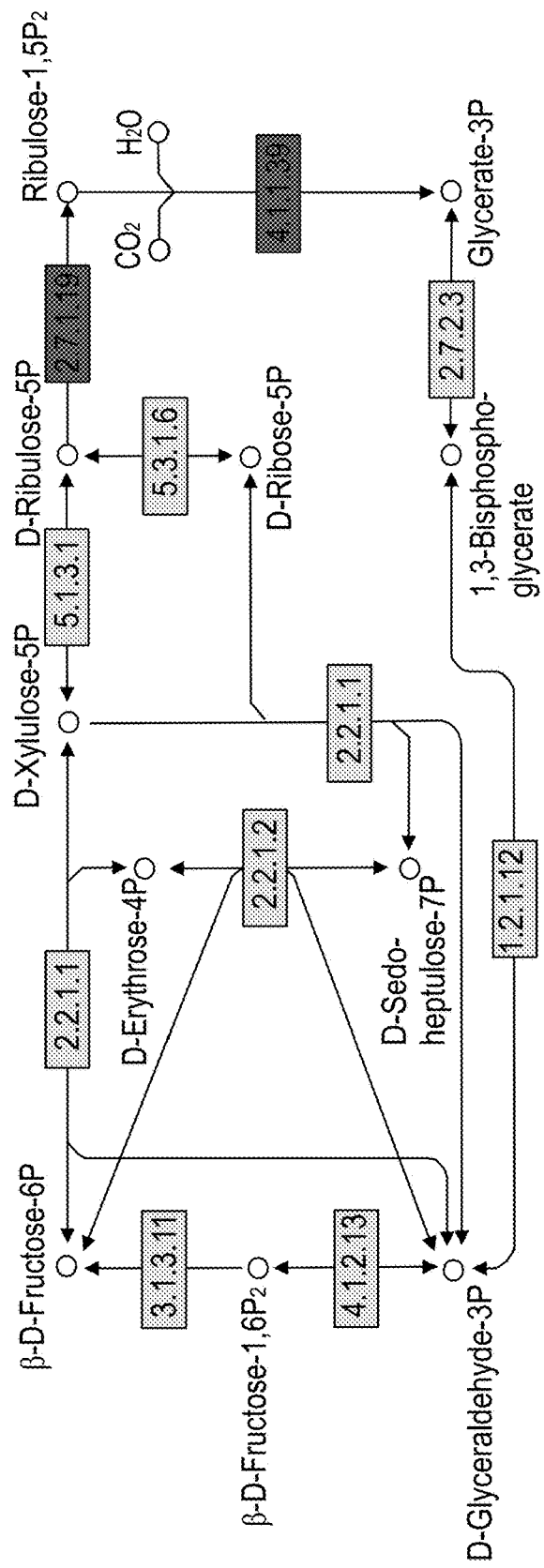

FIG. 15 is a diagram illustrating the proposed (modified) Calvin-Benson Cycle in *E. coli* (KEGG-style). Green boxes represent native enzymes, while red boxes correspond to foreign enzymes that should be expressed in the host.

Figure 16:
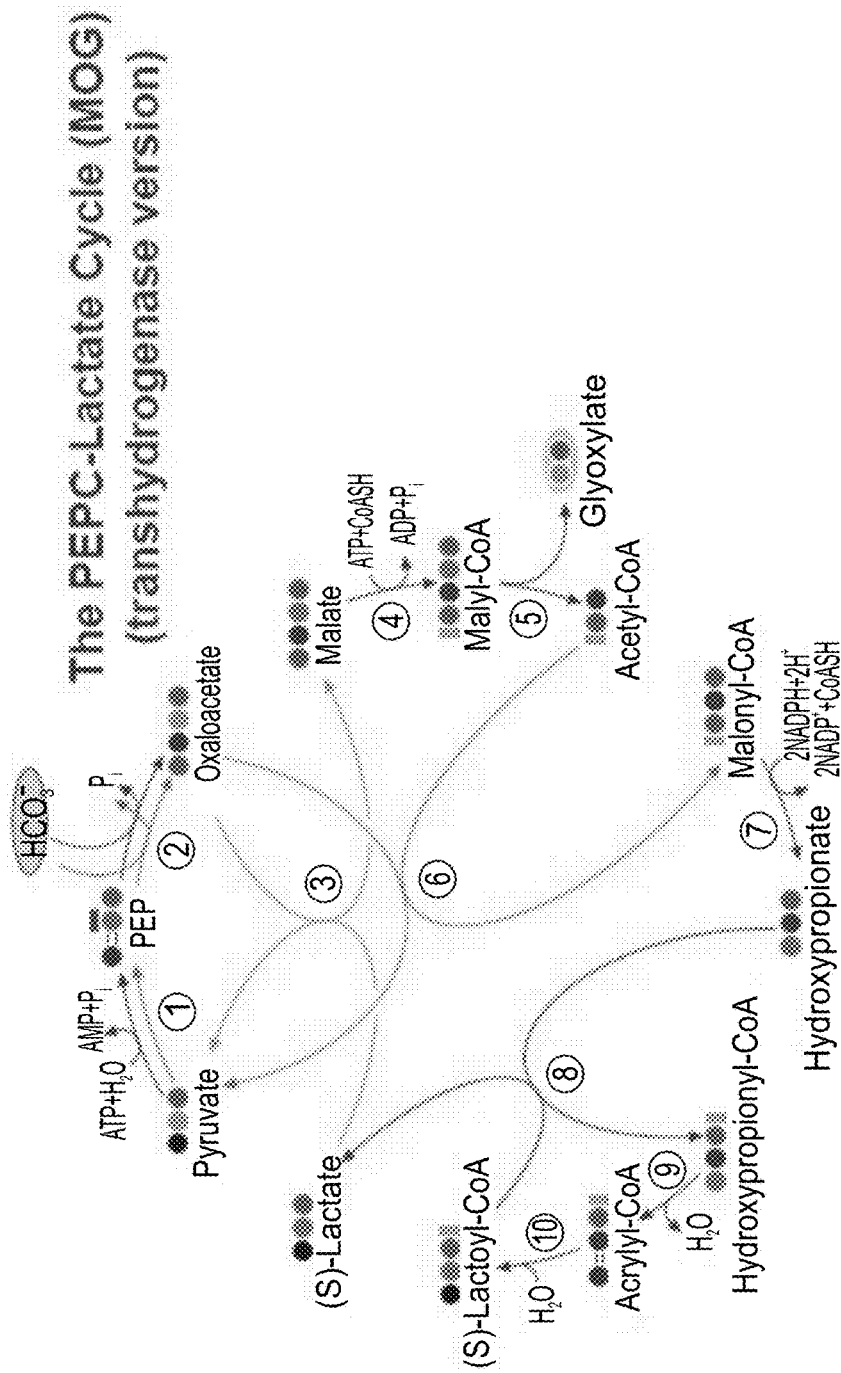

FIG. 16 is a diagram of a carbon fixation pathway according to embodiments of the present invention. In this pathway, the enzyme lactate-malate transhydrogenase (EC 1.1.99.7) is used, that couples the oxidation of lactate with the reduction of oxaloacetate.

Enzymes in the scheme: (1) Pyruvate Dikinase, (2) PEP Carboxylase, (3) Lactate-Malate Transhydrogenase, (4) Malyl-CoA Synthetase, (5) Malyl-CoA Lyase, (6) Methlmalonyl-CoA Carboxytransferase, (7) Malonyl-CoA Reductase, (8) Propionate CoA Transferase, (9) Enoyl-CoA Hydratase, (10) Lactoyl-CoA dehydratase.

Figure 17:
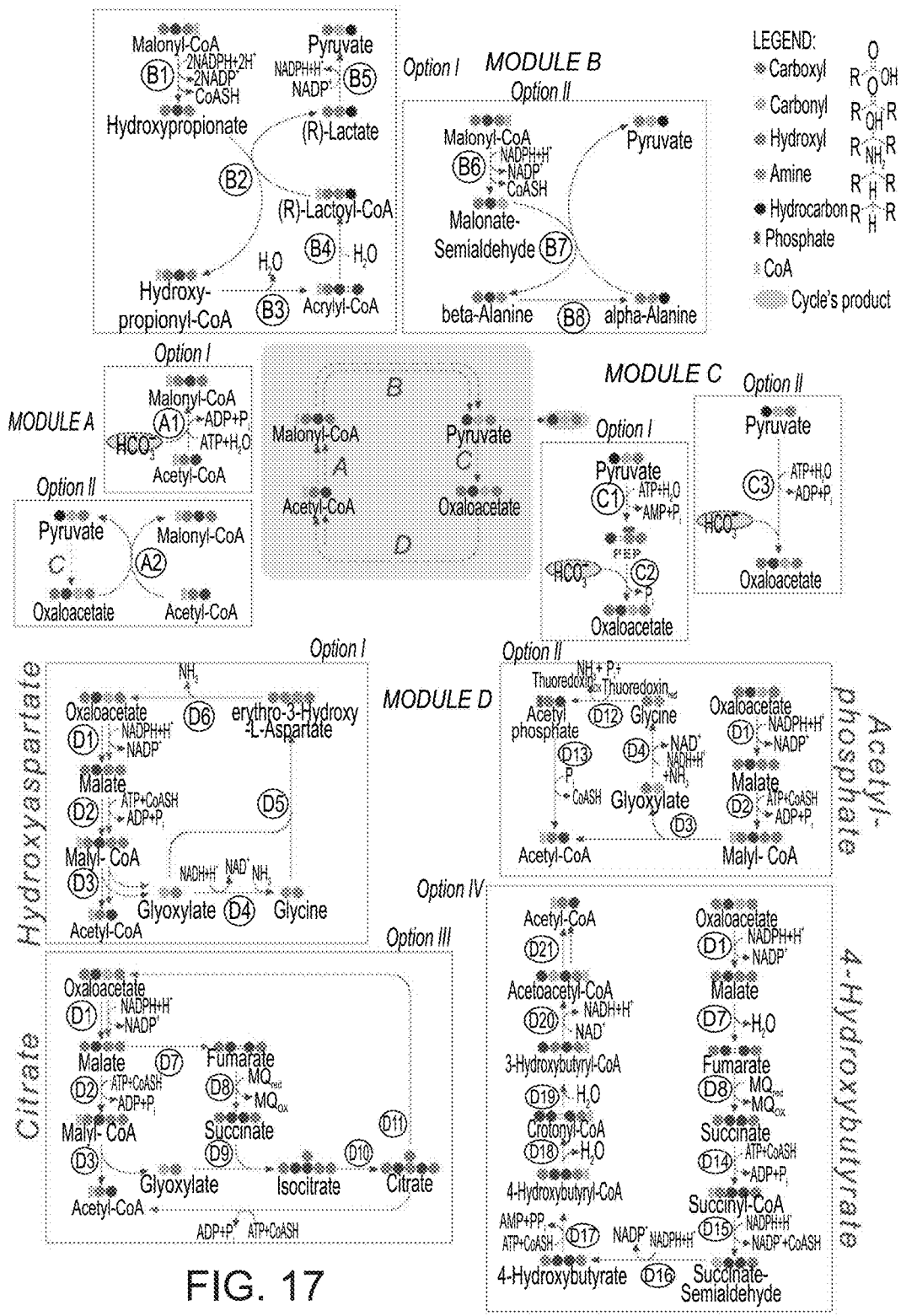

FIG. 17 is a diagram illustrating carbon fixation pathways according to embodiments of the present invention, in which inorganic carbon is fixed to pyruvate. The four common metabolites in all are acetyl-CoA, malonyl-CoA, pyruvate and oxaloacetate. The different modules and options are given in the attached scheme.

Enzymes in the scheme: (A1) Acetyl-CoA Carboxylase, (A2) Methlmalonyl-CoA Carboxytransferase, (B1) Malonyl-CoA Reductase, (B2) Propionate CoA Transferase, (B3) Enoyl-CoA Hydratase, (B4) Lactoyl-CoA dehydratase, (B5) Lactate Dehydrogenase, (B6) Malonate Semialdehyde Dehydrogenase, (B7) Beta-Alanine Pyruvate Transaminase, (B8) Alanine Aminomutase, (C1) Pyruvate Dikinase, (C2) PEP Carboxylase, (C3) Pyruvate Carboxylase, (D1) Malate Dehydrogenase, (D2) Malyl-CoA Synthetase, (D3) Malyl-CoA Lyase, (D4) Glycine Dehydrogenase, (D5) 3-Hydroxyaspartate Aldolase, (D6) erythro-3-hydroxyaspartate ammonia-lyase, (D7) Fumarate Hydratase, (D8) Fumarate Reductase, (D9) Isocitrate Lyase, (D10) Aconitase, (D11) ATP-Citrate Lyase, (D12) Glycine Reductase, (D13) Phosphate Acetyltransferase, (D14) Succinate Thiokinase, (D15) Succinyl-CoA Reductase, (D16) Succinate Semialdehyde Reductase, (D17) 4-Hydroxybutyryl-CoA Synthetase, (D18) 4-Hydroxybutyryl-CoA Dehydratase, (D19) Crotonyl-CoA Hydratase, (D20) 3-Hydroxybutyryl-CoA Dehydrogenase and (D21) Acetoacetyl-CoA β-Ketothiolase.

Figure 18:
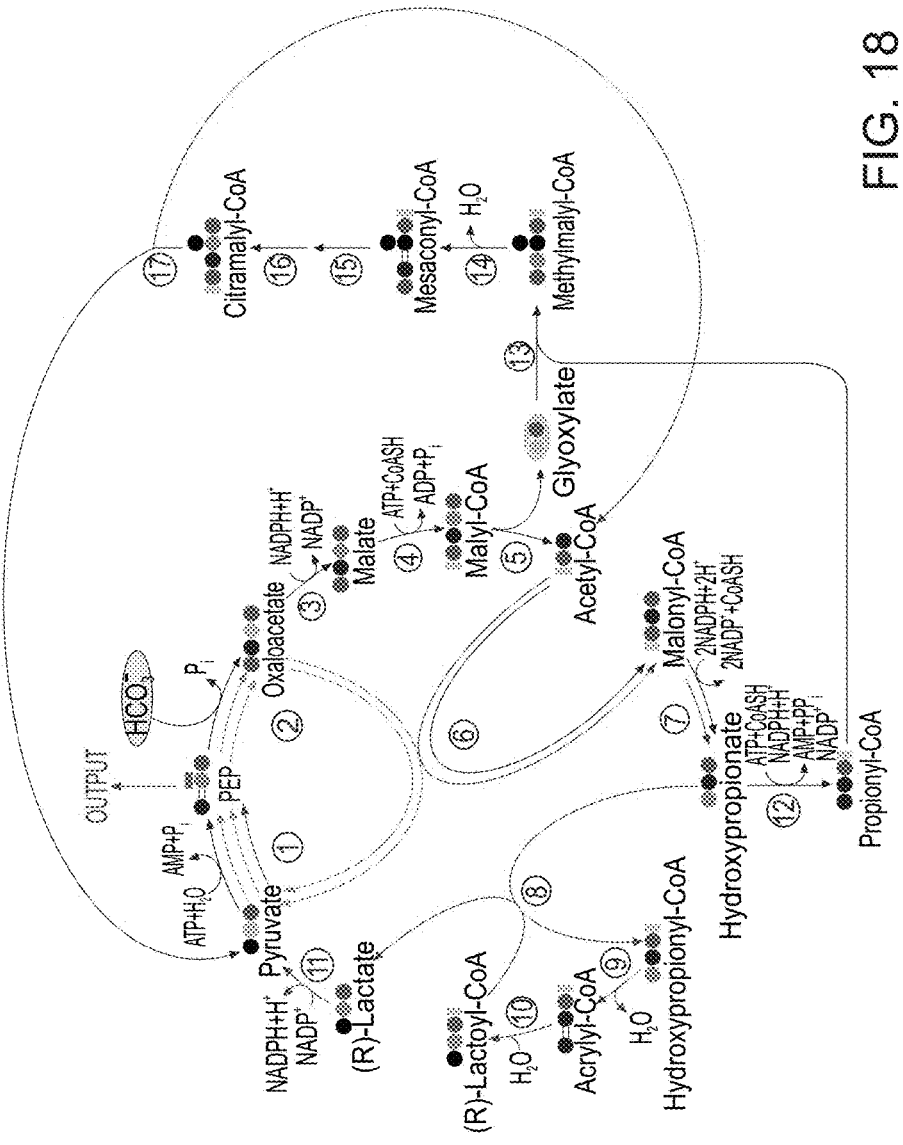

FIG. 18 is a diagram of a PEPC-lactate/citramalate pathway according to embodiments of the present invention.

Enzymes for the PEPC-Lactate/Citramalate pathway: (1) Pyruvate Dikinase, (2) PEP Carboxylase, (3) Malate Dehydrogenase, (4) Malyl-CoA Synthetase, (5) Malyl-CoA Lyase, (6) Methlmalonyl-CoA Carboxytransferase, (7) Malonyl-CoA Reductase, (8) Propionate CoA Transferase, (9) Enoyl-CoA Hydratase, (10) Lactoyl-CoA dehydratase, (11) Lalate Dehydrogenase, (12) Propionyl-CoA Synthethase, (13) L-malyl-CoA lyase, (14) B-methylamalyl-CoA lyase, (15) Mesaconyl-CoA C1-C4 Coa Transferase (16) Mesaconyl-C4-Coa Hydratase and (17) Citramalyl-CoA Lyase.

DESCRIPTION OF SPECIFIC EMBODIMENTS OF THE INVENTION

The present invention, in some embodiments thereof, relates to enzymatic systems for carbon fixation and methods of generating same.

Before explaining at least one embodiment of the invention in detail, it is to be understood that the invention is not necessarily limited in its application to the details set forth in the following description or exemplified by the Examples.

The invention is capable of other embodiments or of being practiced or carried out in various ways.

Carbon fixation is the process by which carbon dioxide is incorporated into organic compounds. In the process of transforming sunlight into biological fuel, plants absorb carbon dioxide using over 70% of the fresh water utilized by humanity and the majority of cultivatable land resources on earth. These figures point to the central place that carbon fixation by plants plays in our global ecological footprint.

Carbon fixation in plants and algae is achieved by the Calvin-Benson Cycle. The productivity of the Calvin-Benson cycle is limited, under many conditions, by the slow rate and lack of substrate specificity of the carboxylating enzyme Rubisco. Several lines of evidence indicate that in-spite of its shortcomings, Rubisco might already be naturally optimized and hence its potential for improvement is very limited. As carbon fixation has been shown to limit growth rate in many studies, the present inventors sought to develop alternative pathways that can support carbon fixation with a higher rate in the efforts towards sustainability.

The present inventors systematically explored the space of possible synthetic carbon fixation pathways that can be assembled from all ~4000 known metabolic enzymes. The present inventors designed this computational search using a constraint-based modeling framework that analyzed the possible metabolic pathways based on physicochemical criteria that include topology, energetics and kinetics.

Whilst reducing the present invention to practice, the present inventors uncovered synthetic cycles with potential for superior characteristics over natural ones. In particular, the present inventors found a new family of carbon fixation pathways that makes use of the most effective carboxylating enzyme, PEP carboxylase, and of the metabolic module used in the efficient C4 plants (see FIGS. 4A-B and FIG. 8)

The present inventors propose implementing these pathways in various systems (cellular and non-cellular) and ultimately in photosynthetic organisms including cyanobacteria (e.g. *Synechococcus*), algae (e.g. *Chlamydomonas*) and higher plants (e.g. *Arabidopsis*, Tobacco).

Thus, according to one aspect of the present invention there is provided a system for carbon fixation, comprising enzymes which catalyze reactions of a carbon fixation pathway, wherein at least one of the reactions of the carbon fixation pathway is a carboxylation reaction, wherein products of the reactions of the carbon fixation pathway comprise oxaloacetate and malonyl-CoA, wherein an enzyme which performs the carboxylation reaction is selected from the group consisting of phophoenolpyruvate (PEP) carboxlase, pyruvate carboxylase and acetyl-CoA carboxylase and wherein an additional product of the carbon fixation pathway is glyoxylate.

The term "carbon fixation" as used herein refers to a process through which gaseous carbon dioxide is converted into a solid compound.

As used herein the phrase "carbon fixation pathway" refers to a set of molecules (e.g. enzymes, electron donors, co-factors etc.) that together enable autotrophic carbon fixation. As such the system of this aspect of the present invention comprises enzymes which are positioned relative to one another such that they are able to function to cause carbon fixation.

The term "enzyme" as used herein refers to a "catalytically functional biomolecule," which includes both whole native (or native-size) molecules and derivatives (e.g. genetic modifications) thereof.

Details of contemplated enzymes to be used according to this aspect of the present invention are provided in FIG. 14.

According to this aspect of the present invention at least one of the reactions in the pathway is a carboxylating reaction.

The term "carboxylation reaction" refers to a reaction in which in which an in-organic carbon is introduced into a substrate to become a carboxylic acid group.

Enzymes capable of performing carboxylating reactions are provided in FIG. 13. According to this aspect of the present invention at least one of the enzymes of the carbon fixation pathway is phophoenolpyruvate (PEP) carboxlase, pyruvate carboxylase or acetyl CoA carboxylase.

According to a particular embodiment of this aspect of the present invention the carboxylating enzyme is PEP carboxylase.

According to one embodiment, two of the reactions of the pathway are carboxylating reactions.

According to still another embodiment, one of the reactions of the pathway is a transcarboxylating reaction.

The term "transcarboxylation reaction" refers to a reaction in which a carboxylic acid group is transferred from one metabolite to another one.

An Exemplary enzyme contemplated for the transcarboxylating reaction is methylmalonlyl-CoA carboxytransferase.

As used herein, the phrase "export product" refers to a product of one (or more) of the reactions of the carbon fixation pathway which does not serve as a substrate for the other enzymes of the pathway.

According to one embodiment, the export product is glyoxylate.

According to another embodiment, the export product is pyruvate.

According to this aspect of the present invention, the pathway specific activity is greater than 0.3 µmol-GA3P/min/mg. The pathway specific activity (analogous to an enzyme's specific activity) is defined to be the maximal rate of glyceraldehyde-3-phosphate (GA3P) formation by 1 mg of pathway total protein—as detailed in Example 2 herein below.

Exemplary carbon fixation pathways of the present invention which have glyoxylate as the export product are illustrated in FIGS. 4A-B, FIG. 8 and FIG. 16.

Exemplary carbon fixation pathways of the present invention which have pyruvate as the export product are illustrated in FIGS. 17 and 18.

According to one embodiment, the enzymes of the carbon fixation pathways of the present invention are expressed in cells. The cells may be eukaryotic (e.g. plant cells) or prokaryotic (e.g. bacterial cells). Such cells include cells of photosynthetic organisms (cyanobacteria, algae and higher plants), chemosynthetic organisms, and non-autotrophic organisms (e.g. *E. coli*). According to this embodiment the enzymes which take part in the carbon fixation pathways are present in the same component of the cell such that they are able to cooperate together to fulfill their role in the carbon fixation pathways.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantee, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used for the methods of the present invention.

It will be appreciated that the number of additional enzymes which have to be exogenously expressed in a particular cell will depend on the enzymes which are naturally expressed in that cell type and on the sub-cellular location thereof.

In addition, depending on the system selected for carbon fixation, other factors must be generated or expressed in the system to ensure a sufficient energy supply. Thus, for example in a non-cellular system ATP and NADH and/or NADPH should be provided as detailed further below. In *E. coli*, NAD is the preferred intermediate electron acceptor because it can directly serve both as an electron donor for carbon fixation and as an energy producer when oxidized by *E. coli*'s respiratory electron chain. The two best candidates for providing *E. coli* with reducing power (and energy) are formate and phosphite. The soluble enzyme NAD$^+$-dependent formate dehydrogenase irreversibly oxidizes formate ($E'^0$=−430 mV) and reduces NAD$^+$-formate cannot be directly assimilated by *E. coli*. NAD:phosphite oxidoreductase irreversibly oxidizes phosphite to phosphate ($E'^0$=−650 mV) and reduces NAD$^+$.

Example 3 lists the specific enzymes and factors required to be expressed/combined in 4 exemplary organisms—*E. coli*; *Synechocystis* sp. strain PCC6803 (cyanobacteria); *Chlamydomonas reinhardtii* (algae); Tobacco (*Nicotiana*) plant and in a non-cellular system.

To express the enzymes of the present invention using recombinant technology, a polynucleotide encoding the enzymes is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

Thus, the present invention contemplates isolated polynucleotides encoding the enzymes of the present invention.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exon sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

As mentioned hereinabove, polynucleotide sequences of the present invention are inserted into expression vectors (i.e., a nucleic acid construct) to enable expression of the recombinant polypeptide. The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

According to one embodiment of this aspect of the present invention, the polynucleotides of the present invention are expressed in cells of a photosynthetic organism (e.g. higher plant, algae or cyanobacteria).

Examples of constitutive plant promoters include, but are not limited to CaMV35S and CaMV19S promoters, tobacco mosaic virus (TMV), FMV34S promoter, sugarcane baculiform badnavirus promoter, CsVMV promoter, *Arabidpsis*

ACT2/ACT8 actin promoter, *Arabidpsis ubiquitin* UBQ 1 promoter, barley leaf thionin BTH6 promoter, and rice actin promoter.

An inducible promoter is a promoter induced by a specific stimulus such as stress conditions comprising, for example, light, temperature, chemicals, drought, high salinity, osmotic shock, oxidant conditions or in case of pathogenicity. Examples of inducible promoters include, but are not limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr2O3J and str246C active in pathogenic stress.

These constructs can be introduced into plant cells using Ti plasmid, Ri plasmid, plant viral vectors, direct DNA transformation, microinjection, electroporation, Biolistics (gene gun) and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

According to one embodiment, the enzymes of the present invention are expressed with chloroplast targeting peptides.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J. Bioenerg. Biomemb. 22(6):789-810); tryptophan synthase (Zhao et al. (1995) J. Biol. Chem. 270(11):6081-6087); plastocyanin (Lawrence et al. (1997) J. Biol. Chem. 272 (33):20357-20363); chorismate synthase (Schmidt et al. (1993) J. Biol. Chem. 268(36):27447-27457); and the light harvesting chlorophyll a/b binding protein (LHBP) (Lamppa et al. (1988) J. Biol. Chem. 263:14996-14999). See also Von Heijne et al. (1991) Plant Mol. Biol. Rep. 9:104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Plant cells may be transformed stabley or transiently with the nucleic acid constructs of the present invention. In stable transformation, the nucleic acid molecule of the present invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

It will be appreciated that any of the construct types used in the present invention can be co-transformed into the same organism (e.g. plant) using same or different selection markers in each construct type. Alternatively the first construct type can be introduced into a first plant while the second construct type can be introduced into a second isogenic plant, following which the transgenic plants resultant therefrom can be crossed and the progeny selected for double transformants. Further self-crosses of such progeny can be employed to generate lines homozygous for both constructs.

As mentioned the components of the systems of the present invention may also be combined in non-cellular particles or reactors.

As used herein, the term "combining" refers to any method where the components are in close enough proximity that carbon fixation may occur. Thus, the term "combining" incorporates such methods as co-expressing and co-solubilizing the components of the present invention.

It will be appreciated that in a non-cellular system the components of the carbon fixation pathway are typically expressed in host cells and following a predetermined time in culture, recovery of the recombinant polypeptide (enzyme) is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, salting out (as in ammonium sulfate precipitation), affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The polypeptide of the present invention is preferably retrieved in "substantially pure" form.

As used herein, the phrase "substantially pure" refers to a purity that allows for the effective use of the protein in the applications described herein.

In addition to being synthesizable in host cells, the polypeptide of the present invention can also be synthesized using in vitro expression systems. These methods are well known in the art and the components of the system are commercially available.

As mentioned, to support carbon fixation in a non-cellular system, the enzymatic system should be provided with energized cofactors, namely ATP and NADH and/or NADPH. These cofactors can be regenerated in vitro in various ways (Wichmann R & Vasic-Racki D (2005) (Springer Berlin/Heidelberg), Vol 92, pp 225-260).

In one embodiment, the pathway components of the present invention are combined in a carrier system (i.e., encapsulating agent) of desired properties. In a specific embodiment, the encapsulating agent is a liposome.

As used herein and as recognized in the art, the term "liposome" refers to a synthetic (i.e., not naturally occurring) structure composed of lipid bilayers, which enclose a volume. Exemplary liposomes include, but are not limited to emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3):35-43]. The liposomes may be positively charged, neutral, or, negatively charged.

The liposomes may be a single lipid layer or may be multilamellar. Surfactant peptide micelles are also contemplated.

In another embodiment, the pathway components of the present invention are embedded in a carrier (i.e., embedding agent) of desired properties. In specific embodiments, the embedding agent (or carrier) is a microparticle, nanoparticle, nanosphere, microsphere, nano-plate, microcapsule, or nanocapsule [M. Donbrow in: Microencapsulation and Nanoparticles in Medicine and Pharmacy, CRC Press, Boca Raton, Fla., 347, 1991]. The term carrier includes both polymeric and non-polymeric preparations. According to a specific embodiment, the embedding agent is a nanoparticle. The polypeptides of the present invention may be embedded in the nanoparticle, dispersed uniformly or non-uniformly in the polymer matrix, adsorbed on the surface, or in combination of any of these forms. Polymers which may be used for fabricating the nanoparticles include, but are not limited to, PLA (polylactic acid), and their copolymers, polyanhydrides, polyalkyl-cyanoacrylates (such as polyisobutylcyanoacrylate), polyethyleneglycols, polyethyleneoxides and their derivatives, chitosan, albumin, gelatin and the like.

It will be appreciated that the enzymes of the present invention and the electron donor need not be encapsulated. Thus, according to yet another embodiment, the enzymes and the electron donor of the present invention are free in solution.

In yet embodiment, the pathway components of the present invention are combined in a reactor of desired properties. Exemplary reactors include, but are not limited to a test-tube, a container, a bioreactor and a vessel.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental or calculated support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Pathway Analysis Metrics Enable a Comprehensive Comparison Between Pathways

Many different aspects of a given metabolic pathway are important for its function. To enable evaluation and comparison of metabolic pathways, the present inventors have used several parallel criteria.

The pathway specific activity (criterion I) is analogous to an enzyme's specific activity and is defined to be the maximal rate of product formation by 1 mg of pathway total protein (see Example 2 for the exact calculation). The pathway specific activities for all natural carbon fixation pathways have been calculated and are presented in FIG. 12, Table 1 (marked in blue).

These pathways, as well as the other that were analyzed in Example 2 (including the natural pathways) are annotated and grouped according to their main metabolic characteristics, i.e., the carboxylating enzymes that create their "metabolic core". Aside from those enzymes, a pathway is generally annotated according to an indicative metabolite that does not participate in other pathways sharing the same carboxylating enzymes. For example, the MOG pathways (FIG. 8) are marked as PEPC, PyrC, PEPC-AcC or PyrC-AcC depending on the carboxylating enzymes used by the specific MOG variant. The indicative metabolites are alanine or lactate, depending on the 'bypass' taken (module C in FIG. 8).

Table 1 (FIG. 12) is divided according to several criteria. The main division is between ferredoxin-oxidoreductase-containing and non-ferredoxin-oxidoreductase pathways. The ferredoxin-oxidoreductase enzymes present two main difficulties: they are extremely oxygen sensitive and the rate of carboxylation they support is generally un-known. Because one cannot obtain reliable information regarding their enzymatic rates they were not included in the pathway specific activities calculation. Therefore, the pathways containing those enzymes have an artificially higher specific activity and cannot be compared to the non-ferredoxin-oxidoreductase-containing pathways.

The natural pathways are given at the beginning of each section and are marked in blue. Throughout the text and in Table 1, FIG. 12 the following abbreviations for the carboxylating enzymes are used: AcC: acetyl-CoA carboxylase; CCR: crotonyl-CoA carboxylase/reductase; ICDH: isocitrate dehydrogenase; KGC: 2-ketoglutarate carboxylase; KGS: 2-ketoglutarate synthase; ME: 'malic' enzyme; MCC: methylcrotonyl-CoA carboxylase; PEPC: PEP carboxylase; PrC: propionyl-CoA carboxylase; PyrC: pyruvate carboxylase and PyrS: pyruvate synthase.

The ubiquitous rPP cycle has a pathway specific activity of 0.25 μmole/min/mg (taking into account oxygenase activity), a value that will be used as a benchmark for evaluation of the kinetics of the synthetic pathways (the conditions under which this criterion reflects the pathway flux are detailed and elaborated in Example 2 herein below).

While the kinetics of a pathway is of central importance it does not provide any information regarding the cellular resources it consumes. Different pathways, which ultimately perform the same metabolic conversation, might consume the different resources of the cell to a different measure, thereby unequally affecting the organism growth. The present inventors focus on the energetic cost (criterion II) associated with the different pathways, corresponding to the efficiency of using the light-regenerated resources of the cell. The energetic cost can be separated into two terms:

NADPH cost: the number of moles of NADPH equivalents (i.e. redox carriers, such as NAD(P)H, ferredoxins and $FADH_2$) consumed in the production of one mole of product (GA3P).

ATP cost: The number of moles of ATP equivalents (non-redox energy carriers, e.g. NTPs, phosphate esters and coenzyme A thioesters) consumed in the production of one mole of product.

The NADPH and ATP costs of all natural carbon fixation pathways are given in FIG. 12, Table 1.

The energetic cost of a pathway can be used to determine the energetic feasibility of the pathway as a whole as well as any of its parts. A thermodynamicaly favorable (criterion III) pathway is one for which the free energy change ($\Delta G^r$) associated with the production of one mole of product is negative. A negative free energy change is also required to be obtained for each part of the pathway under physiological range of metabolite concentrations (See Example 2).

In order to ensure thermodynamic feasibility, a carbon fixation pathway must involve the hydrolysis of a certain minimal amount of ATP molecules. Yet, hydrolysis of too many ATP molecules will decrease the energetic efficiency (increase the energetic cost) considerably. This minimal ATP requirement depends on the identity of the different electron donors utilized by the pathway, on the pH and on the ionic strength (Alberty R A (2003) Thermodynamics of Biochemical Reactions (Wiley-Interscience)). In FIG. 2A, the minimal ATP requirement of the prevalent rPP pathway in physiological ionic strengths and pH values is analyzed, where all the electron donors are NAD(P)H and under ambient $CO_2^{gas}$ concentration of ~390 ppm. As the figure shows, 5-6 ATPs are minimally required (see Example 2). It may be further noted that the rPP uses 9 ATPs in order to support carbon fixation under ambient conditions; the extra ATP molecules consumed are suggested to enhance its kinetics at the expense of its ATP efficiency.

Figure 2:
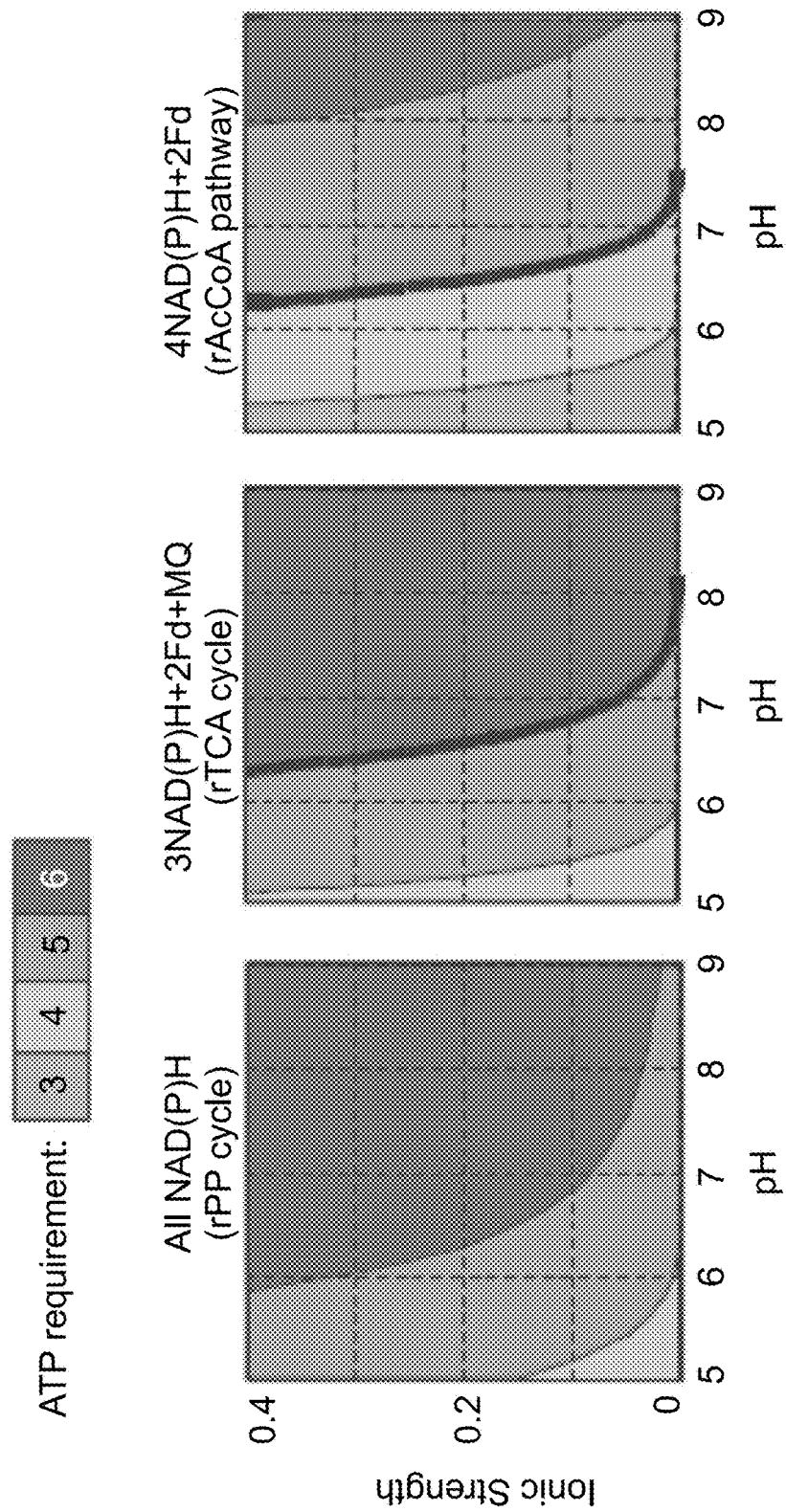

Different electron donors, other than NAD(P)H, with lower (i.e. more energetic, e.g. ferredoxin) or higher (e.g. menaquinone) reduction potentials would shift this thermodynamic profile (Example 2). FIGS. 2B and C show the minimal ATP requirement for the rAcCoA pathway and the rTCA cycle, which utilize these electron donors. Interestingly, although these pathways are potentially more efficient (hydrolyzing only 4-5 ATPs), it may be concluded that they are not feasible at pH values higher than 7 under ambient $CO_2$ concentrations (bold lines correspond to the feasibility ranges in FIG. 2). These results are in agreement with the observation that organisms that operate the rTCA cycle or the rAcCOA pathway usually occupy high $CO_2$ habitats or operate a carbon concentrating mechanism (FIG. 10B). These organisms are generally anaerobic and energy restricted as compared to aerobes, which limits their available energy for investment in carbon fixation. Hence, they prefer the utilization the rTCA cycle or the rAcCOA pathway that are more ATP efficient than the rPP cycle.

While the kinetics and the energetics of a pathway provide valuable information concerning its function, there are several other factors that can further aid in the assessment and comparison of the different metabolic alternatives. Of these, the present inventors addressed the topology (criterion IV), corresponding to the internal makeup of a pathway and its integration with the structure of the metabolic network of the cell. The topology criterion incorporates two important parameters:

Number of enzymes (simplicity): The number of enzymes the carbon fixation cycle utilizes as an independent unit, as well as the number of enzymes the complete pathway employs (including the conversion of the cycle's product into triose-phosphate).

Metabolic compatibility of the synthetic pathways: In designing alternative $CO_2$ assimilation pathways, it is important to consider how the pathways will integrate into the endogenous metabolic network. The present inventors have used a model of central carbon metabolism in the algae *Chlamydomonas* and employed constrained-based analysis (i.e., flux balance analysis (FBA) and uniform random sampling (Schellenberger J & Palsson B O (2009) *J Biol Chem* 284(9):5457-5461)) to test the compatibility of each cycle with the endogenous metabolic network (Lewis N E, et al (2009) Metabolic Systems Biology: A Constraint-Based Approach. Encyclopedia of Complexity and Systems Science). The present inventors have calculated the growth yield supported by each pathway as well as the number of significantly changed fluxes in the modified network as compared to the wild-type model (See Example 2).

A Systematic Method to Locate Novel Synthetic Carbon Fixation Pathways Reveals the Simplest Carbon Fixation Cycles The present inventors have developed a novel computational approach (see Example 2) to systematically explore all the possibilities to build carbon fixation cycles of a given size that utilize the ~4000 enzymes reported in the KEGG database. Each candidate cycle employs one or more carboxylating enzymes and produces an organic output compound with at least two carbons. This exhaustive search enables covering a space of possibilities which was next analyzed for its feasibility and functionality using the criteria detailed above.

The analysis was started by exploring what are the synthetic carbon fixation pathways which employ the simplest (shortest) cycles. Such pathways can be a priori suggested to be attractive in terms of rate. Several pathways were found that employ cycles with merely four to six enzymatic steps (FIGS. 7A-G). FIG. 3 presents one of the three cycles that utilizes only four enzymes. This cycle is a metabolic shortcut of the naturally occurring rTCA cycle; three of its enzymes participate in the rTCA cycle and the enzyme isocitrate lyase metabolically bypasses the rest of the natural cycle. The product of this simple cycle, glyoxylate, is converted to GA3P by the bacterial-like glycerate pathway (Kebeish R, et al. (2007), *Nat Biotechnol* 25(5): 593-599) (FIG. 6).

However, this as well as the other pathways that employ such ultra-short cycles, suffer from a fundamental fault. Most cycles, as distinct metabolic units that produce glyoxylate, are not thermodynamically feasible, taking into account the physiologically relevant glyoxylate concentrations (see Example 2). In addition, all use an oxygen-sensitive ferredoxin-oxidoreductase enzyme (pyruvate synthase or 2-ketoglutarate synthase) and have a significantly lower pathway specific activity, as compared to the rTCA cycle (see FIG. 12, Table 1).

Novel Kinetically Efficient Carbon Fixing Pathways Utilizing the Most Attractive Carboxylating Enzymes The design of kinetically efficient pathways requires the utilization of high carboxylating enzymes, which result from having high specific activities and affinities towards $CO_2$ or $HCO_3^-$. A wide literature survey was performed and kinetic properties of known carboxylating enzymes were compared as presented in FIG. 13, Table 2.

Phosphoenolpyruvate carboxylase (PEPC) and pyruvate carboxylase are the most favorable carboxylating enzymes; both have high specific activities and superior affinity for $HCO_3^-$. Acetyl-CoA and Propionyl-CoA carboxylases are the next favorable. These four enzymes prefer carboxylation over decarboxylation. Isocitrate dehydrogenase, which prefers decarboxylation under common physiological conditions, is also a kinetically acceptable option. All other carboxylating enzymes are rather slow under ambient $CO_2$/$HCO_3^-$ concentrations (specific activity <2 μmol/min/mg).

The present inventors used a systematic search tool to find the shortest pathways that employ different sets of the favorable carboxylating enzymes (Example 2). The present inventors have numerically predicted which of these pathways is best in terms of pathway specific activity. Notably it was found that all the pathways with the highest specific activities employ similar cycles, with a shared metabolic core structure (FIG. 8). The product of those cycles, glyoxylate, is assimilated by the bacterial-like glycerate pathway. This family of pathways has been termed the Malonyl-CoA-Oxaloacetate-Glyoxylate (MOG) pathways. It has been found that the MOG pathways have 2-3 fold higher pathway specific activity as compared to the rPP cycle (FIG. 12, Table 1). FIGS. 4A-B present two MOG pathways that employ only one carboxylating enzyme, the superior PEP carboxylase. These MOG pathways have been termed the C4-Glyoxylate cycles, because they converge with the naturally evolved C4 mechanism (FIG. 4C).

In C4 plants carbon is temporarily fixed, in the mesophyll cells, by the carboxylation of PEP to oxaloacetate. This is followed by the reduction of oxaloacetate to malate. Malate is then transported to the bundle-sheath cells where it releases the $CO_2$, which is re-assimilated by Rubisco. Pyruvate is recycled to complete the cycle which serves as a "futile cycle" that concentrates $CO_2$ (Nelson D L & Cox M M (2004) *Lehninger Principles of Biochemistry* (W. H. Freeman & Co.). All of these reactions, with the exception of decarboxylation, appear in the C4-Glyoxylate cycle. Therefore, the C4-Glyoxylate cycles are an alternative for completing the C4 cycle without "losing" the carbon: replacing the "futile" decarboxylation reaction with an extra carboxylation, accompanied with the export of glyoxylate.

There are several possible variations on the C4-Glyoxylate cycles (FIG. 8) each having possible pros and cons. Using Pyruvate carboxylase instead of PEP carboxylase results in higher ATP efficiency but somewhat lower pathway specific activity (FIG. 12, Table 1). In addition, acetyl-CoA carboxylase, another efficient carboxylating enzyme, can be used instead of the carboxytransferase enzyme (denoted as #6 in FIG. 4). FIG. 12, Table 1 presents a comprehensive comparison between all the MOG pathways.

The MOG pathways are equivalent to the rPP cycle in their electron donors usage; all donors are NAD(P)H. Hence, FIG. 2A presents the ATP requirement for the MOG pathways as well. These pathways hydrolyze 8-12 ATP molecules (depending on the exact pathway identity, see Example 2) and therefore are all thermodynamically feasible, with ΔG<<0 under a wide range of pH and ionic strengths.

Using the central carbon metabolism model of the algae *Chlamydomonas* it was found that the MOG pathways were able to support maximal growth yield with no further secretion products. Moreover, the flux solution space indicates that the integration of the MOG cycles necessitates the fewest significant changes in the endogenous flux distributions in comparison to. (Example 2).

Most reactions employed by the MOG pathways are prevalent in many species throughout the tree of life. Yet, some reactions involved in these pathways are rather unique. For example, the reduction of malonyl-CoA (reaction 7 in FIGS. 4A and B) can be performed by an enzyme found only from thermophilic prokaryotes (Alber B, et al. (2006), *J Bacteriol* 188(24):8551-8559). In addition, the hydration of acrylyl-CoA (reaction 10 in FIG. 4B) is carried out by the enzyme lactoyl-CoA dehydratase that contains iron-sulfur centers and was found to be oxygen sensitive (Kuchta R D & Abeles R H (1985) *J Biol Chem* 260(24):13181-13189). Nevertheless, early studies indicate that there exist variants of the enzyme, from various organisms, that show efficient performance under full aerobic conditions (e.g. Baldwin R L, Wood W A, & Emery R S (1965) *Biochim Biophys Acta* 97:202-213)). Finally, the enzyme alanine aminomutase (reaction 9 in FIG. 4A) was evolved from the enzyme lysine 2,3-aminomutase to act on alanine (Liao H H, Gokarn R R, Gort S J, Jessen H J, & Selifonova O (2007) U.S. Pat. No. 7,309,597 B2.). A comprehensive discussion on the unique enzymes of the C4-Glyoxylate cycles is given in Example 2.

Other promising synthetic carbon fixation pathways that resulted from the present analysis are discussed in Example 2 (FIGS. 9A-N and FIG. 12, Table 1). Notably, many of the synthetic pathways are expected to be faster than the rPP cycle (i.e., they have higher calculated pathway specific activities).

Analysis and Optimization of Carbon Fixation Pathways

This study used a novel methodology to computationally analyze and compare carbon fixation pathways, by focusing on their kinetics. It was found that synthetic pathways have the potential to show significantly faster kinetics as evaluated by the pathway specific activity. From a biotechnological point of view, this criterion is probably a major one, directly affecting the productivity of a photosynthetic, carbon fixing organism. Importantly, under ambient conditions and average illumination, the ATP and NADPH costs are suggested to rarely be a limiting factor (Holt N E, Fleming G R, & Niyogi K K (2004) Biochemistry 43(26):8281-8289). As shown in the present analysis the NADPH costs of all natural and synthetic pathways are the same (FIG. 12, Table 1), corresponding to the fact that the same number of electrons is required to reduce inorganic carbon to GA3P regardless of the exact metabolic path. Notably, the NADPH cost of the rPP cycle, which includes photorespiration, is higher because some of the electrons are used by glycolate oxidase to reduce molecular oxygen into $H_2O_2$.

The overall flux through a pathway is approximated by the pathway specific activity criterion when: (1) the enzymes are substrate saturated, (2) the rate of the backward reaction of each enzyme is negligible compared to the rate of its forward reaction and (3) enzyme expression levels are balanced based on each enzyme's specific activities (no 'surplus' of any enzyme). Obviously, in natural pathways none of these requirements fully holds; therefore the pathway specific activity serves as an upper limit estimation of the pathway overall rate (Example 2). It is used only as a useful, well-defined proxy which enables calculation and comparison with the limited available kinetic data. This metric is not biased and thus the advantage of the synthetic alternatives over the natural pathways is expected to hold even if the overall rates would be lower than predicted.

Several other optimization methods have been discussed in the literature, based on minimization of overall metabolic intermediate concentration, minimization of transient times, and maximization of enzyme specificity (Heinrich R, Schuster S, & Holzhutter H G (1991) *Eur J Biochem* 201(1):1-21). However, most of these cannot be systematically employed due to the lack of necessary data.

In this study, the present inventors have referred explicitly only to the efficiency of using ATP-like and NADPH-like resources, both regenerated by light. In reality, however, the water usage efficiency, the nitrogen usage efficiency and others are just as important even in human cultivated environment. It is important to note, however, that utilizing a carbon fixation pathway with increased productivity is expected to have a considerable positive effect on these efficiencies as well. For example, higher specific rate of carbon fixation will enable the cell to better reallocate its resources, e.g. dedicate less protein for carbon fixation, which in turn will increase the nitrogen use efficiency (photosynthetic rate per unit of N, [Sage R F & Pearcy R W (1987) *Plant Physiol* 84(3):959-963). In addition, the increased affinity towards inorganic carbon and the absence of the oxygenation reaction will enable the plant to sustain a high carbon fixation rate even when a high fraction of the pores are closed, which in turn will increase the water use efficiency.

Example 2

In the present example a comprehensive view of the synthetic carbon pathways discovered using the described search is provided.

General Aspects of the Synthetic Carbon Fixation Pathways

To enable pathway evaluation and comparison in terms of the different criteria, a common pathway product was defined. Glyceraldehyde-3-phosphate (GA3P) was selected as such a metabolite because it is regarded as the product of the reductive pentose phosphate (rPP) cycle (FIG. 5A) and because it is the simplest sugar leading to the bio-synthesis of larger transport metabolites. Each pathway is therefore composed of a cycle and an assimilation sub-pathway which converts the cycle's product into GA3P (FIG. 6). The choice of which compound will serve as the pathway output does not affect the qualitative results discussed here. It may offset the energetic cost or the pathway specific activity but to similar amounts in all pathways. It is thus a useful approach but one that can be changed to a different choice without invalidating the present conclusions.

To ensure the correct forward direction of the metabolic flux through the different pathways, it is important for them to utilize at least one irreversible enzyme. Importantly, all the synthetic pathways proposed in the present examples contain this feature. Such irreversible reactions include PEP carboxylation by PEP carboxylase (as opposed to reversible PEP carboxylation by PEP carboxykinase), glyoxylate self-condensation (forming tartronate-semialdehyde), glycerate phosphorylation, malate decarboxylation and propionyl-CoA formation (acrylyl-CoA reduction).

Importantly, almost none of the proposed cycles are auto-catalytic, as the rPP cycle (the product of an auto-catalytic cycle is also an intermediate of the cycle; as glyceraldehydes-3-phosphate in the case of the rPP cycle). Therefore, the proposed cycles avoid complex regulation that must be imposed in order to maintain appropriate metabolite concentrations in auto-catalytic cycles.

Many proposed synthetic cycles utilize the enzyme PEP carboxylase. PEP carboxylase from C4 plants is known to be light regulated and therefore can serve in switching the cycle activity according to the light exposure.

II. The MOG Pathways: Characteristics and Unique Reactions

A Group of Pathways that have the Highest Calculated Pathway Specific Activity

The present search for synthetic carbon fixation cycles revealed a promising group of pathways. The basic structure of the pathways that belong to this group is shown in FIG. 8. Malonyl-CoA and oxaloacetate are the products of the pathways' carboxylation or transcarboxylation reactions and glyoxylate is the common export product of these pathways. Therefore, this pathway group has been termed the Malonyl-CoA-Oxaloacetate-Glyoxylate (MOG) pathways.

The MOG pathways have the highest calculated pathway specific activities and thus show promise to have the highest rates of carbon fixation among the synthetic carbon fixation pathways. The reason for their suggested superiority is the unique combination of the carboxylating enzymes they utilize. The MOG pathways utilize only the three best carboxylating enzymes: PEP, pyruvate and acetyl-CoA carboxylase. Those three enzymes are characterized by high specific activities under saturating $CO_2/HCO_3^-$ concentrations and by excellent affinities for $HCO_3^-$, which, in turn, give them the highest specific activities, under ambient $CO_2/HCO_3^-$ concentrations, in comparison to all other carboxylating enzymes (see FIG. 13, Table 2).

As shown in FIG. 8, different MOG pathways employ different combinations of these superior carboxylating enzymes. Pyruvate carboxylase can replace PEP carboxylase (options I and II of module C), which results in a decrease in the ATP cost, but also in the pathway specific activity (FIG. 12, Table 1, PyrC and Pyr-AcC, marked in green). Acetyl-CoA carboxylase can be replaced by a transcarboxylase enzyme, coupled with an extra carboxylation of pyruvate/PEP to oxaloacetate (options I and II of module A). In addition, the metabolic conversion of malonyl-CoA to pyruvate can be accomplished by different "bypasses", such as the "alanine bypass" (FIG. 4A) or the "lactate bypass" (FIG. 4B). FIG. 12, Table 1 presents the pathway specific activities calculated for each of those combinations and demonstrate that all of them are expected to be excellent carbon fixation pathways.

FIG. 4 shows the MOG pathways that use PEP carboxylase as their sole carboxylating enzyme. The main advantage of these pathways over their counterparts is having the highest predicted pathway specific activity (FIG. 12, Table 1). They can also have advantages in terms of regulation. PEP carboxylase from C4 plants is known to be light regulated, a mechanism that can be used in the host organism to shut the cycle down when illumination falls below a certain threshold. The light activation of the other C4 enzymes presented in the cycle (pyruvate dikinase and malate dehydrogenase), by similar mechanisms, can support this kind of regulation.

Below reactions which are specific to the 'lactate' and 'alanine' bypasses of the MOG pathways are discussed.

Unique Reactions of the "Alanine Bypass"

The "alanine bypass", converting malonyl-CoA to pyruvate, is shown in FIG. 8, module B, option 2. The two unique reactions in this pathway are the reduction of malonyl-CoA to malonate-semialdehyde and the aminomutase reaction that converts beta-alanine to alpha-alanine.

Two archaeal strains, *Sulfolobus tokodaii* and *Metallosphaera sedula*, were found to employ a unique malonyl-CoA reductase enzyme that catalyzes the reduction of malonyl-CoA to malonate-semialdehyde (reaction 7 in FIG. 4A) (Alber B, et al. (2006) *J Bacteriol* 188(24):8551-8559).

The enzyme alanine aminomutase (reaction 8 in FIG. 4A) reversibly converts beta-alanine to alpha-alanine. This enzyme was evolved from the enzyme lysine 2,3-aminomutase to act on alanine (Prather K L & Martin C H (2008) *Curr Opin Biotechnol* 19(5):468-474; Liao H H, et al (2007) U.S. Pat. No. 7,309,597 B2). Importantly, the *Bacillus subtilis* lysine 2,3-aminomutase was chosen for the cloning and the screening processes. This enzyme, unlike several others that exist in other organisms, is stable in air and remains fully active under aerobic conditions.

Unique Reactions of the "Lactate Bypass"

The "lactate bypass", converting malonyl-CoA to pyruvate, is shown in FIG. 8, module B, option 1. The unique reactions in this pathway are described below:

The reduction of malonyl-CoA to 3-hydroxypropionate (reaction 7 in FIG. 4B) can be performed by the enzyme malonyl-CoA reductase from the green nonsulfur bacterium *Chloroflexus aurantiacus*, which was found to catalyze the two-step reduction of malonyl-CoA to 3-hydroxypropionate (Hugler et al, 2002, *J Bacteriol* 184(9):2404-2410). This enzyme contains two separate domains for the two step reaction: an aldehyde dehydrogenase and an alcohol dehydrogenase. Malonate-semialdehyde, the product of the first reaction, serves as a soluble, free substrate for the second reaction. The optimum temperature of this enzyme is >50° C.

Another important enzyme utilized by the lactate bypass is propionate CoA transferase (EC 2.8.3.1) (reaction 8 in FIG. 4B). This enzyme is known to catalyze a CoA transfer reaction between acetyl-CoA and propionate or between propionyl-CoA and acetate. However, the enzyme can also accept 3-hydroxypropionate and lactate as substrates. Therefore, the present inventors have integrated this enzyme in the proposed lactate bypass, to catalyze the CoA transfer between (R)-lactoyl-CoA and 3-hydroxypropionate (reaction #8). To estimate the specific activity of this reaction the present inventors have assumed it involves two steps: CoA transfer from (R)-lactoyl-CoA to acetate and a CoA transfer from acetyl-CoA to hydroxypropionate. Monitoring the rate of CoA transfer from acetyl-CoA, (R)-Lactate is a better substrate than acetate and almost as good as propionate. The rate in which the enzyme catalyzes the CoA transfer between acetyl-CoA and 3-hydroxypropionate is much slower: only 32% of the CoA units were transferred to 3-hydroxypropionate from acetyl-CoA (as compared to 80% for propionate, 65% for lactate and 60% for acrylate).

The hydratase enzyme crotonase (enoyl-CoA hydratase, EC 4.2.1.17) catalyzes the reversible hydration of crotonyl-CoA and of long chain (trans) 2,3-unsaturated fatty acids. The enzyme can also catalyze the reversible hydration of acrylyl-CoA to 3-hydroxypropionyl-CoA (reaction 9 in FIG. 4B). However, the specific activity of the enzyme for this reaction was not tested. Yet, the enzyme displays an extremely high specific activity for crotonyl-CoA hydration and hence even taking an extremely conservative estimation gives a significant activity.

The hydration of acrylyl-CoA to lactoyl-CoA is catalyzed by lactoyl-CoA dehydratase (EC 4.2.1.54) (reaction 10 in FIG. 4B). The enzyme, purified from the anaerobic prokaryote *Clostridium propionicum*, was extensively studied and was found to contain iron-sulfur centers and to be extremely oxygen sensitive: after a 1-min exposure to air, activity is inhibited by more than 90%. However, studies of lactoyl-CoA dehydratase from other organisms, such as *Pseudomonas* sp., *Peptostreptococcus elsdenii* and pigeon liver, showed efficient performance under full aerobic conditions.

III. The Simplest Carbon Fixation Cycles

The present search has found several ultra-short cycles that are able to fix carbon. Those cycles are shown in FIGS. 7A-G. All of these cycles utilize one ferredoxin-oxidoreductase enzyme. Interestingly, they all can be regarded as "metabolic shortcuts" of the reductive TCA cycle; the KGS-ICDH and the KGS-KGC pathways (FIGS. 7A-B) share all their metabolites with the rTCA cycle and use the enzyme isocitrate lyase as a "metabolic bridge" and thus fix two $CO_2$ molecules to form glyoxylate, which in turn can be converted into GA3P by the bacterial-like glycerate pathway. In addition, the PyrS-ME, PyrS-PyrC and the PyrS-PEPC pathways (FIGS. 7C-E) share their metabolites with the rTCA cycle, with malyl-CoA as the only foreign metabolite. The PyrS-PyrC-Oxalate and the PyrS-PEPC-Oxalate pathways (FIGS. 7F-G) are somewhat further metabolically distant from the rTCA cycle, but still share with it major metabolites.

The most attractive pathway of this group, PyS-PEPC-Glyoxylate, is a combination of the metabolic routes B and E, shown in FIG. 1. Those routes share three enzymes that can be discarded to create an efficient "metabolic shortcut" that produces glyoxylate, which is then assimilated by the bacterial-like glycerate pathway. This cycle was previously postulated, and named the reductive dicarboxylic acid cycle, but evidence for its natural existence is scarce. The pathway is thermodynamically feasible, does not contain a thermodynamic distributed bottleneck (see below) and is energy efficient. However, consistent with all the other pathways that use simple cycles, its pathway specific activity is significantly lower than that of the natural ferredoxin-oxidoreductase pathways, the rTCA cycle and the DC/4-HB cycles.

Out of the three pathways that use a 4-enzyme-cycle, two (KGS-ICDH and PyrS-ME) are not thermodynamically feasible because they contain a thermodynamic distributed bottleneck; the free energy change associated with their cycles is positive under the reasonable range of estimated physiological concentrations of their substrates and products (Table 1, FIG. 12). In addition, the "malic" enzyme (of the cycle PyrS-ME) strongly prefers decarboxylation under ambient $CO_2$ concentration. Using this enzyme for carboxylation is highly questionable.

Two of the pathways that use a 5-enzymes-cycle (KGS-KGC and PyrS-PyrC-Glyoxylate) are thermodynamically questionable. This is because the free energy change associated with their cycles may be positive under a broad range of estimated physiological concentrations of their product (FIG. 12, Table 1). Moreover, the KGS-KGC cycle utilizes the enzyme 2-ketoglutarate carboxylase that was found to operate only in one thermophilic bacterium, *Hydrogenobacter thermophilus*, with an optimum temperature of 70-80° C. This makes the cycle even less attractive. The PyrS-PyrC-Oxalate and the PyrS-PEPC-Oxalate cycles (FIGS. 7F-G) are thermodynamically feasible but their energy efficiency is quite low (ATP cost of 10 and 12, respectively). To conclude, none of the simplest cycles present a promising alternative to the natural pathways. Simplicity alone does not seem to be a good indicator of the usefulness of a pathway, in terms of rate (the natural, complex rTCA and 3-HP/4-HB cycles have significantly higher specific activities), of energetic balance and of the enzymes employed (all use ferredoxin-oxidoredcutase enzymes).

IV. Other Interesting Carbon Fixation Pathways

The AcC-ICDH Cycles

An interesting enzyme, 2-hydroxyglutarate synthase (EC 2.3.3.11), found to operate in *Escherichia coli*, has potential use in synthetic pathway design. Two efficient carbon fixation pathways can be suggested by using its catalytic condensation of propionyl-CoA and glyoxylate (FIGS. 9A-C). Both use the carboxylating enzymes acetyl-CoA carboxylase and isocitrate dehydrogenase, for which the $V_{max}$ for carboxylation, under ambient $CO_2$ concentration, are rather high (FIG. 13, Table 2, and Example 1).

The first pathway (FIG. 9A), the AcC-ICDH-Glycerate cycle, produces glyoxylate that can be assimilated using the bacterial-like glycerate pathway or by the "citramalate" glyoxylate assimilation pathway (FIG. 6). The former option was found to have a higher pathway specific activity and is analyzed in FIG. 13, Table 2.

The second pathway (FIG. 9B), the AcC-ICDH-Pyruvate cycle, generates acetyl-CoA. Acetyl-CoA can then be assimilated to pyruvate using the sub-pathway shown in Aiii. Pyruvate is converted to GASP by the gluconeogenesis.

In terms of pathway specific activity, both pathways are significantly faster than the rPP cycle (at 20% oxygenase reaction of RUBISCO) and the 3-HP pathway. The AcC-ICDH-Glycerate pathway is simpler and more ATP efficient.

The AcC-PrC Cycles

The naturally found 3-HP pathway creates the basic structure of a cycle that uses acetyl-CoA and propionyl-CoA carboxylases as sole carboxylating enzymes. It is actually composed of two sequential cycles, with glyoxylate as the product of the first one. As a "shortcut" alternative to the second cycle (the "citramalate cycle"), which condenses glyoxylate with propionyl-CoA to produce acetyl-CoA and pyruvate, glyoxylate can be condensed by the bacterial-like glycerate pathway to produce glycerate (FIG. 6, FIG. 9D). This option was previously considered and was not found to function in the organisms tested (Herter S, et al. (2001) *J Bacteriol* 183(14):4305-4316). One of the reasons for the dismissal of this alternative was that the bacterial-like glycerate pathway involves the release of a $CO_2$ molecule (FIG. 6), which seems to counteract the carbon fixation role of the pathway (Herter S, et al. (2001) *J Bacteriol* 183(14):4305-4316). However, the present rate analysis demonstrates that the AcC-PrC-Glycerate pathway is not only more ATP efficient and simpler, but also significantly faster than the naturally found AcC-PrC-Citramalate pathway, even when taking into account the $CO_2$ released (Table 1, FIG. 12). This indicates that contrary to intuitive thinking, the AcC-PrC-Glycerate pathway might serve as an excellent carbon fixation pathway.

FIGS. 9D-G illustrate another derivative of the 3-hydroxypropionate pathway, the AcC-PrC-Citrate pathway. The cycle produces acetyl-CoA (FIG. 9E) which can be assimilated into pyruvate using a metabolic derivative of the main cycle (FIG. 9F). Pyruvate is converted to GA3P by gluconeogenesis. As shown in, the pathway is as fast and as ATP efficient as the other AcC-PrC pathways.

A non-ferredoxin-oxidoreductase-containing pathway can be derived from the 3-HP/4-HB pathway, by converting the cycle's intermediate, succinyl-CoA, to malate and then to pyruvate (FIG. 9G). The pathway has a comparable rate to the 3-HP/CM pathway. However, the pathway utilizes two oxygen sensitive enzymes, 4-hydroxybutaryl-CoA dehydrates and succinate-semialdehyde dehydrogenase, which decrease its overall usability.

The Crotonyl-CoA Cycles

Three interesting cycles can be constructed around crotonyl-CoA (FIGS. 9H-J). Those cycles utilize different sets of carboxylating enzymes.

FIG. 9H displays an interesting pathway that uses a newly discovered unusual carboxylating enzyme, crotonyl-CoA carboxylase-reductase. However, the CCR-PEPC pathway is rather slow and is characterized by a specific activity comparable to that of the rPP cycle.

FIGS. 9I-J present carbon fixation pathways that utilize the enzyme methylcrotonyl-CoA carboxylase. Glyoxylate, produced by the cycles is assimilated by the bacterial-like glycerate pathway. The MCC-ICDH pathways are the slowest pathways analyzed. This is because the carboxylation of crotonyl-CoA is relatively inefficient (FIG. 13, Table 2). Moreover, the MCC-ICDH pathways utilize the oxygen sensitive enzyme 2-hydroxyglutaryl-CoA dehydratase, which further decreases the overall usability of the pathways. The MCC-ICDH-4HB cycle uses other oxygen sensitive enzymes that participate in the natural 3-HP/4-HB cycle.

The AcC-PrC-KGS-ICDH Cycle

FIG. 1, which displays the naturally occurring carbon fixation pathways, hides another uncommon combination of metabolic routes D and A that generate a metabolic hybrid of the 3-hydroxypropionate pathway and the rTCA cycle. However, the AcC-PrC-KGS-ICDH pathway is not an efficient one. Its pathway specific activity is only 0.67 mol/min/mg, which is much lower than that of the other ferredoxin-oxidoreductase pathways.

The Glutamate Cycles

Four interesting pathways can be constructed using a mutase enzyme that converts glutamate to methylaspartate (FIGS. 9K-M). The first two are shown in FIG. 9K. The two left "downward" metabolic routes correspond to the naturally occurring routes B and D of FIG. 1. The PyrS-PEPC-KGS-Glutamate pathway has a pathway specific activity that is comparable to that of the 3-HP/4-HB pathway, while the AcC-PrC-Glutamate pathway has a very low pathway specific activity.

The third pathway, the PrC-KS-Glutamate pathway, shown in FIG. 9L is unique because it is the only pathway that utilizes propionyl-CoA carboxylase without acetyl-CoA carboxylase. The PrC-KS-Glutamate pathway has a pathway specific activity that is comparable to that of the 3-hydroxypropionate/4-hydroxybutyrate cycle.

The PyrS-ICDH-Glutamate pathway, shown in FIG. 5M, was not further analyzed.

Importantly, all the glutamate cycles utilizes the enzyme methylaspartate mutase. This enzyme is dependent on vitamin B12 (cobalamin) for its operation. Eukaryotic photosynthetic organisms do not synthesize this co-factor. Higher plants make use of cobalamin-independent enzymes and algae, like animals, have a requirement for an external source of vitamin B12. Therefore, the utilization of the glutamate cycles should be restricted to cyanobacteria only.

The Threonine Cycles

FIG. 5I displays carbon fixation pathways which utilize threonine aldolase. Alternatively, threonine can be converted to 2-amino-3-oxobutanoate, which is then metabolized to acetyl-CoA and glycine. Using an amino-transferase enzyme, glycine is converted to glyoxylate. The starting metabolite, pyruvate, can be produced either by using the enzyme pyruvate synthase or by the alanine bypass (see FIG. 8). Importantly, the threonine pathways can be considered as a bypass of the cycle shown in FIG. 3, the rTCA "shortcut".

Algorithm for Finding Carbon Fixation Cycles

Stoichiometric properties of biochemical reactions are considered structural invariants, unlike the kinetic parameters which are affected by enzyme concentrations, activity and many other factors. There is a vast amount of reliable data for stoichiometric values of virtually all known enzymes, for example in the KEGG database (www(dot)keggsotjp/kegg/kegg2(dot)html) (Kanehisa M & Goto S (2000) KEGG: kyoto encyclopedia of genes and genomes. *Nucleic Acids Res* 28(1):27-30).

The present inventors developed an algorithm that is a variant of constraint based modeling (Papin J A, et al. (2004) Trends Biotechnol 22(8):400-405; Schuster S, Dandekar T, & Fell D A (1999) Trends Biotechnol 17(2):53-60; Schilling C H, Letscher D, & Palsson B O (2000) J Theor Biol 203(3):229-248). The goal of the present algorithm was to find carbon fixation cycles, i.e. a set of reactions that together satisfy the stoichiometric requirements of carbon fixation, which are transforming three inorganic carbon molecules to one GASP molecule. The use of ubiquitous compounds and co-factors (such as $H_2O$, ATP, NAD(P)) was intentionally not taken into consideration.

The first stage was to construct a universal stoichiometric matrix, using the standard representation [Heinrich R & Schuster S (1996) *The Regulation of Cellular Systems* (Springer)] which is described below. The data was solely taken from KEGG, and stored in the 5280 by 15848 matrix, denoted by S. Note that every reaction is considered to be reversible, and thus is represented by two columns; one for each direction.

In order to reduce the complexity of the algorithm and the amount of time needed, compounds were removed according to two criteria. First, all the known co-factors were discarded. These are listed in the table given below. Although co-factors play a big role in the energetic cost of a cycle and its thermodynamic feasibility, the present inventors wanted at this stage only to find cycles that are stoichiometrically balanced and leave the other factors for later analysis. The rows in S corresponding to these co-factors were thus removed. The second criterion was to discard all compounds which contain more than 10 carbon atoms or that have a non-specific chemical formula (like the compound "amino acid" with the formula $C_2H_4NO_2R$). The rows corresponding with these compounds were removed, and so were the columns of reactions that have such a compound as a substrate or product. The size restriction is not necessary and results usually do not change even if the threshold for the size of compounds is different. Also, small compounds which are attached to carrier molecules (like CoA or THF) were not excluded, e.g. the "acetyl" in acetyl-CoA has only 2 carbon atoms, and thus was not removed. In addition, if a reaction was not chemically balanced it was discarded as well.

At this stage, S contained ~1400 rows and ~3000 columns. The present inventors added three special columns, which were not stoichiometrically balanced: input of $CO_2$, input of $HCO_3^-$ and output of GA3P. The input reactions had the value of (+1) at the row corresponding to $CO_2$ or $HCO_3^-$ and zeros in all other places. The last column in S—the output reaction—had a (−1) at the row corresponding to GA3P and zeros everywhere else.

The present inventors then searched for solutions to the following linear problem:

$$Sv=0$$

$$v_i \geq 0$$

$$v_{output}=1$$

$$\text{minimize } \Sigma v_i$$

where v is the flux vector, so that $v_i$ is the flux going through each reaction, and $v_{output}$ is the flux of GA3P output (the value corresponding to the last column in S). Note that any solution that fulfills the first 3 requirements is a carbon fixation cycle (as defined by us). Minimizing $\Sigma v_i$ is equivalent to minimizing the total flux.

A script for parsing the data from KEGG, analyzing the compounds, discarding the co-factors and large molecules, checking chemical balance and producing the final S matrix was written in-house using the Python programming language. To solve the linear problem, the GLPK (GNU Linear Programming Kit, www(dot)gnu(dot)org/software/glpk/)

was used. The parameters of the problem were fed to the GLPK solver with the help of a wrapper module called ctypes-glpk (www(dot)code(dot)google(dot)com/p/ctypes-glpk/).

The GLPK solver normally returns a sparse minimal solution, which means that v has only a few non-zero values. In other words, the solution is comprised of a small set of reactions which have a positive flux (usually integer values). Sparse solutions are useful because they are simple and implementing them in-vitro or in-vivo is probably easier.

The carboxylation step is the most important step of a carbon fixation cycle (see Example 1). This step is commonly sensitive to the levels of $CO_2$ and $O_2$ which are diffusible gaseous compounds whose concentrations are hard to regulate. Therefore, the present inventors were interested in finding cycles that employ a specific set of carboxylating enzymes, the ones which are kinetically superior. In order to achieve this, the present inventors simply "shut out" all the other carboxylating enzymes, by forcing the flux vector to have a value of 0 for the reactions corresponding to these enzymes. Since fixing inorganic carbon is the only way to get carbon atoms into the cycle, and since present inventors constrained it to export GA3P, the solution to the linear problem will have to use at least one of the carboxylators in the chosen set.

If that set contains a single enzyme, the flux through it will have to be exactly 3 (due to the conservation rules of carbon atoms).

TABLE 3

List of co-factors which were removed from the stoichiometric matrix:

| | | | |
|---|---|---|---|
| Arsenate | dIMP | FADH2 | H2O |
| Arsenite | Deamino-NAD+ | FAD | Oxygen |
| Manganese | HO- | Ferricytochrome | Orthophosphate |
| Cobalt | HSO3- | Ferrocytochrome | Pyrophosphate |
| Selenate | Hydrochloric | Ferricytochrome | NH3 |
| Nickel | Nitrite | Ferrocytochrome | CoA |
| Sulfur | Sulfate | Reduced | Tetrahydro-folate |
| Hydrazine | Sulfite | Oxidized | H+ |
| Trimetaphosphate | Sulfur | Reduced | ATP |
| Phosphoramidate | Thiosulfate | Oxidized | ADP |
| Nitrogen | Hydrogen | Acceptor | AMP |
| Selenophosphate | Nitric | Donor | GTP |
| Nitrate | Chloride | H2O2 | GDP |
| Hydrofluoric | Fluoride | dATP | GMP |
| Tetrathionate | Hydroxylamine | dADP | CTP |
| HI | Selenite | dAMP | CDP |
| Nitrous | Hydrogen | dGTP | CMP |
| Hg | Iodine | dGDP | UTP |
| Bromide | Fe3+ | dGMP | UDP |
| Hydrobromic | Fe2+ | dUTP | UMP |
| Chlorate | Iron | dUDP | ITP |
| Chlorite | Magnesium | dUMP | IDP |
| Diimine | Mercury(2+) | dTTP | IMP |
| Halide | O2.- | dTDP | NADPH |
| Thioredoxin | Selenium | dTMP | NADP+ |
| Thioredoxin | Selenide | dITP | NADH |
| | Iodide | dIDP | NAD+ |

Pathway Analysis Methods—Thermodynamics

I. Thermodynamics of Carbon Fixation Cycles

1. The Basic Net Reaction and its Energetics

The reductive pentose phosphate (rPP) pathway can be simplified, or "compressed", to the following reaction, assuming that glyceraldehyde-3-phosphate (GA3P) is its product:

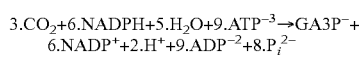

To better understand the overall reaction, we can be divided it into three reactions:

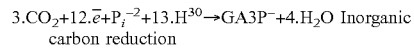
Inorganic carbon reduction

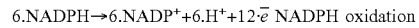
NADPH oxidation

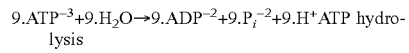
ATP hydrolysis

We are interested in the thermodynamics of carbon fixation under a specified pH (fixed $H^+$ concentration); in other words, we look for the standard transformed Gibbs energy change ($\Delta G'_r$). Under these conditions the above equation should be changed as follows: (A) Hydrogen atoms are not conserved in the reaction and therefore should not be included. (B) Each reactant that can exist in various protonated species is represented by a single compound. For example, 'ATP' correspond the following protonated species: $ATP^{4-}$, $HATP^{3-}$, $H_2ATP^{2-}$. (C) The reactants do not show ionic charges or number of hydrogen atoms they contain because under a constant pH each reactant exists in a superposition of those states.

Therefore, under specified and fixed pH, the above reaction should be written as:

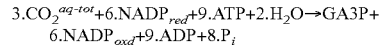

The reactant $CO_2^{aq\text{-}tot}$ refers to a superposition of $CO_3^{2-}$ (aq), $HCO_3^-$(aq), $CO_2$(aq) and $H_2CO_3$(aq), where the ratio between those states is determined by the system's pH (as well as temperature and ionic strength).

For convenience in later analysis, the above reaction can be separated into two components: an ATP free reaction and an ATP hydrolysis reaction. We shall refer to the ATP-free reaction as the basic carbon fixation net reaction. The basic carbon fixation net reaction and the ATP hydrolysis reaction are given by:

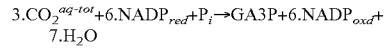

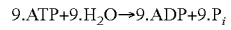

Moreover, assuming that GA3P is the common product of all the carbon fixation pathways analyzed, all can be simplified to the basic net reaction coupled to ATP hydrolysis reactions:

$X.ATP + X.H_2O \rightarrow X.ADP + X \cdot P_i$ where X depends on the particular pathway.

In order to calculate the standard transformed energies ($\Delta G_r'^o$) of the basic net reaction and the ATP hydrolysis reaction one need to obtain the standard transformed energies of formation ($\Delta G_f'^o$) of the reactants participating in those reactions. Those, in turn, can be calculated, at specified pH and ionic strength, from the standard energies of formation) ($\Delta G_f^0$), as given by eq. 1:

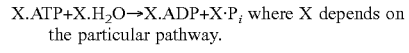

where I, $N_H$ and z refer to ionic strength, number of hydrogen atoms in the compound and charge of the compound, respectively. Note that the second term actually equals $N_H(RT \ln(10) \cdot pH + \Delta G_f^0(H^+))$, but $\Delta G_f^0(H^+)$ is taken to be 0 in standard calculation and measurements. $\Delta G_f'^o$ is a monotonically increasing function with pH and a monotonically decreasing function with I. The pH affects $\Delta G_f'^o$ more significantly than the ionic strength; the second term in the equation is considerably higher than the third one under common physiological conditions (5<pH<9, 0<I<0.4, 0<$N_H$<30, |z|≤4). When a certain compound can exists in several states, each having a different number of hydrogen atoms (such as $CH_3COOH$ and $CH_3COO^-$), the standard transformed energy of formation of this compound is given by eq. 2:

$$\Delta G_f'^0 = -RT\ln\left(\sum_{j=1}^{m} \exp(-\Delta G_f'^0(j)/RT)\right)$$

$$\Delta G_f'^0 =$$

$$\Delta G_f^0(I=0) - RT\ln\left(\sum_{j=1}^{m} \exp(N_H RT\ln(10)\cdot pH - (2.91482(z^2 - N_H)I^{0.5})/(1 + 1.6I^{0.5}))/RT\right)$$

where $\Delta G_f^0(j)$, j=1, 2 ... m, are the standard transformed energies of formation of the different states the compound can exist in.

Using this method we have calculated $\Delta G_r'^0$ of the basic net reaction and the ATP hydrolysis reaction in pH ranging from κ to 9 and ionic strength ranging from 0 to 0.4M. For example:

TABLE 4

| ATP hydrolysis $\Delta_r G'^{\circ}$ (KJ/mol), 298.15K, 100 kPa | | | Basic net reaction $\Delta_r G'^{\circ}$ (KJ/mol), 298.15K, 100 kPa | | | |
|---|---|---|---|---|---|---|
| pH = 8 | pH = 7 | pH = 6 | pH = 8 | pH = 7 | pH = 6 | |
| −42 | −37 | −34 | 196 | 146 | 104 | I = 0.1M |
| −41 | −36 | −33 | 207 | 157 | 113 | I = 0.25M |

$\Delta G_r'^0$ of the basic net reaction is a monotonically increasing function with pH and ionic strength. Why is it? Assuming that all reactants and products exist in only one state (eq. 1), the behavior of $\Delta G_r'^0$ as a function of pH depends on the difference between the sum of $N_H$ of the reactants and the sum of $N_H$ of the products. In the same manner, the behavior of $\Delta G_r'^0$ as a function of ionic strength depends on the difference between the sum of $(z^2-N_H)$ of the reactants and the sum of $(z^2-N_H)$ of the products. If some of the reactants and products can exists in several states (eq. 2), no closed solution can be provided as above. However, in such cases an estimation can be proposed. Usually one of the possible states of each reactants/products is the dominant one (having lower $\Delta G_f'^0(j)$); we can therefore approximate $\Delta G_f'^0$ of this compound to that lower $\Delta G_f'^0(j)$, as given in eq. 1.

In the case of the basic net reaction $\Sigma N_H$ of the reactants is lower than that of the products, while $\Sigma(z^2-N_H)$ of the reactants is higher than that of the products. Therefore, $\Delta G_r'^0$ of the basic net reaction is a monotonically increasing function with pH and ionic strength. For the ATP hydrolysis reaction these trends are reversed; $\Delta G_r'^0$ is a monotonically decreasing function with pH because $\Sigma N_H$ of the reactants is higher than that of the products. Also, $\Delta G_r'^0$ is a monotonically decreasing function with ionic strength because $\Sigma(z^2-N_H)$ of the reactants is lower than that of the products.

In order to calculate the transformed energies $\Delta G'_r$ (non-standard concentrations) we need estimations of the reactant concentrations. Following measurements from Spinach chloroplast (42, 43) we have used [GA3P]=0.025 mM, [$NADP_{red}$]=0.29 mM, [$NADP_{oxd}$]=0.59 mM, [ATP]=1.9 mM, [ADP]=0.76 mM and [$P_i$]=20 mM. The concentration of inorganic carbon, [$CO_2^{aq-tot}$], was calculated using the apparent Henry's law constant, derived from $\Delta G_r'^0$ of the reaction $CO_2^{aq-tot} \leftrightarrow CO_2^g + H_2O$ (41). $CO_2^g$ concentration was assumed to be 387 ppm. FIG. 10A displays the expected concentration of total dissolved inorganic carbon as a function of pH and ionic strength. pH has an extremely strong effect on this concentration. The [$CO_2^{aq-tot}$] values obtained by this analysis agree with known experimental data, which measured bicarbonate concentration of 0.26 mM and 2 mM at pH of 7.4 and 8.2, respectively.

Using these values we have calculated $\Delta G_r'^0$ at the same pH and ionic strength ranges. For example:

TABLE 5

| ATP hydrolysis $\Delta_r G'$ (KJ/mol), 298.15K, 100 kPa | | | Basic net reaction $\Delta_r G'$ (KJ/mol), 298.15K, 100 kPa | | | |
|---|---|---|---|---|---|---|
| pH = 8 | pH = 7 | pH = 6 | pH = 8 | pH = 7 | pH = 6 | |
| −46 | −41 | −39 | 243 | 209 | 178 | I = 0.1M |
| −46 | −41 | −38 | 252 | 219 | 187 | I = 0.25M |

At a given pH and ionic strength one can therefore determine the minimum number of ATP hydrolysis reactions needed to be coupled to carbon fixation in order to ensure its feasibility. FIG. 2A presents this minimal ATP requirement, as a function of pH and ionic strength. Clearly, carbon fixation pathways that can be simplified to the basic net reaction need to be coupled to the hydrolysis of at least 5-6 ATP molecules in order to become thermodynamically feasible, under ambient $CO_2^g$ concentration and characteristic pH and ionic strength. The extra ATP molecules hydrolyzed by the rPP cycle are not essential for the thermodynamic feasibility of the cycle but they create an extra energetic driving force that facilitates carbon fixation while introducing several irreversible reactions (bisphosphatases).

2. Modifications of the Basic Net Reaction

Many of the carbon fixation pathways can be simplified to a modified form of the basic net reaction, where different redox carriers, other than NAD(P)$_{red}$, are utilized by the pathways. Because diverse electron donors are characterized by different reduction potential, those modifications can significantly change the overall thermodynamics of the pathways.

2.1 Ferredoxin

Ferredoxin (Fd) is a carrier of only one electron and therefore two ferredoxins are needed in order to replace one $NADP_{red}$ molecule. 2.$Fd_{red}$ can replace $NADP_{red}$ corresponding to the use of the enzymes pyruvate and 2-ketoglutarate synthases. $\Delta G_r'^0$ for the modified net reaction can be deduced by treating it as two reactions. The first reaction includes the reduction of $NADP_{oxd}$ by 2.$Fd_{red}$ and the second corresponds to the basic carbon fixation net reaction. We exemplify this by a modified net reaction in which one $NADP_{red}$ was replaced with 2.$Fd_{red}$:

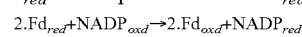

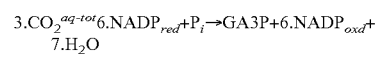

Total:

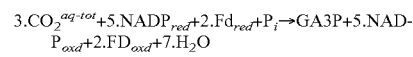

The $\Delta G_r^{\prime o}$ of the ferredoxin-free reaction was discussed above, and the $\Delta G_r^{\prime o}$ of the first reaction, which reduced $NADP_{oxd}$ by $2.Fd_{red}$, can be calculated as explained above. For example:

TABLE 6

| 2·$Fd_{red}$ + $NADP_{oxd}$ → 2·$Fd_{oxd}$ + $NADP_{red}$ $\Delta_r G'^o$ (KJ/mol), 298.15 K, 100 kPa | | | |
|---|---|---|---|
| pH = 8 | pH = 7 | pH = 6 | |
| −9 | −15 | −21 | I = 0.1M |
| −11 | −17 | −22 | I = 0.25M |

In order to calculate $\Delta G_r'$ of the ferredoxin pathways, we need an estimation of the relative concentration of $Fd^{red}$ and $Fe^{oxd}$. Unfortunately, such data is not available. Therefore, we have assumed $[Fe^{red}] \sim [Fd^{oxd}]$, which gave, for example:

TABLE 7

| 2·$Fd_{red}$ + $NADP_{oxd}$ → 2·$Fd_{oxd}$ + $NADP_{red}$ $\Delta_r G'$ (KJ/mol), 298.15 K, 100 kPa | | | |
|---|---|---|---|
| pH = 8 | pH = 7 | pH = 6 | |
| −11 | −17 | −23 | I = 0.1M |
| −13 | −18 | −24 | I = 0.25M |

This result indicates that the energetic gain of using Fd instead of NADP, as electron donor, is roughly equivalent to the energy released in the hydrolysis of one half of an ATP molecule.

2.2 Ubiquinone and Succinate Dehydrogenase

The enzyme succinate dehydrogenase uses ubiquinone (UQ) as an electron acceptor, instead of NADP. Therefore, the net reactions of pathways that utilize this enzyme include UQ. Those reactions can also be divided into two coupled reactions. One includes the reduction of $UQ_{oxd}$ by $NADP_{red}$ and the other corresponds to the basic carbon fixation net reaction. For example:

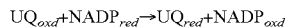

$UQ_{oxd} + NADP_{red} \rightarrow UQ_{red} + NADP_{oxd}$

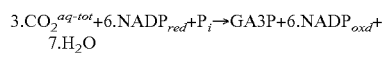

$3.CO_2^{aq-tot} + 6.NADP_{red} + P_i \rightarrow GA3P + 6.NADP_{oxd} + 7.H_2O$

Total:

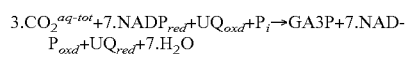

$3.CO_2^{aq-tot} + 7.NADP_{red} + UQ_{oxd} + P_i \rightarrow GA3P + 7.NADP_{oxd} + UQ_{red} + 7.H_2O$ The $\Delta G_r^{\prime o}$ of the first reaction, which reduced $UQ_{oxd}$ by $NADP_{red}$, can be again calculated as above. For example:

TABLE 8

| $UQ_{oxd}$ + $NADP_{red}$ → $UQ_{red}$ + $NADP_{oxd}$ $\Delta_r G'^o$ (KJ/mol), 298.15 K, 100 kPa | | | |
|---|---|---|---|
| pH = 8 | pH = 7 | pH = 6 | |
| −65 | −71 | −77 | I = 0.1M |
| −64 | −69 | −75 | I = 0.25M |

Due to a lack of available data we again assume $[UQ_{oxd}] \sim [UQ_{oxd}]$. For example:

TABLE 9

| $UQ_{oxd}$ + $NADP_{red}$ → $UQ_{red}$ + $NADP_{oxd}$ $\Delta_r G'$ (KJ/mol), 298.15 K, 100 kPa | | | |
|---|---|---|---|
| pH = 8 | pH = 7 | pH = 6 | |
| −64 | −69 | −75 | I = 0.1M |
| −62 | −68 | −73 | I = 0.25M |

2.3 Menaquinone and Fumarate Reductase

The enzyme fumarate reductase can use several redox curriers as electron donors. Those include menaquinone (MQ) FAD/FMN or even $NAD_{red}$. Menaquinone is the common electron donor for membrane-bound fumarate reductase. Applying the same reaction division procedure as above we get:

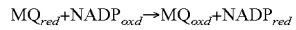

$MQ_{red} + NADP_{oxd} \rightarrow MQ_{oxd} + NADP_{red}$

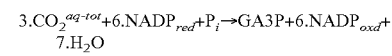

$3.CO_2^{aq-tot} + 6.NADP_{red} + P_i \rightarrow GA3P + 6.NADP_{oxd} + 7.H_2O$

Total:

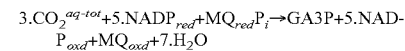

$3.CO_2^{aq-tot} + 5.NADP_{red} + MQ_{red} P_i \rightarrow GA3P + 5.NADP_{oxd} + MQ_{oxd} + 7.H_2O$ We weren't able to find information on $\Delta G_f^{\prime o}$ ($MQ_{red/oxd}$) as function of pH and ionic strength. Therefore, in order to calculate the energy change $\Delta_r G^{\prime o}$ of the first reaction, we have used the reduction potential of menaquinone, −75 mV (47, 48):

$\Delta E(MQ_{red} + NADP_{oxd} \rightarrow UQ_{oxd} + NADP_{red}) = -245$ mV

Hence we obtain: $\Delta G_r^{\prime o}$ ($MQ_{red} + NADP_{oxd} \rightarrow UQ_{oxd} + NADP_{red}$) = −2·96.5·−0.245 = +47 KJ/mol This result indicates that the energetic cost of using MQ instead of NADP, as electron donor, is roughly equivalent to the energy released in the hydrolysis of one ATP molecule. Eukaryotic organisms usually use rhodoquinone instead of menaquinone. The reduction potential of rhodoquinone is −63 mV, very close to that of menaquinone.

Intuitively, one might think that because MQ is ultimately reduced using $NADP_{red}$ we can neglect MQ altogether and refer to $NADP_{red}$ as the electron donor de-facto. However, in most organisms that employ fumarate reductase MQ is being reduced by the oxidation of $NADP_{red}$ by the respiratory complex I. The electron flow through part of complex I is used to generate proton gradient and hence ATP. This energetic coupling disrupts the thermodynamic calculation by increasing the overall $\Delta G_f^{\prime o}$ and making the energetics of MQ reduction by $NADP_{red}$ very difficult to calculate. Therefore, we regard $MQ_{red}$, and not $NADP_{red}$, as the electron donor.

The energetic cost of using menaquinone can be avoided by employing fumarate reductase enzymes that utilize other electron donors. Fumarate reductase from *Saccharomyces cerevisiae* is a soluble enzyme that accepts electrons from a non-bound, reduced FAD. The energetic cost of using FAD can be calculated as above. For example:

TABLE 10

| $FAD_{red}$ + $NADP_{oxd}$ → $FAD_{oxd}$ + $NADP_{red}$ $\Delta_r G'^o$ (KJ/mol), 298.15 K, 100 kPa | | | |
|---|---|---|---|
| pH = 8 | pH = 7 | pH = 6 | |
| 14 | 20 | 26 | I = 0.1M |
| 13 | 18 | 24 | I = 0.25M |

Due to a lack of available data we again assume [$FAD_{oxd}$] ~[$FAD_{oxd}$], arriving at:

TABLE 11

$FAD_{red}$ + $NADP_{oxd}$ → $FAD_{oxd}$ + $NADP_{red}$
$\Delta_r G'$ (KJ/mol), 298.15 K, 100 kPa

| pH = 8 | pH = 7 | pH = 6 | |
|---|---|---|---|
| 13 | 18 | 24 | I = 0.1M |
| 11 | 17 | 22 | I = 0.25M |

Several organisms are known to use $NAD_{red}$ as a direct electron donor for fumarate reductase, avoiding any additional energetic cost. Importantly, this enzyme variant is soluble and remains active under aerobic conditions. We would expect organisms that reduce fumarate as part of the reductive TCA to employ this efficient enzyme. Indeed, a recent paper has demonstrated that this is the case for the thermophilic bacterium, *Hydrogenobacter thermophilus*, which fixes carbon through the reductive TCA cycle.

3. Energetic of Carbon Fixation Pathways

Employing the modifications analyzed above we were able to calculate $\Delta G'_r$ for the carbon fixation pathways, both natural and synthetic. Almost all pathways are thermodynamically feasible at ambient $CO_2^g$ concentration ($\Delta_r G^\circ \ll 0$), as shown in Table 1, FIG. 12. However, the natural rTCA cycle and rAcCoA pathway (shown in FIG. 5B) are not feasible ($\Delta_r G^\circ > 0$) at a broad range of pH and ionic strengths and under ambient $CO_2^g$ concentration as shown in FIG. 10B.

Notably, increased $CO_2^g$ concentration can make those pathways feasible; the rTCA-MQ cycle becomes feasible at all pH and ionic strength values at X100 the $CO_2^g$ ambient concentration, while the rAcCoA pathway is feasible at pH<8 at the same $CO_2^g$ concentration (FIG. 10B). Such elevated $CO_2^g$ concentration might be expected in certain environments, in C4 and CAM plants and in algae that use $CO_2$ concentrating mechanisms.

Importantly, three of the enzymes of the rAcCoA pathway can use molecular hydrogen as direct electron donors, instead of NAD(P)H. We did not calculate the energetics of such carbon fixation process due to the wide range of $H_2$ concentrations that can be present in the medium, spanning many magnitudes of orders.

It should be noted that the rTCA cycle and the rAcCOA pathway operate in strictly anaerobic organisms. Anaerobes are energy restricted as compared to aerobes because they utilize only chemical reactions with low energetic yield (e.g. sulfur, Fe, Mn and nitrate respirations,). This limits the availability of energy that they can invest in carbon fixation. In order to achieve thermodynamic feasibility and sustain growth, the organisms that utilize either of those cycles must occupy high $CO_2$ habitats or operate a carbon concentrating mechanism. Moreover, the reductive acetyl-CoA pathway, is known to be coupled to other exogenic cellular processes in order to achieve energetic feasibility.

4. Carbon Fixation Cycles can be "Distributed Thermodynamic Bottlenecks'"

The analysis of energetics described above refers to the whole carbon fixation pathway as a single unit. This can predict the infeasibility of a pathway. It can also predict its feasibility in cases where we do not restrict the concentrations of the different metabolites. In practice however, those concentrations are constrained by both upper and lower limits. As a result, the overall energetics of the pathway is not enough to predict feasibility. A sub-pathway within the pathway can be infeasible under given set of concentration restrictions even if the $\Delta G_r$ of the entire pathway is less than 0. The sub-pathway is then referred to as a "distributed thermodynamic bottleneck".

We would like to check whether the cycle of each pathway creates a distributed thermodynamic bottleneck. There are four types of cycles, classified by their products; their basic net reactions are given below (not including ATP hydrolysis). The energy changes $\Delta G_r^{\prime\circ}$ of these reactions were calculated as explained above. For example:

TABLE 12

Standard Transformed Gibbs Energy
Changed for Carbon Fixation Cycles $\Delta_r G'^\circ$ (KJ/mol), 298.15 K, 100 kPa

| pH = 8 | pH = 7 | pH = 6 | Reaction/Modification |
|---|---|---|---|
| \multicolumn{4}{c}{Glyoxylate-forming cycles:} | | | |
| \multicolumn{4}{c}{$2 \cdot CO_2^{aq-tot} + 2 \cdot NADP_{red}$ → Glyoxylate($C_2O_3$) + $2 \cdot NADP_{oxd} + 3 \cdot H_2O$} | | | |
| 90 | 73 | 60 | I = 0.1M |
| 93 | 76 | 63 | I = 0.25M |
| \multicolumn{4}{c}{Acetyl-CoA-forming cycles:} | | | |
| \multicolumn{4}{c}{$2 \cdot CO_2^{aq-tot} + 4 \cdot NADP_{red} + CoA$ → Acetyl-CoA($C_2O$-CoA) + $4 \cdot NADP_{oxd} + 5 \cdot H_2O$} | | | |
| 38 | −2 | −38 | I = 0.1M |
| 45 | 5 | −31 | I = 0.25M |
| \multicolumn{4}{c}{Pyruvate-forming cycles:} | | | |
| \multicolumn{4}{c}{$3 \cdot CO_2^{aq-tot} + 5 \cdot NADP_{red}$ → Pyruvate($C_3O_3$) + $5 \cdot NADP_{oxd} + 6 \cdot H_2O$} | | | |
| 82 | 43 | 8 | I = 0.1M |
| 90 | 51 | 16 | I = 0.25M |
| \multicolumn{4}{c}{Oxalate-forming cycles:} | | | |
| \multicolumn{4}{c}{$2 \cdot CO_2 + NADP_{red}$ → Oxalate($C_2O_4$) + $NADP_{oxd} + 2 \cdot H_2O$} | | | |
| 49 | 44 | 42 | I = 0.1M |
| 50 | 45 | 42 | I = 0.25M |

The concentrations of the cycles' products, as well as that of CoA, were estimated to lie between 1 μM and 10 mM. For CoA, acetyl-CoA and pyruvate, those estimations are supported by experimental data. For glyoxylate and oxalate, those estimations correspond to the affinities of those metabolites to their utilizing enzymes; the affinity of glyoxylate towards glyoxylate carboligase is 250 μM, while the affinity of oxalate towards the enzyme oxalate-coA ligase is 2 mM. The maximal/minimal ratio between CoA and acetyl-CoA was taken as $10^{\pm 2}$.

We have calculated $\Delta G'_r$ for the various cycles, employed by the different pathways, under this broad range of product concentrations. The cycles of most pathways are feasible at all pH and ionic strength values and under all possible product concentration, as shown in Table 1. Notably, the KGS-ICDH and PyrS-ME cycles are not feasible at all pH, ionic strength and product concentration values. Other three ferredoxin-oxidoreductase pathways, KGS-KGC, PyrS-PyrC-Glyoxylate and PrC-KGS-Glutamate, are all non-feasible at some pH and ionic strength values, which are dependent on the estimated glyoxylate concentration (FIG. 10C, upper row). The non-ferredoxin-oxidoreductase-containing pathway MCC-ICDH-Citrate also displays a similar behavior (FIG. 10C, bottom row). However, replacing the CoA-transferase enzyme, which converts 2-hydroxyglutaryl-CoA to 2-hydroxyglutarate, by a yet unknown thioester hydrolyze enzyme, will effectively reduce the ΔG of this cycle well below 0. While at some pH and ionic strength values the acetyl-CoA producing cycle of the rTCA cycle become infeasible, this constrain is less strict than that imposed on this pathway as a whole (GASP-forming).

D. Pathway Analysis Methods—Kinetics

I. Rate Analysis of Metabolic Pathways

1. The Pathway Specific Activity is the Upper Limit of the Specific Flux of a Pathway The specific flux of a pathway is the overall flux sustained by the pathway, J, divided by the total concentration of the enzymes utilized by the pathway, $\Sigma E_i = E_t$. In the general case of non-linear pathways, the flux through individual enzymes is not necessarily the same. In such case, we assign a stoichiometric coefficient, $w_i$, to each reaction i, which corresponds to the number of catalytic cycles the reaction takes to produce one molecule of the pathway's product (for example, given the simple pathway $E_1:X \rightarrow Y$, $E_2:Y+Y \rightarrow Z$, $E_3:Z \rightarrow Product$, we assign $w_1=2$ and $w_2=w_3=1$.). The enzyme cost ($1/V_i$, see methods) for each reaction is thus multiplied by its stoichiometric coefficient. To maintain an overall flux of 1 μmol/min the enzyme cost of the whole pathway is therefore given by $$\Sigma \frac{w_i}{V_i}.$$

As a result, in the general case, the pathway specific activity is given by:

$$PSA_A = 1/\sum_{i=1}^{m} \frac{w_i}{V_i}$$

where m, $V_i$ and $w_i$ are the number of the enzymes the pathway utilizes, the specific activities of those enzymes and their stoichiometric coefficients in the pathway, respectively. The specific flux of a pathway and the pathway specific activity are both given in units of mol/min/mg.

The specific flux of a pathway is approximated by the pathway specific activity if the following three assumptions hold:

(I) The backward reactions are negligible as compared to the forward one.
(II) All enzymes work in their zero-order regime, namely, they are substrate-saturated.
(III) The relative concentrations of the enzymes are optimal, which means that there is no surplus of any enzyme.

Intuitively, if we assume a non-negligible backward reaction of a certain enzyme its de-facto activity in the forward direction is decreased. The same holds for an enzyme that is not substrate-saturated; its activity is expected to be lower. Lastly, a non-optimal concentration of the enzymes also decreases the specific flux of a pathway. Therefore, a deviation from each of those assumptions results in a specific flux that is lower than the calculated pathway specific activity. In other words, the pathway specific activity is an upper limit estimation for the specific flux of a pathway.

The strength of the pathway specific activity as an approximation of the specific flux lies in that it does not require complete information of the kinetic parameters of the enzymes (the Michaelis constants) nor it necessitates an estimation of the intermediate metabolite concentrations.

Below we show the derivation of the specific flux of a simple, non-branching pathway, using different assumption sets. We demonstrate that indeed the pathway specific activity is higher than the specific fluxes calculated under different assumptions.

1.1 Determining the Specific Activities of Enzymes

Information on enzyme kinetics is dispersed and non standardized. As an estimate to determine the specific activities of the enzymes composing the different pathways we embarked on a comprehensive literature survey of >1500 papers. For each enzyme all available and relevant values (ranging 1-40 values per enzyme) were obtained. We have discarded the bottom 50% values, which represent less adapted versions and the top 10% values, which might correspond to experimental errors and unnatural conditions. We took the average of the remaining values as a representative specific activity of each enzyme.

The specific activities of the carboxylating enzymes were calculated as follows: we obtained, from each paper a specific activity value (under saturating $CO_2/HCO_3^-$) and carbon species ($CO_2$ or $HCO_3^-$) affinity. We have calculated the specific activity under ambient $CO_2/HCO_3^-$ concentrations by applying Michaelis-Menten kinetics with no cooperativity: $SA_{ambient}=SA_{saturating}[C]/([C]+K_m^C)$, where [C] is the ambient concentration of the carbon species and $K_m^C$ is the affinity of the enzyme towards that carbon species. [C] was taken to be 10 μM for $CO_2$ and was taken as 200 μM for $HCO_3^-$, corresponding to a pH of 7.2-7.4. The same data filtering as for specific activities of the non-carboxylating enzymes was applied and the average was set as a representative specific activity. Conservatively, for RUBISCO we chose a higher specific activity than the average value, 1.3 μmole/min/mg instead of 1.13, which correspond to the most recent studies and also to the well-accepted Kcat values of 3-4 sec$^{-1}$.

The enzyme list, including representative specific activities and ATP and NAD(P)H requirements is provided below in section G. Overall, 109 reactions were analyzed and over 1500 papers were scanned.

2. A Simple Pathway: General Definitions $$S_0 \underset{v_1}{\Leftrightarrow} S_1 \underset{v_2}{\Leftrightarrow} S_2 \underset{v_3}{\Leftrightarrow} \ldots \underset{v_{n-1}}{\Leftrightarrow} S_{n-1} \underset{v_n}{\Leftrightarrow} S_n \quad (1)$$

$$\frac{dS_i}{dt} = v_i - v_{i+1}, i = 1, \ldots, n \quad (2)$$

The concentration of the pathway substrate is assumed to be fixed, $S0=S$. The concentration of the product is assumed to be zero (a strong metabolic sink), $Sn=0$.

In all further analysis we assume that the system is in a steady state. In this case $J=v_i$ for any i.

The Haldane reversible three-step model (62) states:

$$v_i = E_i \frac{V_i^+ \frac{S_{i-1}}{K_i^+} - V_i^- \frac{S_i}{K_i^-}}{1 + \frac{S_{i-1}}{K_i^+} + \frac{S_i}{K_i^-}} \quad (3)$$

where $v_i^+$ and $v_i^-$ are the maximal specific forward and backward rates (μmol/min/mg), respectively, and $E_i$ is the amount of enzyme I (mg). $K_i^+$ and $K_i^-$ are the Michaelis constants for the substrate and the product (mM) and $S_{i-1}$ and $S_i$ are the concentrations of the substrate and the product (mM), respectively. Throughout the analysis we will assume a total volume of 1 litter, which imposes the same flux in units of mol/min/mg or in units of μM/min/mg.

We would like to maximize $J/E_T$.

3. Saturating Substrate (Zero-Order) Estimation

As mentioned above, two assumptions lie behind the pathway specific activity analysis:

(I) The backward reaction is negligible as compared to the forward one, $V_i^+/K_i^+ \gg V_i^-/K_i^-$.

(II) All enzymes work in their zero-order regime, $K_i^+ \ll S_{i+1}$.

Those assumptions yield a steady-state flux of $$J = v_i = E_i V_i^+ \quad (4)$$

which in turn imposes an optimal enzyme distribution of $$\frac{E_1}{E_T} = (1/V_i^+) \Big/ \sum_{j=1}^{i} (1/V_j^+) \quad (5)$$

In such an optimal enzyme distribution no enzyme is in surplus and the relative amount of each enzyme is a function of the rates of all the other enzymes, but of no other parameter.

Substituting $E_i$ in J yields $$\frac{J}{E_T} = 1 \Big/ \sum_{j=1}^{i} (1/V_j^+) \quad (6)$$

Considering n identical reactions, with equipotent rates $V^+ = V$, we finally get:

$$\frac{J}{E_T} = \frac{1}{n} V \quad (7)$$

4. Linear-Regime Estimation

Let us assume $S_{i-1} \ll K_i^+$, $S_i \ll K_i^-$.

The rate of each reaction can therefore be expressed using linear rate constants (63, 64):

$$v_i = k_i S_{i-1} - k_{-i} S_i = k_i \left( S_{i-1} - \frac{S_i}{q_i} \right)$$

where $$k_i = \frac{V_i^+}{K_i^+} E_i, \quad k_{-i} = \frac{V_i^-}{K_i^-} E_i, \quad q_i = \frac{k_i}{k_{-i}}$$

In such a case the steady-state flux and the intermediates' concentrations are given by $$J = \left( S \prod_{j=1}^{n} q_j \right) \Big/ \left( \sum_{j=1}^{n} \frac{1}{k_j} \prod_{m=j}^{n} q_m \right) \quad (8)$$

$$S_k = S \prod_{j=1}^{k} q_j - J \sum_{l=1}^{k} \frac{1}{k_l} \prod_{j=l}^{k} q_j \quad (9)$$

Maximizing $J/E_T$ gives the following enzyme distribution (63, 64)

$$\frac{E_i}{E_T} = \left( \sqrt{\frac{1}{V_i^+} \prod_{j=1}^{i-1} \frac{1}{q_j}} \right) \Big/ \left( \sum_{k=1}^{n} \sqrt{\frac{1}{V_k^+} \prod_{j=1}^{k-1} \frac{1}{q_j}} \right) \quad (10)$$

In order to compare the results obtained from different assumptions we consider n identical reactions, with equipotent rates and constants: $K_i^+ = K^+$, $V_i^+ = V^+$, $K_i^- = K^-$, $V_i^- = V^-$.

4.1. Equipotent Forward and Backward Rates, q=1

The optimal enzyme distribution in this case is $E_i = E_T/n$. Substituting in eq. 8 gives $$\frac{J}{E_T} = \frac{S}{E_T \frac{1}{k} n} = \frac{S}{E_T \frac{K}{V E_T} n} = \frac{1}{n^2} V \frac{S}{K} \quad (11)$$

4.2. Forward Reactions Faster than Backward Reactions, q>1

$$\frac{J}{E_T} = \left( S \prod_{j=1}^{n} q_j \right) \Big/ \left( E_T \sum_{j=1}^{n} \frac{1}{k_j} \prod_{m=j}^{n} q_m \right) = \quad (12)$$

$$S q^n \Big/ \left( E_T \frac{K}{V} \sum_{j=1}^{n} \frac{q^{n-j+1}}{E_j} \right) = V \frac{S}{K} \Big/ \left( E_T \sum_{j=0}^{n-1} \frac{1}{q^j E_{j+1}} \right)$$

4.2.1. Optimal Enzyme Distribution $$\frac{E_i}{E_T} = \quad (13)$$

$$\left( \sqrt{\frac{1}{q^{i-1}}} \right) \Big/ \left( \sum_{k=1}^{n} \sqrt{\frac{1}{q^{k-1}}} \right) = \frac{1}{q^{\frac{i}{2}}} \Big/ \left( \sum_{k=1}^{n} \left(\frac{1}{q}\right)^{\frac{k}{2}} \right) = \frac{1}{q^{\frac{i}{2}}} \frac{q^{\frac{n+1}{2}} - q^{\frac{2}{n}}}{q^{\frac{n}{2}} - 1}$$

Substitution of eq. 13 in eq. 12 yields $$\frac{J}{E_T} = V \frac{S}{K} \Big/ \left( \sum_{j=0}^{n-1} \frac{q^{\frac{j+1}{2}}}{q^j} \frac{q^{\frac{n}{2}} - 1}{q^{\frac{n+1}{2}} - q^{\frac{n}{2}}} \right) = V \frac{S}{K} E_t \left( \frac{q^{\frac{n}{2}} - q^{\frac{n-1}{2}}}{q^{\frac{n}{2}} - 1} \right)^2 \quad (14)$$

which, for q>1, is a monotonically increasing function with q that obeys:

$$\frac{1}{n^2} V \frac{S}{K} < \frac{J}{E_t} < V \frac{S}{K} \quad (15)$$

$$\frac{J}{E_t} \xrightarrow{q \to 1} \frac{1}{n^2} V \frac{S}{K}, \quad \frac{J}{E_t} \xrightarrow{q \to \infty} V \frac{S}{K} \quad (16)$$

4.2.2. Non-Optimal, Uniform, Enzyme Distribution $E_i = 1/n$ $$\frac{J}{E_T} = V \frac{S}{K} \Big/ \left( n \sum_{j=0}^{n-1} \frac{1}{q^j} \right) = V \frac{S}{K} \frac{1}{n} \frac{q^n - q^{n-1}}{q^n - 1} \quad (17)$$

which, for q>1, is a monotonically increasing function with q that obeys:

$$\frac{1}{n^2} V \frac{S}{K} < \frac{J}{E_T} < \frac{1}{n} V \frac{S}{K}, \quad (18)$$

$$\frac{J}{E_T} \xrightarrow{q \to 1} \frac{1}{n^2} V \frac{S}{K}, \frac{J}{E_T} \xrightarrow{q \to \infty} \frac{1}{n} V \frac{S}{K} \quad (19)$$

4.2.3 Osmotic Constraint

Still considering a linear-regime and optimizing $J/E_T$, we add another constraint, on the overall concentration of the intermediates: $\Sigma S_i = \Omega^0$.

In such case and when $q \to \infty$ the optimal enzyme distribution obeys (63)

$$\frac{E_1}{E_T} = \frac{\Omega^0}{\Omega^0 + n^2 S}, \frac{E_i}{E_T} = \frac{nS}{\Omega^0 + n^2 S} \quad (2 \le i \le n) \quad (20)$$

In such case the specific flux is given by $$\frac{J}{E_T} = V \frac{S}{K} \bigg/ \left( \sum_{j=0}^{n-1} \frac{1}{q^j E_{j+1}} \right) = \quad (21)$$

$$V \frac{S}{K} \bigg/ \left[ (\Omega^0 + n^2 S) \left( \frac{1}{\Omega^0} + \frac{1}{nS} \frac{q^{n-1}-1}{q^n - q^{n-1}} \right) \right] \xrightarrow{q \to \infty} V \frac{S}{K} \frac{\Omega^0}{\Omega^0 + n^2 S}$$

We shell now assume (practically) $\Omega^0 \sim S$ $$\frac{J}{E_T} \xrightarrow[\Omega_S^0 \to 1]{} \frac{1}{1+n^2} V \frac{S}{K} \quad (22)$$

5. Summary of Analysis

Table 13 shown below compares the specific fluxes obtained using different assumptions.

The factor S/K (>1) separates the results of the linear-order assumption from the zero-order assumption, which indeed corresponds to the independence of the second assumption on both substrate concentration and Michaelis constants.

The pre-factors that emerge from the different assumption sets seem to lie between the asymptotes $1/n^2$ and $1/n$. Indeed, the pre-factor of eq. 15 and 16 (linear-order, q>1, optimize enzyme distributions) tends to 1 with increasing q. However, increasing q, in this case, is coupled with an increased imbalance of the enzymes' distribution and with a superlinearly increase of the overall intermediate concentrations (63), which very quickly break the liner-order assumption. In-vivo, those effects are unrealistic. Indeed, introducing an osmotic constraint results in pre-factor of $1/(1+n^2)$, when $q \to \infty$. Therefore, the pre-factor $1/n$, which corresponds to the assumptions we have used in the paper, seems to serve as upper limit estimation.

To conclude, our simplistic analysis indeed indicates that the pathway specific activity is an upper limit estimation of the specific flux of a pathway.

TABLE 13

| Comments | Specific Flux | Assumptions |
|---|---|---|
| PSA is a function of V and *n*. Michaelis constants and intermediate concentrations are not relevant. | $\frac{J}{E_T} = V \frac{1}{n}$ | Zero-order regime $(S_{i-1} \gg K_i^+)$<br><br>Negligible reverse reaction $\left( \frac{V_i^+}{K_i^+} \gg \frac{V_i^-}{K_i^-} \right)$<br><br>Enzyme distribution is fixed $\left( \frac{E_1}{E_T} = \frac{\left(\frac{1}{V_i^+}\right)}{\sum_{j=1}^{i} \left(\frac{1}{V_j^+}\right)} \right)$ |
| | $\frac{J}{E_T} = \frac{1}{n^2} V \frac{S}{K}$ | Linear-order regime $\left( S_i^{+\square} \ll K_i^{+\square} \right)$<br><br>Forward and backward reactions are equipotent (q = 1)<br><br>The optimal enzyme distribution is uniform $\left( E_i = \frac{E_t \sqrt{\cdots}}{\sum_{k=1}^{n} \sqrt{\cdots}} = \frac{1}{n} \right)$ |

TABLE 13-continued

| Comments | Specific Flux | Assumptions |
|---|---|---|
| The total intermediates concentration increases superlinearly with increasing q. See text. | $\frac{1}{n^2} V \frac{S}{K} < \frac{J}{E_T} < V \frac{S}{K}$ | Linear-order regime $\left(S_i^{+\square} \ll K_i^{+\square}\right)$<br><br>Forward reaction is faster than the backward (q > 1)<br><br>Optimal enzyme distribution<br><br>$\left(E_i = \dfrac{E_t \sqrt{\cdots}}{\sum_{k=1}^{n} \sqrt{\cdots}}\right)$ |
| | $\frac{1}{n^2} V \frac{S}{K} < \frac{J}{E_T} < \frac{1}{n} V \frac{S}{K}$ | Linear-order regime $\left(S_i^{+\square} \ll K_i^{+\square}\right)$<br><br>Forward reaction is faster than the backward (q > 1)<br><br>Uniform enzyme distribution<br><br>$\left(E_i = \dfrac{1}{n}\right)$ |
| | $\dfrac{J}{E_T} = \dfrac{1}{1+n^2} V \dfrac{S}{K}$ | Linear-order regime $\left(S_i^{+\square} \ll K_i^{+\square}\right)$<br><br>Forward reaction is faster than the backward (q → ∞)<br><br>Osmotic constraint ($\Sigma S_i = \Omega^0$, $\Omega^0 \sim S$)<br><br>Optimal enzyme distribution<br><br>$\left(\dfrac{E_1}{E_T} = \dfrac{\Omega^0}{\Omega^0 + n^2 S}, \dfrac{E_1}{E_T} = \dfrac{nS}{\Omega^0 + n^2 S}\right)$ |

II. The Stoichiometric Coefficients of the Reductive Pentose Phosphate Cycle's Enzymes In order to determine the stoichiometric coefficients of the enzymes in the reductive pentose phosphate (rPP) cycle we have assumed a zero net flux of each metabolite (a steady-state assumption). Therefore, we can build a set of linear equations that describes the relation between the different enzymatic rates. This set is represented by the following equation: $S_{C \times R} \cdot v_{R \times i} = b_{C \times i}$, where S is the stoichiometry matrix, v is the flow vector (which equals the stoichiometric coefficients), b is a vector corresponding to the change in the concentrations of each compound, C is the number of compounds and R is the number of reaction.

As shown in FIG. 5A, the carboxylase reaction flux of RUBISCO is marked by $v_i$, while the oxygenase reaction flux is marked by $v'_1$. The carboxygenase reaction of RUBISCO generate two molecules of glycerate-3-phosphate (G3P) from a single molecule of ribulose-1,5,-bisphosphate (RuBP). The oxygenase reaction, however, produces 1.5 moles of G3P for every mole of RuBP. One mole is formed directly from the oxygenase reaction and another half is produced by the photorespiration pathway that condenses two glycolate-2-phosphate molecules, which were formed by the oxygenase reaction.

Therefore, the stochiometry matrix, S, is given as follows:

TABLE 14

| Reaction # | | | | | | | | | | | | | | |
|---|---|---|---|---|---|---|---|---|---|---|---|---|---|---|
| 13 | 12 | 11 | 10 | 9 | 8 | 7 | 6 | 5 | 4 | 3 | 2 | 1' | 1 | Compound |
| 0 | 0 | 0 | 0 | 0 | 0 | 0 | 0 | 0 | 0 | 0 | −1 | 1.5 | 2 | G3P |
| 0 | 0 | 0 | 0 | 0 | 0 | 0 | 0 | 0 | 0 | −1 | 1 | 0 | 0 | GBP |
| 0 | 0 | 0 | −1 | 0 | 0 | −1 | 0 | −1 | −1 | 1 | 0 | 0 | 0 | GA3P |
| 0 | 0 | 0 | 0 | 0 | −1 | 0 | 0 | −1 | 1 | 0 | 0 | 0 | 0 | DHAP |
| 0 | 0 | 0 | 0 | 0 | 0 | 0 | −1 | 1 | 0 | 0 | 0 | 0 | 0 | FBP |
| 0 | 0 | 0 | 0 | 0 | 0 | −1 | 1 | 0 | 0 | 0 | 0 | 0 | 0 | F6P |
| 0 | 0 | 0 | 0 | 0 | −1 | 1 | 0 | 0 | 0 | 0 | 0 | 0 | 0 | E4P |
| 0 | 0 | 0 | 0 | −1 | 1 | 0 | 0 | 0 | 0 | 0 | 0 | 0 | 0 | SBP |
| 0 | 0 | 0 | −1 | 1 | 0 | 0 | 0 | 0 | 0 | 0 | 0 | 0 | 0 | S7P |
| 0 | −1 | 0 | 1 | 0 | 0 | 1 | 0 | 0 | 0 | 0 | 0 | 0 | 0 | X5P |
| 0 | 0 | −1 | 1 | 0 | 0 | 0 | 0 | 0 | 0 | 0 | 0 | 0 | 0 | R5P |
| −1 | 1 | 1 | 0 | 0 | 0 | 0 | 0 | 0 | 0 | 0 | 0 | 0 | 0 | Ru5P |
| 1 | 0 | 0 | 0 | 0 | 0 | 0 | 0 | 0 | 0 | 0 | 0 | −1 | −1 | RuBP |

Glyceraldehyde-3-phosphate (GA3P) is the product of the rPP cycle and therefore the outward flux $v_{out}$ is a flux of GA3P leaving the cycle (FIG. 5A).

The vector of the change in the concentrations of each compound, b, is hence taken to be:

TABLE 15

| | | |
|---|---|---|
| 0 | G3P | Compound |
| 0 | GBP | |
| 1 | GA3P | |
| 0 | DHAP | |
| 0 | FBP | |
| 0 | F6P | |
| 0 | E4P | |
| 0 | SBP | |
| 0 | S7P | |
| 0 | X5P | |
| 0 | R5P | |
| 0 | Ru5P | |
| 0 | RuBP | |

To find the stoichiometric coefficient d, corresponding to the flow vector, v, we need to solve $S_{C\times R} \cdot v_{R\times i} = b_{C\times i}$.

Let us assume a ratio between RUBISCO oxygenase ($v'_1$) and carboxygenase ($v_1$) reactions of c.

Solving the equation we get the flux vector v as shown below, where $\lambda=(1+c)/(1-0.5c)$. We chose two representing c values. The first is c=0, corresponding to no photorespiration (C4 and CAM plants, elevated $CO_2$ concentration, $CO_2$ concentrating mechanisms ext.). Secondly, we took the biologically relevant c=0.25, corresponding to terrestrial C3 plants. The resulting vector v matches the stoichiometric coefficients of the rPP cycle's enzymes.

TABLE 16

| Reaction # | | | | | | | | | | | | | |
|---|---|---|---|---|---|---|---|---|---|---|---|---|---|
| 13 | 12 | 11 | 10 | 9 | 8 | 7 | 6 | 5 | 4 | 3 | 2 | 1' | 1 |
| 3λ | 2λ | λ | λ | λ | λ | λ | λ | λ | 2λ | 5λ + 1 | 5λ + 1 | (λ + 2)c | λ + 2 |
| 3 | 2 | 1 | 1 | 1 | 1 | 1 | 1 | 1 | 2 | 6 | 6 | 0 | 3 c = 0 |
| 4.29 | 2.86 | 1.43 | 1.43 | 1.43 | 1.43 | 1.43 | 1.43 | 1.43 | 2.86 | 8.15 | 8.15 | 0.86 | 3.43 c = 0.25 |

III. Correlation Between Pathway Specific Activity and Number of Enzymes

The simplicity of a pathway, which corresponds to the number of enzymes it utilizes, is often taken as an indicator for its specific flux. The number of enzymes is expected to be correlated to the total concentration of the pathway's enzymes; therefore simplicity should correlate with the pathway specific flux.

To test this assumption we analyzed the correlation between the pathway specific activities and the (total) number of enzymes of the non-ferredoxin-oxidoreductase-containing pathways, as given in Table 1, FIG. 14 and shown in FIG. 11. We did not include the ferredoxin-oxidoreductase pathways because they have artificially higher specific activities stemming from our lack of knowledge regarding the kinetic properties of the ferredoxin-oxidoredcutase enzymes.

The linear-correlation between the two criteria gave $R^2 \sim 0.18$ with a gradient of ~0.015. Using a Z-test we get $z=R^2 \cdot (n-3)^{0.5}=0.59$, which gives p-value of 0.28. Therefore, no significant correlation could be established between those criteria and hence the simplicity of a pathway cannot serve as a reliable indicator for its pathway specific activity.

E. Pathway Analysis Methods—Metabolic Compatibility
I. Functional Analysis of the Effects of Novel Cycles on the Metabolic Network
1. The Model In designing alternative $CO_2$ assimilation pathways, it is important to predict how such pathways will integrate into the rest of the metabolic network and how they influence closely connected metabolic pathways. Constraint-based modeling provides a reliable means of doing such an analysis. In constraint-based modeling of metabolic networks, successive layers of known constraints can be outlined to find a solution space of allowable phenotypes. Such constraints include all known chemical reactions for an organism, metabolic reaction stoichiometry, allowed reaction directionality, and known uptake and secretion rates. While this modeling framework does not incorporate information about kinetics, it can provide accurate measures of growth yield, secretion products, the viability of environmental and genetic perturbations and many additional insights.

To investigate the effects that the synthetic pathways exert on the entire metabolic network of a photosynthetic organism, a number of the proposed cycles in this example have been inserted into the metabolic network reconstruction of *Chlamydamonas rhinhartti*. For each cycle, the model is set up by removing Rubisco, adding the cycle, and running the simulations under the same environmental conditions as published (aerobic conditions with ample light and $CO_2$), with few modifications: Ferredoxin located in the thylakoid lumen was moved into the chloroplast stroma, as supported by the literature. In addition, mitochondrial lactate dehydrogenase (UQ containing), Isocitrate lyase, and carbonic anhydrase were changed from irreversible to reversible since no literature evidence could be found to support the irreversible designation. Adenylate kinase was also added to the chloroplast since 43% of this enzyme activity was localized to the chloroplast.

2. Flux Balance Analysis and the "Committing Reactions" of the Carbon Fixation Pathways Flux balance analysis (FBA) was used for determining a measure of the stoichiometric and topological efficiency of each cycle in the context of the *Chlamydomonas* metabolic network. FBA is a useful tool to compute growth yields and likely secretion products. For each cycle, FBA was used to compute these quantities given a constraint on the "committing reaction". A "committing reaction", by definition, is the reaction from the pathway of interest which connects the carbon flux in the pathway to the rest of the metabolic network. In each simulation, the committing reaction was constrained to a flux of 5 mmol carbon atoms per g Dry Weight biomass per hour. To compare the efficiency of different cycles, the FBA results were used to compute a molar ratio of secretion products to biomass production under a defined committing reaction flux (FIG. 12, Table 1). Thereby, this measure allows the comparison of how efficiently the various cycles convert $CO_2$ into biomass.

The following reactions were used as committing reactions, followed by the respective pathways:

Rubisco: Wild Type

Glyoxylate Carboligase: MOG/lactate, MOG/alanine, KGS-ICDH, PyrS-ME, PyrS-PEPC, AcC-ICDH/glycerate & PrC-KGS/Glutamate pathways.

Citramalyl-CoA lyase: 3-HP & AcC-PrC-KGS/Glutamate pathways.

Carboxytransferase: AcC-PrC/Citrate

Acetoacetyl-CoA transporter: 3-HP/4-HB pathway

3. The Choice of Electron Acceptor has the Greatest Effect on the Growth Rate

In silico, wild-type *Chlamydomonas* successfully assimilates $CO_2$ and converts all of it to biomass. When Rubisco is removed and synthetic pathways are added, the parameter which affects biomass the most is the electron carriers employed in each cycle. In general, cycles which use only NADPH or ferredoxin are capable of the same growth yield as wild type *Chlamydomonas* (FIG. 12, Table 1). The only exceptions are cases in which the end product of the cycle is acetyl-CoA (as discussed below).

Cycles which employ the electron carriers FAD or ubiquinone (UQ) consistently have a lower growth yield since the pathways needed to recycle the reduced ubiquinone pass the electrons onto acetyl-coa which is converted into ethanol and secreted. A similar phenomenon occurs when acetyl-CoA serves as the product of the carbon fixation cycle. This is because the metabolism of acetyl-CoA leads to an increased usage of $NAD^+$, thereby increasing the amount of NADH which must be recycled. The primary mechanisms which effectively replenish the pool of $NAD^+$ are ethanol production and oxidative phosphorylation. Indeed, in both cases mitochondrial ATP synthase carries a higher flux than needed for maximal growth. However, this still is unable to recycle all of the NADH; therefore, the other mechanism of ethanol production is needed to maintain steady state amounts of $NAD^+/NADH$. The molar ratios of secreted carbon to fixed carbon, for the pathways analyzed, are given in FIG. 12, Table 1.

4. The Replacement of Rubisco does not Significantly Change the Overall Candidate Flux Distributions It has been previously demonstrated that cells tend to minimize the changes in flux vales following a genetic perturbation in the metabolic network. This occurs because the genetic changes often require the differential expression of many enzymes which may or may not correspond to established regulatory patterns. If a large portion of the metabolic network undergoes significant changes, this can inhibit growth until the strain evolves and adapts to the new network topology. In more extreme conditions, such shifts in the metabolic flux distributions may inhibit the acceptance of such pathways. Therefore, when replacing natural metabolic pathways, it is beneficial to identify synthetic pathways which minimize the number of reactions that experience a significant change in the range of allowable flux.

To evaluate the extent by which the allowable steady state flux distributions are affected by the replacement of Rubisco with alternative carbon fixation pathways, uniform random sampling of the allowable flux phenotypes is employed here. In this method, instead of searching for the optimal solution as done in FBA, the distribution of allowable fluxes for all reactions are found for the entire solution space. However, since it is preferable to only look at the constraints on higher growth, only the space of phenotypes which maintain at least 95% of the optimal growth yield as computed using FBA is analyzed here (this was repeated for 90% and 99% of the optimal growth yield; however, qualitative results did not change). For all reactions which were consistent between the two models, a p-value was computed for the null hypothesis that the two distributions overlap. The number of significantly different reactions was then determined using a FDR of 0.05. The percents of fluxes that were changed significantly by the addition of the synthetic pathways are given in FIG. 12, Table 1, for each analyzed cycle.

Interestingly, the MOG pathways require the fewest number of reactions to significantly change the allowable flux range (as low as 12-13%; FDR=0.05). On average, ferredoxin containing cycles witness slightly higher numbers of significantly changing reactions. Ubiquinione or FAD-containing cycles and cycles which produce acetyl-CoA, however, demonstrate significantly higher changes in the allowable flux distributions (FIG. 12, Table 1). Therefore we predict that NADPH or ferredoxin containing pathways will be more likely to be accepted and require less time for adaptation to the new distribution of metabolite fluxes throughout the metabolic network.

5. Randomly Swapping NADPH to NADH Occasionally Affects the Growth Rate

Multiple enzymes may employ different electron donors at different efficiencies, or have isoforms which can use different electron donors. Two commonly interchangeable electron donors are NADH and NADPH. To probe how varying the usage of these carriers affects the efficiency, reactions requiring such an electron carrier were randomly chosen throughout the network. Electron carriers were changed from NADPH to NADH and the growth yield was computed. In the majority of the changes there is little or no affect on the growth rate for the various cycles. However, a select few enzymes, when changed, affected growth in one or more cycle. Those enzymes include:

Lactate dehydrogenase (MOG/lactate pathways);
Succinate dehydrogenase (3-HP and 3-HP/4-HB pathways)
Isocitrate dehydrogenase (3-HP/4-HB, PyrS-ME & PyrS-PEPC pathways);
GASP dehydrogenase (phosphorylating) (PyrS-ME & PyrS-PEPC pathways);
Malate dehydrogenase (PyrS-ME & PyrS-PEPC pathways);
Malic enzyme (PyrS-ME pathway);
Malonyl-CoA reductase (3-HP cycle);

This suggests that in most cases cycles are robust to changes in similar electron carriers, but also that these few enzymes can be adjusted to produce more biomass or secretion products as needed.

6. Conclusion

Combined, the results from analyzing a subset of synthetic cycles in the context of the *Chlamydomonas* metabolic network suggests that glyoxylate-producing cycles employing NADPH as electron donors, such as the MOG cycles, will have a growth yield comparable to network with the rPP cycle. These cycles are topologically the most efficient, and disrupt the allowable flux distributions the least. Combined with the prediction of improved kinetics in comparison to the rPP cycle, these cycles demonstrate great promise for the optimization of $CO_2$ sequestration and biomass production. Alternatively, the UQ-containing cycles may be used for the production of useful secretion products such as biofuels.

TABLE 17

| E.C. number | Enzyme |
|---|---|
| 1.1.1.28 | Lactate Dehydrogenase |
| 4.2.1.54 | Lactoyl-CoA Dehydratase |
| 1.1.1.37/82 | Malate Dehydrogenase (NAD/NADP) |
| 2.3.3.9 | Malate Synthase |

TABLE 17-continued

| E.C. number | Enzyme |
|---|---|
| 1.1.1.38/39/40 | Malic enzyme |
| 1.1.1.— + | Malonyl-CoA Reductase |
| 1.2.1.— | (Hydroxypropionate-forming) |
| 1.2.1.— | Malonyl-CoA Reductase |
|  | (Malonatesemialdehyde-forming) |
| 4.1.3.24 | Malyl-CoA Lyase |
| 6.2.1.9 | Malyl-CoA Synthetase |
| ND | Mesaconyl-CoA Hydratase |
| 4.3.1.2 | Methylaspartate Ammonia-Lyase |
| 6.4.1.4 | Methylcrotonyl-CoA Carboxylase |
| 2.1.3.1 | Methylmalonyl-CoA Carboxytransferase |
| 5.1.99.1 | Methylmalonyl-CoA Epimerase |
| 5.4.99.2 | Methylmalonyl-CoA Mutase |
| 4.1.3.24 | Methylmalyl-CoA Lyase |
| ND | Methylsuccinyl-CoA Dehydrogenase |
| 6.2.1.8. | Oxalate CoA Ligase |
| 3.7.1.1 | Oxaloacetase |
| 4.1.1.31 | PEP Carboxylase |
| 2.7.2.3 | Phosphoglycerate Kinase |
| 5.4.2.1 | Phosphoglycerate Mutase |
| 2.7.1.19 | Phosphoribulokinase |
| 2.8.3.1 | Propionate CoA Transferase |
| 6.4.1.3 | Propionyl-CoA Carboxylase |
| 6.2.1.— + | Propionyl-CoA Synthase |
| 4.2.1.— + |  |
| 1.3.1.— |  |
| 6.4.1.1 | Pyruvate Carboxylase |
| 1.2.7.1 | Pyruvate Synthase |
| 2.7.9.2 | Pyruvate Water (Phosphate) Dikinases |
| (2.7.9.1) |  |
| 5.3.1.6 | Ribose-5-Phosphate Isomerase |
| 4.1.1.39 | Ribulose-Bisphosphate Carboxylase |
| 5.1.3.1 | Ribulose-Phosphate 3-Epimerase |
| 3.1.3.37 | Sedoheptulose-Bisphosphatase |
| 1.3.5.1/ | Succinate Dehydrogenase/Fumarate Reductase |
| 1.3.99.1/ |  |
| 1.3.1.6 |  |
| 2.8.3.7 | Succinate-citramalate CoA-transferase |
| ND | Succinyl-CoA Reductase |
| 6.2.1.4/5 | Succinyl-CoA Synthetase |
| 1.1.1.60 | Tartronate-Semialdehyde Reductase |
| 2.2.1.1 | Transketolase |
| 5.3.1.1 | Triose-Phosphate Isomerase |
| 1.1.99.2 | 2-Hydroxyglutarate Dehydrogenase |
| 2.3.3.11 | 2-Hydroxyglutarate Synthase |
| 4.2.1.— | 2-Hydroxyglutaryl-CoA Dehydratase |
| 6.4.1.7 | 2-Ketoglutarate Carboxylase |
| 1.2.7.3 | 2-Ketoglutarate Synthase |
| 4.2.1.34 | 2-Methylmalate Dehydratase |
| 1.1.1.157 | 3-Hydroxybutyryl-CoA Dehydrogenase |
| 1.1.1.61 | 4-Hydroxybutyrate Dehydrogenase |
| ND | 4-Hydroxybutyryl-CoA Dehydratase |
| ND | 4-Hydroxybutyryl-CoA Synthetase |
| 2.8.3.8 | Acetate:Succinate CoA-Transferase |
| 2.3.1.9/16 | Acetyl-CoA C-Acyltransferase |
| 6.4.1.2 | Acetyl-CoA Carboxylase |
| 6.2.1.13 | Acetyl-CoA Synthetase |
| 4.2.1.3 | Aconitate Hydratase |
|  | Alanine Aminomutase |
| 4.3.1.1 | Aspartate Ammonia-Lyase |
| 2.6.1.1 | Aspartate Transaminase |
| 2.3.3.8 | ATP Citrate Lyase |
| 2.6.1.18 | beta-Alanine-Pyruvate Transaminase |
| 4.1.3.22 | Citramalate Lyase |
| 4.1.3.25 | Citramalyl-CoA Lyase |
| 2.3.3.1 | Citrate Synthase |
| ND | Crotonyl-CoA Carboxylase/Reductase |
| 4.2.1.11 | Enolase |
| 4.2.1.17/55 | Enoyl-CoA Hydratase (Crotonase) |
| ND | Ethylmalonyl-CoA Epimerase |
| ND | Ethylmalonyl-CoA Mutase |
| 3.1.3.11 | Fructose-Bisphosphatase |
| 4.1.2.13 | Fructose-Bisphosphate Aldolase |
| 4.2.1.2 | Fumarate Hydratase |
| 2.8.3.12 | Glutaconate CoA-Transferase |
| 1.4.1.4 | Glutamate Dehydrogenase (NADPH) |
| 5.4.99.1 | Glutamate Mutase |
| 1.2.1.12/13 | Glyceraldehyde-3P Dehydrogenase (Phosphorylating) |
| 2.7.1.31 | Glycerate Kinase |
| 4.1.1.47 | Glyoxylate Carboligase |
| 1.2.1.17 | Glyoxylate Dehydrogenase |
| 1.1.1.41/42 | Isocitrate Dehydrogenase |
| 4.1.3.1 | Isocitrate Lyase |

Example 3

Practical Implementation

In Vitro Implementation

The capture of inorganic carbon from the atmosphere by industrial means has received significant attention in recent years. Apart from completely chemical approaches, the in vitro reconstitution of the Calvin-Benson Cycle was proposed and pursued as an efficient alternative to perform this goal, while providing voluble bioorganic compounds. The proposed synthetic carbon fixation pathways can achieve the same goal with less enzymatic biomass. Tables 18 and 19 present the enzymatic constituents of such an in vitro carbon fixation system, operating the C4-Glyoxylate/Alanine or C4-Glyoxylate/Lactate pathway, where for each enzyme prokaryotic and eukaryotic alternatives are given, if possible.

To support carbon the enzymatic system should be provided with energized cofactors, namely ATP and NADH and/or NADPH. These cofactors can be regenerated in vitro in various ways. Notably, if one would like to provide reducing power using a single type of electron donor (NADPH only) one should choose malate dehydrogenase from higher plants and lactate dehydrogenase from *Trichomonas* (see Table 18 and 19).

Bacterial Implementation, *E. coli*

Implementing the synthetic carbon fixation pathways in the naturally heterotrophic *E. coli* might be extremely beneficial. Adapting this highly utilized organism to an autotrophic way of life can open new routes for its cultivation in the biotechnology industries and for the production of a large variety of voluble compounds.

Apart from an active carbon fixation pathway the organism will need a sustainable source of energy and reducing power, in order to achieve autotrophy. In most cases through respiration, the source of reducing power will also generate the required energy as long as oxygen is available. $NAD^+$ is the preferred intermediate electron acceptor because it can directly serve both as an electron donor for carbon fixation and as an energy producer when oxidized by *E. coli*'s respiratory electron chain. The two best candidates for providing *E. coli* with reducing power (and energy) are formate and phosphite. The soluble enzyme $NAD^+$-dependent formate dehydrogenase irreversibly oxidizes formate ($E'^0=-430$ mV, and reduces $NAD^+$) (formate cannot be directly assimilated by *E. coli*). The recently discovered enzyme NAD:phosphite oxidoreductase irreversibly oxidizes phosphite to phosphate ($E'^0=-650$ mV) and reduces $NAD^+$. Both enzymes operate under fully aerobic conditions which enable molecular oxygen to serve as the terminal electron acceptor, maximizing the energetic gain of oxidizing the electron donors. Both are used to regenerate NAD(P) and both retain full activity in *E. coli*. Notably, both enzymes were evolved to accept and even prefer NADP over NAD.

A further option is to establish an *E. coli* strain that is capable of growing using electrical power as the sole source of reducing power and energy, where electrodes will supply the cells with electrons. Intact *E. coli* cells cannot directly react with an electrode, but redox dyes can mediate electron transfer from the electrode to the dye and then into cellular metabolism. An excellent example for this is the electronophore neutral red, which was shown to reduce NAD in vivo in the gram-negative bacterium *Actinobacillus succinogenes*. Notably, the organism was shown to grow using reduced neutral red as the sole electron donor for metabolism.

*E. coli* endogenously operates the enzymes Pyruvate Dikinase, PEP Carboxylase, Malate Dehyderogenase, Lactate Dehydrogenase, Glyoxylate Carboligase, Tartronate-Semialdehyde Reductase and Glycerate Kinase.

To implement the C4-Glyoxylate/Alanine pathway in this organism the following foreign enzymes should be expressed: Malyl-CoA Synthetase, Malyl-CoA Lyase, Methylmalonyl-CoA Carboxytransferase, Malonate Semialdehyde Dehydrogenase, Alanine Aminomutase and Beta-Alanine Pyruvate Transaminase. The prokaryotic sources, as appear in Table 18, are more suitable to this host.

To implement the C4-Glyoxylate/Lactate pathway in this organism the following foreign enzymes should be expressed: Malyl-CoA Synthetase, Malyl-CoA Lyase, Methlmalonyl-CoA Carboxytransferase, Malonyl-CoA Reductase, Propionate CoA Transferase, Enoyl-CoA Hydratase and Lactoyl-CoA dehydratase. The prokaryotic sources, as appear in Table 1, are more suitable to this host.

Cyanobacterial Implementation, *Synechocystis* sp. Strain PCC6803

The fresh water cyanobacterium *Synechocystis* sp. strain PCC6803 is an excellent candidate for carbon fixation manipulation. First, being a prokaryote, it is relatively free of compartmentalization issues. In addition, it is easily transformed with foreign DNA. Most importantly, it can attain both autotrophic as well as heterotrophic mode of growth, depending on the availability of light. This metabolic versatility makes this organism an ideal candidate for an extreme metabolic modification, which might become much more difficult in other cyanobacterial strains that can grow only autotrophically and cannot survive without the activity of Rubisco.

*Synechocystis* sp. strain PCC6803 endogenously operates the enzymes Pyruvate Dikinase, PEP Carboxylase, Malate Dehyderogenase, Glyoxylate Carboligase, Tartronate-Semialdehyde Reductase and Glycerate Kinase.

To implement the C4-Glyoxylate/Alanine pathway in this organism the following foreign enzymes should be expressed: Malyl-CoA Synthetase, Malyl-CoA Lyase, Methlmalonyl-CoA Carboxytransferase, Malonate Semialdehyde Dehydrogenase, Alanine Aminomutase and Beta-Alanine Pyruvate Transaminase. The prokaryotic sources, as appear in Table 18, are more suitable to this host.

To implement the C4-Glyoxylate/Lactate pathway in this organism the following foreign enzymes should be expressed: Malyl-CoA Synthetase, Malyl-CoA Lyase, Methlmalonyl-CoA Carboxytransferase, Malonyl-CoA Reductase, Propionate CoA Transferase, Enoyl-CoA Hydratase and Lactoyl-CoA dehydratase. The prokaryotic sources, as appear in Table 18, are more suitable to this host. The enzyme Lactate Dehydrogenase was found to operate in the cyanobacterium *Synechocystis* but was not proved to exist in *Synechocystis*. Therefore, if this enzyme is indeed absent in *Synechocystis*, the *Synechocystis* Lactate Dehydrogenase should be expressed.

If the cycles are to be operated using NADPH as the sole electron donor, malate dehydrogenase from higher plants and lactate dehydrogenase from *Trichomonas* should be also expressed (see Table 18 and 19).

Algae Implementation, *Chlamydomonas reinhardtii*:

*Chlamydomonas reinhardtii* as one of the simplest unicellular, eukaryote, phototrophic organism; which make it a good candidate for carbon fixation modification. While the organism does posses the enzymes PEP Carboxylase, Malate Dehyderogenase and Glycerate Kinase, the former one is not localized to the chloroplast. This will necessitate expressing this endogenous gene with a particular chloroplast targeting signal.

To implement the C4-Glyoxylate/Alanine pathway in this organism the following foreign enzymes should be expressed: Pyruvate Dikinase, Malyl-CoA Synthetase, Malyl-CoA Lyase, Methlmalonyl-CoA Carboxytransferase, Malonate Semialdehyde Dehydrogenase, Alanine Aminomutase, Beta-Alanine Pyruvate Transaminase, Glyoxylate Carboligase and Tartronate-Semialdehyde Reductase. Various sources of these enzymes are given in Table 18. All these genes should be expressed with a chloroplast targeting signal.

To implement the C4-Glyoxylate/Lactate pathway in this organism the following foreign enzymes should be expressed: Pyruvate Dikinase, Malyl-CoA Synthetase, Malyl-CoA Lyase, Methlmalonyl-CoA Carboxytransferase, Malonyl-CoA Reductase, Propionate CoA Transferase, Enoyl-CoA Hydratase, Lactoyl-CoA dehydratase, Lactate Dehydrogenase, Glyoxylate Carboligase and Tartronate-Semialdehyde Reductase. Various sources of these enzymes are given in Table 18. All these genes should be expressed with a chloroplast targeting signal.

C3-Plant Implementation, Tobacco (*Nicotiana*)

Tobacco is one of the most studied C3-plant. While the organism does posses the enzymes Pyruvate Dikinase, PEP Carboxylase, Malate Dehyderogenase and Glycerate Kinase, the former two are not localized to the chloroplast. This will necessitate expressing these endogenous genes with a particular chloroplast targeting signal.

To implement the C4-Glyoxylate/Alanine pathway in this organism the following foreign enzymes should be expressed: Malyl-CoA Synthetase, Malyl-CoA Lyase, Methlmalonyl-CoA Carboxytransferase, Malonate Semialdehyde Dehydrogenase, Alanine Aminomutase, Beta-Alanine Pyruvate Transaminase, Glyoxylate Carboligase and Tartronate-Semialdehyde Reductase. Various sources of these enzymes are given in table 18. All these genes should be expressed with a chloroplast targeting signal.

To implement the C4-Glyoxylate/Lactate pathway in this organism the following foreign enzymes should be expressed: Malyl-CoA Synthetase, Malyl-CoA Lyase, Methlmalonyl-CoA Carboxytransferase, Malonyl-CoA Reductase, Propionate CoA Transferase, Enoyl-CoA Hydratase, Lactoyl-CoA dehydratase, Lactate Dehydrogenase, Glyoxylate Carboligase and Tartronate-Semialdehyde Reductase. Various sources of these enzymes are given in Table 18. All these genes should be expressed with a chloroplast targeting signal.

TABLE 18

The C4-Glyoxylate/Alanine pathway

| Eukaryotic Origin | Prokayotic Origin | EC number | Enzyme |
|---|---|---|---|
| Maize, chloroplast (24, 25) Tobacco (26) | E. coli (20, 21) Synechocystis (22, 23) | 2.7.9.1/2 | Pyruvate Dikinase |
| Maize, chloroplast (30) Tobacco (31) Chlamydomonas (32) | E. coli (27, 28) Synechococcus (29) Synechocystis (22, 23) | 4.1.1.31 | PEP Carboxylase |
| | E. coli (33) Synechocystis (22) Trichomonas ‡ (34) | 1.1.1.37 | NAD Dependent Malate Dehyderogenase |
| Maize, chloroplast (35) Tobacco (36) Chlamydomonas (37) | | 1.1.1.82 | NADP Dependent |
| | Pseudomonas (38, 39) | 6.2.1.9 | Malyl-CoA Synthetase |
| | Pseudomonas (40) | 4.1.3.24 | Malyl-CoA Lyase |
| Wheat germs (43, 44) | Propionibacterium (41, 42) | 2.1.3.1 | Methylmalonyl-CoA Carboxytransferase |
| | Metallosphaera (45) Sulfolobus (45) | — | Malonate Semialdehyde Dehydrogenase |
| | Bacillus † (46, 47) Clostridium †† (48, 49) | — | Alanine Aminomutase |
| Wax bean, cotyledons (52) | Pseudomonas (50) Bacillus (51) | 2.6.1.18 | Beta-Alanine Pyruvate Transaminase |
| | E. coli (53) Synechocystis (54) | 4.1.1.47 | Glyoxylate Carboligase |
| | E. coli (55) Synechocystis (54) | 1.1.1.60 | Tartronate-Semialdehyde Reductase |
| Maize, chloroplast (57) Arabidopsis, chloroplast (58) Chlamydomonas, chloroplast (58) | E. coli (56) Synechocystis (54) | 2.7.1.31 | Glycerate Kinase |

† Evolved from Bacillus subtilis lysine aminomutase
†† Clostridium subterminale lysine aminomutase can catalyze also the alanine amniomutase reaction, oxygen sensitive
‡ A bifunctional enzyme, catalyzing both malate and lactate oxidation.

TABLE 19

The C4-Glyoxylate/Lactate pathway

| Eukaryotic Origin | Prokayotic Origin | EC number | Enzyme |
|---|---|---|---|
| Maize, chloroplast (24, 25) Tobacco (26) | E. coli (20, 21) Synechocystis (22, 23) | 2.7.9.1/2 | Pyruvate Dikinase |
| Maize, chloroplast (30) Tobacco (31) Chlamydomonas (32) | E. coli (27, 28) Synechococcus (29) Synechocystis (22, 23) | 4.1.1.31 | PEP Carboxylase |
| | E. coli (33) Synechocystis (22) Trichomonas ‡ (34) | 1.1.1.37 | NAD Dependent Malate Dehyderogenase |

TABLE 19-continued

The C4-Glyoxylate/Lactate pathway

| Eukaryotic Origin | Prokayotic Origin | EC number | Enzyme |
|---|---|---|---|
| Maize, chloroplast (35) Tobacco (36) *Chlamydomonas* (37) | | 1.1.1.82 | NADP Dependent |
| | *Pseudomonas* (38, 39) | 6.2.1.9 | Malyl-CoA Synthetase |
| | *Pseudomonas* (40) | 4.1.3.24 | Malyl-CoA Lyase |
| Wheat germs (43, 44) | *Propionibacterium* (41, 42) | 2.1.3.1 | Methlmalonyl-CoA Carboxytransferase |
| | *Chloroflexus* (59) | — | Malonyl-CoA Reductase |
| | *Clostridium* (60, 61) | 2.8.3.1 | Propionate CoA Transferase |
| | *E. coli* (62, 63) | 4.2.1.17/55 | Enoyl-CoA Hydratase |
| Pigeon (65) | *Clostridium* † (64) *Pseudomonas* (65) | 4.2.1.54 | Lactoyl-CoA dehydratase |
| | *E. coli* (66) *Synechococcus* (67) *Trichomonas* ‡ (34) | 1.1.1.28 | NAD Dependent Lactate Dehydrogenase |
| | *Bacillus* †† (68) | | NADP Dependent |
| | *E. coli* (53) *Synechocystis* (54) | 4.1.1.47 | Glyoxylate Carboligase |
| | *E. coli* (55) *Synechocystis* (54) | 1.1.1.60 | Tartronate-Semialdehyde Reductase |
| Maize, chloroplast (57) *Arabidopsis*, chloroplast (58) *Chlamydomonas*, chloroplast (58) | *E. coli* (56) *Synechocystis* (54) | 2.7.1.31 | Glycerate Kinase |

† Oxygen sensitive
†† Accepts both NAD and NADP
‡ A bifunctional enzyme, catalyzing both malate and lactate oxidation.

REFERENCES

1. Chakrabarti S, Bhattacharya S, & Bhattacharya S K (2003) Immobilization of D-ribulose-1,5-bisphosphate carboxylase/oxygenase: a step toward carbon dioxide fixation bioprocess. *Biotechnol Bioeng* 81(6):705-711.
2. Bhattacharya S, Schiavone M, Gomes J, & Bhattacharya S K (2004) Cascade of bioreactors in series for conversion of 3-phospho-D-glycerate into D-ribulose-1,5-bisphosphate: kinetic parameters of enzymes and operation variables. *J Biotechnol* 111(2):203-217.
3. Mahato S, et al. (2004) Potential use of sugar binding proteins in reactors for regeneration of CO2 fixation acceptor D-Ribulose-1,5-bisphosphate. *Microb Cell Fact* 3(1):7.
4. Wichmann R & Vasic-Racki D (2005) Cofactor Regeneration at the Lab Scale. *Technology Transfer in Biotechnology*, Advances in Biochemical Engineering/Biotechnology, (Springer Berlin/Heidelberg), Vol 92, pp 225-260.
5. Unden G & Bongaerts J (1997) Alternative respiratory pathways of *Escherichia coli*: energetics and transcriptional regulation in response to electron acceptors. *Biochim Biophys Acta* 1320(3):217-234.
6. Thauer R K, Jungermann K, & Decker K (1977) Energy conservation in chemotrophic anaerobic bacteria. *Bacteriol Rev* 41(1): 100-180.
7. Friedebold J & Bowien B (1993) Physiological and biochemical characterization of the soluble formate dehydrogenase, a molybdoenzyme from *Alcaligenes eutrophus*. *J Bacteriol* 175(15):4719-4728.
8. Costas A M, White A K, & Metcalf W W (2001) Purification and characterization of a novel phosphorus-oxidizing enzyme from *Pseudomonas stutzeri* WM88. *J Biol Chem* 276(20):17429-17436.
9. Vrtis J M, White A K, Metcalf W W, & van der Donk W A (2001) Phosphite dehydrogenase: an unusual phosphoryl transfer reaction. *J Am Chem Soc* 123(11):2672-2673.
10. van der Donk W A & Zhao H (2003) Recent developments in pyridine nucleotide regeneration. *Curr Opin Biotechnol* 14(4):421-426.
11. Gul-Karaguler N, Sessions R B, Clarke A R, & Holbrook J J (2001) A single mutation in the NAD-specific formate dehydrogenase from *Candida methylica* allows the enzyme to use NADP *Biotechnology Letters* 23(4):283-287.
12. Serov A E, Popova A S, Fedorchuk V V, & Tishkov V I (2002) Engineering of coenzyme specificity of formate dehydrogenase from *Saccharomyces cerevisiae*. *Biochem J* 367(Pt 3):841-847.
13. Tishkov V I & Popov V O (2006) Protein engineering of formate dehydrogenase. *Biomol Eng* 23(2-3):89-110.
14. Rissom S, Schwarz-Linek U, Vogel M, Tishkov V I, & Kragl U (1997) Synthesis of chiral var epsilon-lactones in a two-enzyme system of cyclohexanone mono-oxygenase and formate dehydrogenase with integrated bubble-free aeration *Tetrahedron: Asymmetry* 8(15):2523-2526.
15. Woodyer R, van der Donk W A, & Zhao H (2003) Relaxing the nicotinamide cofactor specificity of phosphite dehydrogenase by rational design. *Biochemistry* 42(40):11604-11614.
16. Park D H & Zeikus J G (1999) Utilization of electrically reduced neutral red by *Actinobacillus succinogenes*: physiological function of neutral red in membrane-driven fumarate reduction and energy conservation. *J Bacteriol* 181(8):2403-2410.
17. Park D H, Laivenieks M, Guettler M V, Jain M K, & Zeikus J G (1999) Microbial utilization of electrically reduced neutral red as the sole electron donor for growth and metabolite production. *Appl Environ Microbiol* 65(7): 2912-2917.
18. Anderson S L & McIntosh L (1991) Light-activated heterotrophic growth of the cyanobacterium *Synechocystis* sp. strain PCC 6803: a blue-light-requiring process. *J Bacteriol* 173(9):2761-2767.
19. Peltier J B, et al. (2000) Proteomics of the chloroplast: systematic identification and targeting analysis of lumenal and peripheral thylakoid proteins. *Plant Cell* 12(3):319-341.
20. Narindrasorasak S & Bridger W A (1977) Phosphoenolypyruvate synthetase of *Escherichia coli*: molecular weight, subunit composition, and identification of phosphohistidine in phosphoenzyme intermediate. *J Biol Chem* 252(10):3121-3127.
21. Berman K M & Cohn M (1970) Phosphoenolpyruvate synthetase of *Escherichia coli*. Purification, some properties, and the role of divalent metal ions. *J Biol Chem* 245(20):5309-5318.
22. CyanoBase (*Synechocystis* sp. PCC 6803, GeneView.).
23. Kaneko T, et al. (1996) Sequence analysis of the genome of the unicellular cyanobacterium *Synechocystis* sp. strain PCC6803. II. Sequence determination of the entire genome and assignment of potential protein-coding regions. *DNA Res* 3(3):109-136.
24. Chastain C J, et al. (2000) Further analysis of maize C(4) pyruvate, orthophosphate dikinase phosphorylation by its bifunctional regulatory protein using selective substitutions of the regulatory Thr-456 and catalytic His-458 residues. *Arch Biochem Biophys* 375(1):165-170.
25. Sugiyama T (1973) Purification, molecular, and catalytic properties of pyruvate phosphate dikinase from the maize leaf. *Biochemistry* 12(15):2862-2868.
26. Aoyagi K & Bassham J A (1984) Pyruvate Orthophosphate Dikinase of C3 Seeds and Leaves as Compared to the Enzyme from Maize. *Plant Physiol* 75:387-392.
27. Kai Y, et al. (1999) Three-dimensional structure of phosphoenolpyruvate carboxylase: a proposed mechanism for allosteric inhibition. *Proc Natl Acad Sci USA* 96(3):823-828.
28. Yano M & Izui K (1997) The replacement of Lys620 by serine desensitizes *Escherichia coli* phosphoenolpyruvate carboxylase to the effects of the feedback inhibitors L-aspartate and L-malate. *Eur J Biochem* 247(1):74-81.
29. Chen L M, Omiya T, Hata S, & Izui K (2002) Molecular characterization of a phosphoenolpyruvate carboxylase from a thermophilic cyanobacterium, *Synechococcus vulcanus* with unusual allosteric properties. *Plant Cell Physiol* 43(2): 159-169.
30. Uedan K & Sugiyama T (1976) Purification and Characterization of Phosphoenolpyruvate Carboxylase from Maize Leaves. *Plant Physiol* 57(6):906-910.
31. Koizumi N, Sato F, & Yamada Y (1996) Bacterial production and purification of phosphorylatable phosphoenolpyruvate carboxylase from tobacco. *Biosci Biotechnol Biochem* 60(12):2089-2091.
32. Mamedov T G, Moellering E R, & Chollet R (2005) Identification and expression analysis of two inorganic C- and N-responsive genes encoding novel and distinct molecular forms of eukaryotic phosphoenolpyruvate carboxylase in the green microalga *Chlamydomonas reinhardtii*. *Plant J* 42(6):832-843.
33. Park J S, et al. (2007) *Escherichia coli* malate dehydrogenase, a novel solubility enhancer for heterologous proteins synthesized in *Escherichia coli*. *Biotechnol Lett* 29(10):1513-1518.
34. Wu G, Fiser A, ter Kuile B, Sali A, & Muller M (1999) Convergent evolution of *Trichomonas vaginalis* lactate dehydrogenase from malate dehydrogenase. *Proc Natl Acad Sci USA* 96(11):6285-6290.
35. Kagawa T & Bruno P L (1988) NADP-malate dehydrogenase from leaves of *Zea mays*: purification and physical, chemical, and kinetic properties. *Arch Biochem Biophys* 260(2):674-695.
36. Backhausen J E & Scheiber R (1999) Adaptation of tobacco plants to elevated CO2: influence of leaf age on changes in physiology, redox states and NADP-malate dehydrogenase activity. *Journal of experimental botany* 50(334):665-675.
37. Lemaire S D, et al. (2005) NADP-malate dehydrogenase from unicellular green alga *Chlamydomonas reinhardtii*. A first step toward redox regulation? *Plant Physiol* 137 (2):514-521.
38. Hersh L B (1974) Malate thiokinase. The reaction mechanism as determined by initial rate studies. *J Biol Chem* 249(19):6264-6271.
39. Elwell M & Hersh L B (1979) Substrate-dependent dissociation of malate thiokinase. *J Biol Chem* 254(7): 2434-2438.
40. Hacking A J & Quayle J R (1974) Purification and properties of malyl-coenzyme A lyase from *Pseudomonas* AM1. *Biochem J* 139(2):399-405.
41. Shenoy B C, Xie Y, Sha D, & Samols D (1993) Identification and characterization of a factor which is essential for assembly of transcarboxylase. *Biochemistry* 32(40): 10750-10756.
42. Xie Y, Shenoy B C, Magner W J, Hejlik D P, & Samols D (1993) Purification and characterization of the recombinant 5 S subunit of transcarboxylase from *Escherichia coli*. *Protein Expr Purif* 4(5):456-464.
43. Hatch M D & Stumpf P K (1961) Fat metabolism in higher plants. XVI. Acetyl coenzyme A carboxylase and acyl coenzyme A-malonyl coenzyme A transcarboxylase from wheat germ. *J Biol Chem* 236:2879-2885.
44. Hatch M D & Stumpf P K (1962) Fat Metabolism in Higher Plants. XVII. Metabolism of Malonic Acid & Its alpha-Substituted Derivatives in Plants. *Plant Physiol* 37(2):121-126.
45. Alber B, et al. (2006) Malonyl-coenzyme A reductase in the modified 3-hydroxypropionate cycle for autotrophic carbon fixation in archaeal *Metallosphaera* and *Sulfolobus* spp. *J Bacteriol* 188(24):8551-8559.
46. Chen D, Ruzicka F J, & Frey P A (2000) A novel lysine 2,3-aminomutase encoded by the yodO gene of *bacillus subtilis*: characterization and the observation of organic radical intermediates. *Biochem J* 348 Pt 3:539-549.
47. Liao H H, Gokarn R R, Gort S J, Jessen H J, & Selifonova O (2007) U.S. Pat. No. 7,309,597 B2.
48. Frey P A & Ruzicka F J (2003).

49. Ruzicka F J, Lieder K W, & Frey P A (2000) Lysine 2,3-aminomutase from *Clostridium subterminale* SB4: mass spectral characterization of cyanogen bromide-treated peptides and cloning, sequencing, and expression of the gene kamA in *Escherichia coli*. *J Bacteriol* 182(2):469-476.
50. C. U. I, et al. (2006) One-pot synthesis of aminoalcohols using a de-novo transketolase and beta-alanine: pyruvate transaminase pathway in *Escherichia coli*. *Biotechnol. Bioeng.* 96:559-569.
51. Nakano Y, Tokunaga H, & Kitaoka S (1977) Two omega-amino acid transaminases from *Bacillus cereus*. *J Biochem* 81(5):1375-1381.
52. Stinson R A & Spencer M S (1969) Beta alanine aminotransferase (s) from a plant source. *Biochem Biophys Res Commun* 34(1):120-127.
53. Chang Y Y, Wang A Y, & Cronan J E, Jr. (1993) Molecular cloning, DNA sequencing, and biochemical analyses of *Escherichia coli* glyoxylate carboligase. An enzyme of the acetohydroxy acid synthase-pyruvate oxidase family. *J Biol Chem* 268(6):3911-3919.
54. Eisenhut M, et al. (2006) The plant-like C2 glycolate cycle and the bacterial-like glycerate pathway cooperate in phosphoglycolate metabolism in cyanobacteria. *Plant Physiol* 142(1):333-342.
55. Njau R K, Herndon C A, & Hawes J W (2000) Novel beta-hydroxyacid dehydrogenases in *Escherichia coli* and *Haemophilus influenzae*. *J Biol Chem* 275(49):38780-38786.
56. Doughty C C & Hayashi J A (1975) D-glycerate 3-kinase from *Escherichia coli*. *Methods Enzymol* 42:124-127.
57. Kleczkowski L A & Randall D D (1988) Purification and characterization of D-glycerate 3-kinase from maize leaves. *Planta* 173:221-229.
58. Boldt R, et al. (2005) D-GLYCERATE 3-KINASE, the last unknown enzyme in the photorespiratory cycle in *Arabidopsis*, belongs to a novel kinase family. *Plant Cell* 17(8):2413-2420.
59. Hugler M, Menendez C, Schagger H, & Fuchs G (2002) Malonyl-coenzyme A reductase from *Chloroflexus aurantiacus*, a key enzyme of the 3-hydroxypropionate cycle for autotrophic CO(2) fixation. *J Bacteriol* 184(9):2404-2410.
60. Schweiger G & Buckel W (1984) On the dehydration of (R)-lactate in the fermentation of alanine to propionate by *Clostridium propionicum*. *FEBS Lett* 171(1):79-84.
61. Valentin H E & Steinbuchel A (1994) Application of enzymatically synthesized short-chain-length hydroxy fatty acid coenzyme A thioesters for assay of polyhydroxyalkanoic acid synthases. *Applied Microbiology and Biotechnology* 40(5):699-709.
62. Yang S Y, Li J M, He X Y, Cosloy S D, & Schulz H (1988) Evidence that the fadB gene of the fadAB operon of *Escherichia coli* encodes 3-hydroxyacyl-coenzyme A (CoA) epimerase, delta 3-cis-delta 2-trans-enoyl-CoA isomerase, and enoyl-CoA hydratase in addition to 3-hydroxyacyl-CoA dehydrogenase. *J Bacteriol* 170(6):2543-2548.
63. Agnihotri G & Liu H W (2003) Enoyl-CoA hydratase. reaction, mechanism, and inhibition. *Bioorg Med Chem* 11(1):9-20.
64. Hofmeister A E & Buckel W (1992) (R)-lactyl-CoA dehydratase from *Clostridium propionicum*. Stereochemistry of the dehydration of (R)-2-hydroxybutyryl-CoA to crotonyl-CoA. *Eur J Biochem* 206(2):547-552.
65. Vagelos P R, Earl J M, & Stadtman E R (1959) Propionic acid metabolism. II. Enzymatic synthesis of lactyl pantethine. *J Biol Chem* 234(4):765-769.
66. Dym O, Pratt E A, Ho C, & Eisenberg D (2000) The crystal structure of D-lactate dehydrogenase, a peripheral membrane respiratory enzyme. *Proc Natl Acad Sci USA* 97(17):9413-9418.
67. Sanchez J J, Palleroni N J, & Doudoroff M (1975) Lactate dehydrogenases in cyanobacteria. *Arch Microbiol* 104(1):57-65.
68. Romero S, Merino E, Bolivar F, Gosset G, & Martinez A (2007) Metabolic engineering of *Bacillus subtilis* for ethanol production: lactate dehydrogenase plays a key role in fermentative metabolism. *Appl Environ Microbiol* 73(16):5190-5198.

Example 4

Constructing an Autotrophic Strain of *E. coli* as a Model Organism to Test the Synthetic Carbon Fixation Pathways In order to test and compare the proposed synthetic carbon fixation cycles in vivo, there is a need to find a suitable autotrophic host that is capable of growth when supplied with inorganic carbon, a source of energy and reducing power (electrons). The present inventors will utilize the well-studied model organism, *E. coli*, and adapt it to an autotrophic mode of growth using the classic Calvin-Benson Cycle. Native *E. coli* contains most of the Calvin-Benson Cycle enzymes as part of the pentose phosphate pathway and the gluconeogenesis pathway. In fact, the only two enzymes missing to support a full operational cycle are PRK (phosphorubilokinase) and Rubisco (FIG. 15). These two enzymes from at least two origins, the cyanobacterium *Synechococcus* and the purple-bacterium *Rhodospirillum rubrum*, were successfully expressed in *E. Coli* and showed activity significant enough to affect the host's growth. The Type II Rubisco from *R. rubrum* might be a preferable choice because it can fold correctly in the host even with the low levels of chaperones in the *E. coli* cells. As a further alternative, the present inventors will express an operon of the proteobacteria *Ralstonia eutropha*, which contains all the Calvin-Benson Cycle genes in tandem. To confirm the full operation of the cycle in the host, the present inventors will feed the transformed *E. coli* with $^{13}CO_2$ and follow the $^{13}C$ signal across the cycle using liquid-chromatography mass spectrometry (LC-MS) measurements. If the cycle operates as a whole one can expect to find $^{13}C$ enrichment in triose-phosphates, hexose-phosphates and pentose-phosphates. By using available standard libraries of metabolites, one can identify, with the highest precision, the compounds of interest in the LC-MS output and quantify their concentrations in the host.

To provide *E. coli* with the necessary energy and reducing power (electrons) needed for growth either the enzyme $NAD^+$-dependent formate dehydrogenase or the enzyme $NAD^+$-dependent phosphite dehydrogenase can be used. Both enzymes catalyze irreversible reactions (formate→$CO_2$ or phosphite→phosphate) and both operate under fully aerobic conditions which enable molecular oxygen to serve as the terminal electron acceptor. Both are used to regenerate NAD(P) and are known to retained full activity in *E. coli*.

After the host is proven to operate a functioning carbon fixation cycle and to have a constant energy supply it can be forced to grow using only inorganic carbon. Two parallel approaches may be used: (A) Transferring the cells from a media containing a carbon source to a carbon-free media; (B) Decreasing the carbon source concentration gradually until it becomes negligible.

Establishing an operative Calvin-Benson Cycle may be performed both by expressing single enzymes from different origins and by expressing whole operons from foreign sources as detailed above. In addition, the energy and reducing power could be supplied using at-least two parallel systems. As an essential debugging procedure LC-MS measurements may be used to track the flow of carbon in the metabolic network of the host.

The bacteria may be grown under autotrophic conditions for many generations and the adaptation process of the organism to these novel conditions may be tracked. LC-MS may be used to decipher the metabolomics and metabolite fluxes in the host. Feeding *E. coli* with $^{13}CO_2$ will allow tracking of the roots by which carbon dioxide is assimilated in the bacteria.

Following establishment of an autotrophic strain of *E. coli*, this organism may be used to test and compare one of the proposed synthetic carbon fixation cycles (described in Examples 1, 2 and 3) in vivo. Foreign enzymes will be expressed so that the host would be able to operate an alternative carbon fixation cycle and then the Calvin-Benson Cycle will be stopped by eliminating Rubisco and/or PRK. It would be extremely important to choose foreign enzymes from organisms with similar cellular conditions as in *E. coli*, if possible. These conditions include pH, temperature, ionic strength and a prokaryotic environment as opposed to eukaryotic one.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for carbon fixation, comprising an electron donor and enzymes which catalyze reactions of a carbon fixation pathway, wherein all the carboxylation reactions of the carbon fixation pathway utilize:
   (i) phophoenolpyruvate (PEP) carboxylase and acetyl-CoA carboxylase; or
   (ii) phophoenolpyruvate (PEP) carboxylase; or
   (iii) pyruvate carboxylase and acetyl-CoA carboxylase; or
   (iv) pyruvate carboxylase
   wherein products of said reactions of the carbon fixation pathway comprise oxaloacetate and malonyl-CoA, and wherein an additional product of the carbon fixation pathway is glyoxylate, wherein an in-organic carbon is introduced into a substrate to become a carboxylic acid group during said carboylation reactions, wherein said system for carbon fixation is in a non-cellular particle.

2. The system of claim 1, wherein said glyoxylate is an export product.

3. The system of claim 1, wherein an export product of the carbon fixation pathway is pyruvate.

4. The system of claim 1, wherein the enzymes of the carbon fixation pathway generate more than 0.3 μmol glyceraldehyde-3-phosphate/min/mg.

5. The system of claim 1, wherein said enzyme which performs said carboxylation enzyme is PEP carboxylase.

6. The system of claim 1, wherein at least two of said reactions of the carbon fixation pathway are carboxylation reactions.

7. The system of claim 1, wherein one of said reactions of the carbon fixation pathway utilizes methylmalonyl-CoA carboxytransferase.

8. The system of claim 1, wherein products of the reactions of the carbon fixation pathway further comprise pyruvate, phophoenolpyruvate (PEP), malate, malyl CoA and acetyl CoA.

9. The system of claim 1, wherein said electron donor is selected from the group consisting of ATP, NADH and NADPH.

10. The system of claim 1 wherein said non-cellular particle is selected from the group consisting of polymeric particles, microcapsules liposomes, microspheres, microemulsions, nano-plates, nanoparticles, nanocapsules and nanospheres.

11. The system of claim 1, wherein the enzymes of said carboxylation reactions of the carbon fixation pathway consist of:
   (i) PEP carboxylase and acetyl-CoA carboxylase; or
   (ii) PEP carboxylase; or
   (iii) pyruvate carboxylase and acetyl-CoA carboxylase; or
   (iv) pyruvate carboxylase.

\* \* \* \* \*